United States Patent
Ward et al.

(10) Patent No.: US 11,298,345 B2
(45) Date of Patent: Apr. 12, 2022

(54) COMPOUNDS THAT MODULATES AMPA RECEPTOR FUNCTION

(71) Applicant: University College Cardiff Consultants Limited, Cardiff (GB)

(72) Inventors: Simon Ward, Cardiff (GB); Paul Beswick, Cambridge (GB); Lewis Pennicott, Falmer (GB); Tristan Reuillon, Falmer (GB); Irina Chuckowree, Falmer (GB); Carolina Villalonga-Barber, Falmer (GB); Roderick Alan Porter, Falmer (GB)

(73) Assignee: University College Cardiff Consultants Limited, Cardiff (GB)

( * ) Notice: Subject to any disclaimer, the term of this patent is extended or adjusted under 35 U.S.C. 154(b) by 37 days.

(21) Appl. No.: 16/970,394

(22) PCT Filed: Mar. 1, 2019

(86) PCT No.: PCT/GB2019/050578
§ 371 (c)(1),
(2) Date: Aug. 17, 2020

(87) PCT Pub. No.: WO2019/166822
PCT Pub. Date: Sep. 6, 2019

(65) Prior Publication Data
US 2021/0113539 A1    Apr. 22, 2021

(30) Foreign Application Priority Data

Mar. 1, 2018 (GB) ...................... 1803340

(51) Int. Cl.
| | | |
|---|---|---|
| *A61P 25/28* | (2006.01) | |
| *A61K 31/4439* | (2006.01) | |
| *A61P 25/18* | (2006.01) | |
| *A61K 31/444* | (2006.01) | |
| *A61K 31/506* | (2006.01) | |
| *A61K 31/5377* | (2006.01) | |
| *A61K 31/553* | (2006.01) | |
| *A61K 45/06* | (2006.01) | |
| *C07D 401/10* | (2006.01) | |
| *C07D 401/14* | (2006.01) | |
| *C07D 403/10* | (2006.01) | |
| *C07D 413/10* | (2006.01) | |

(52) U.S. Cl.
CPC ........ *A61K 31/4439* (2013.01); *A61K 31/444* (2013.01); *A61K 31/506* (2013.01); *A61K 31/5377* (2013.01); *A61K 31/553* (2013.01); *A61K 45/06* (2013.01); *A61P 25/18* (2018.01); *A61P 25/28* (2018.01); *C07D 401/10* (2013.01); *C07D 401/14* (2013.01); *C07D 403/10* (2013.01); *C07D 413/10* (2013.01)

(58) Field of Classification Search
None
See application file for complete search history.

(56) References Cited

U.S. PATENT DOCUMENTS

| | | |
|---|---|---|
| 6,284,785 B1 | 9/2001 | Mutel et al. |
| 7,998,999 B2 | 8/2011 | Wallace et al. |
| 2009/0275751 A1 | 11/2009 | Nagato et al. |
| 2021/0139463 A1 | 5/2021 | Ward et al. |

FOREIGN PATENT DOCUMENTS

| | | |
|---|---|---|
| WO | WO-2004/046137 | 6/2004 |
| WO | WO-2006/109056 | 10/2006 |
| WO | WO-2007/107539 | 9/2007 |

(Continued)

OTHER PUBLICATIONS

Aleksandrova et al., "Antidepressant effects of ketamine and the roles of AMPA glutamate receptors and other mechanisms beyond NMDA receptor antagonism," J. Psychiatry. Neurosci., 42(4), pp. 222-229 (2017).
Arai et al., "Effect of the AMPA receptor modulator IDRA 21 on LTP in hippocampal slices," NeuroReport, 7, pp. 2211-2215 (1996).
Arai et al., "Effects of the Potent Ampakine CX614 on Hippocampal and Recombinant AMPA Receptors: Interactions with Cyclothiazide and GYKI 52466," Mol. Pharmacol., 58(4), pp. 802-813 (2000).
Berman et al., "Antidepressant Effects of Ketamine in Depressed Patients," Biol. Psychiatry, 47, pp. 351-354 (2000).

(Continued)

*Primary Examiner* — Heidi Reese
(74) *Attorney, Agent, or Firm* — Mintz, Levin, Cohn, Ferris, Glovsky and Popeo, P.C.

(57) ABSTRACT

The invention provides compounds of the formula (I): (I) wherein $A^1$, $A^2$, $R^2$, $R^4$, $B^1$, $B^2$, X, $X^1$, n, a and b are as defined are defined in the specification, to pharmaceutical compositions comprising the compounds and the compounds for use as medicaments. The compounds potentiate AMPA receptor function and are expected to be useful in the treatment of central nervous system disorders, for example in the treatment of depressive disorders, mood disorders and cognitive dysfunction associated with neuropsychiatric disorders such as schizophrenia.

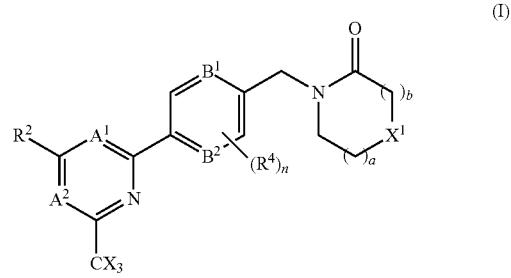

23 Claims, 1 Drawing Sheet

(56) References Cited

FOREIGN PATENT DOCUMENTS

| | | | |
|---|---|---|---|
| WO | WO-2008/053031 | 5/2008 | |
| WO | WO-2008/148832 | 12/2008 | |
| WO | WO-2008/148836 | 12/2008 | |
| WO | WO-2008148836 A1 * | 12/2008 | ............... A61P 25/00 |
| WO | WO-2009/017664 | 2/2009 | |
| WO | WO-2009/038752 | 3/2009 | |
| WO | WO-2009/053448 | 4/2009 | |
| WO | WO-2009/062930 | 5/2009 | |
| WO | WO-2009/134392 | 11/2009 | |
| WO | WO-2009/147167 | 12/2009 | |
| WO | WO-2010/063666 | 6/2010 | |
| WO | WO-2010/150192 | 12/2010 | |
| WO | WO-2011/132051 | 10/2011 | |
| WO | WO-2012/120428 | 9/2012 | |
| WO | WO-2018/146486 | 8/2018 | |
| WO | WO-2019/166822 | 9/2019 | |

OTHER PUBLICATIONS

Bloss et al., "Behavioral and biological effects of chronic S18986, a positive AMPA receptor modulator, during aging," Exp. Neurol., 210, pp. 109-117 (2008).

Bretin et al., "Pharmacological characterisation of S 47445, a novel positive allosteric modulator of AMPA receptors," PLOS ONE, 12(9):e0184429, 28 pages (2017).

Cammarota et al., "Inhibitory Avoidance Training Induces Rapid and Selective Changes in 3[H]AMPA Receptor Binding in the Rat Hippocampal Formation," Neurobiol. Learn. Mem., 64, pp. 257-264 (1995).

Dai et al., "A brain-targeted ampakine compound protects against opioid-induced respiratory depression," Eur. J. Pharmacol., 809, pp. 122-129 (2017).

Daly et al., "Efficacy and Safety of Intranasal Esketamine Adjunctive to Oral Antidepressant Therapy in Treatment-Resistant Depression: A Randomized Clinical Trial," JAMA Psychiatry, 75(2), pp. 139-148 (2018).

Derkach et al., "Regulatory mechanisms of AMPA receptors in synaptic plasticity," Nat. Rev. Neurosci., 8(2), pp. 101-113 (2007).

Dicou et al., "Positive allosteric modulators of AMPA receptors are neuroprotective against lesions induced by an NMDA agonist in neonatal mouse brain," Brain Research, 970, pp. 221-225 (2003).

Feng et al., "In Vitro P-glycoprotein Assays to Predict the in Vivo Interactions of P-glycoprotein with Drugs in the Central Nervous System," Drug Metab. Dispos., 36(2), pp. 268-275 (2008).

Field et al., "Targeting glutamate synapses in schizophrenia," Trends Mol. Med., 17(12), pp. 689-698 (2011).

Goffin et al., "7-Phenoxy-Substituted 3,4-Dihydro-2H-1,2,4-benzothiadiazine 1,1-Dioxides as Positive Allosteric Modulators of ?-Amino-3-hydroxy-5-methyl-4-isoxazolepropionic Acid (AMPA) Receptors with Nanomolar Potency," J. Med. Chem., 61, pp. 251-264 (2018).

Hampson et al., "Mechanisms underlying cognitive enhancement and reversal of cognitive deficits in nonhuman primates by the ampakine CX717," Psychopharmacology, 202(1-3), pp. 355-369 (2009).

Kalivas and Manji, "Neuroplasticity: A new window on therapeutics in neuropsychiatric disease," Neuropsychopharmacology, 33, p. 2 (2008).

Liu et al., "A single fear-inducing stimulus induces a transcription-dependent switch in synaptic AMPAR phenotype," Nature Neuroscience, 13(2), 223-231, 11 pages (2010).

Löscher et al. "The role of technical, biological and pharmacological factors in the laboratory evaluation of anticonvulsant drugs. II. Maximal electroshock seizure models," Epilepsy Res., 8, pp. 79-94 (1991).

Malinow et al., "AMPA Receptor Trafficking and Synaptic Plasticity," Annual Review of Neuroscience, 25, pp. 103-126 (2002).

Mellor, "The AMPA receptor as a therapeutic target: current perspectives and emerging possibilities," Future Med. Chem., 2(5), pp. 877-891 (2010).

Morrow et al., "Recent advances in positive allosteric modulators of the AMPA receptor," Current Opinion in Drug Discovery and Development, 9(5), pp. 571-579 (2006).

O'Neill and Witkin, "AMPA Receptor Potentiators: Application for Depression and Parkinson's Disease," Curr. Drug Targets, 8, pp. 603-620 (2007).

O'Neill et al., "AMPA receptor potentiators as cognitive enhancers," Idrugs, 10, pp. 185-192 (2007).

Passafaro et al., "Subunit-specific temporal and spatial patterns of AMPA receptor exocytosis in hippocampal neurons," Nat. Neurosci. 4(9), pp. 917-926 (2001).

Quintana et al., "The Promise of Intranasal Esketamine as a Novel and Effective Antidepressant," JAMA Psychiatry, 75(2), pp. 123-124 (2018).

Quirk and Nisenbaum, "LY404187: A Novel Positive Allosteric Modulator of AMPA Receptors," CNS Drug Rev. 8(3), pp. 255-282 (2002).

Seeburg et al., "Genetic manipulation of key determinants of ion flow in glutamate receptor channels in the mouse," Brain Res., 907, pp. 233-243 (2001).

Seeburg et al., "RNA editing of brain glutamate receptor channels: mechanism and physiology," Brain Res. Rev., 26, pp. 217-229 (1998).

Shaffer et al., "The Discovery and Characterization of the ?-Amino-3-hydroxy-5-methyl-4-isoxazolepropionic Acid (AMPA) Receptor Potentiator N-{(3S,4S)-4-[4-(5-Cyano-2-thienyl)phenoxy]tetrahydrofuran-3-yl}propane-2-sulfonamide (PF-04958242)," J. Med. Chem., 58, pp. 4291-4308 (2015).

Simmons et al., "Up-regulating BDNF with an ampakine rescues synaptic plasticity and memory in Huntington's disease knockin mice," Proc. Natl. Acad. Sci. USA, 106(12), pp. 4906-4911 (2009).

Singer, "Why Ketamine Helps Fight Depression," MIT Technology Review, 4 pages (Aug. 7, 2007).

Sobolevsky et al., "X-ray structure, symmetry and mechanism of an AMPA-subtype glutamate receptor," Nature, 462, pp. 745-756, 14 pages (2009).

Sommer et al., "RNA Editing in Brain Controls a Determinant of Ion Flow in Glutamate-Gated Channels," Cell, 67, pp. 11-19 (1991).

Stäubli et al., "Centrally active modulators of glutamate receptors facilitate the induction of long-term potentiation in vivo," Proc. Natl. Acad. Sci. USA, 91, pp. 11158-11162 (1994).

Traynelis et al., "Glutamate Receptor Ion Channels: Structure, Regulation, and Function," Pharmacol. Rev., 62(3), pp. 405-496 (2010).

Ward et al., "Challenges for and current status of research into positive modulators of AMPA receptors," British Journal of Pharmacology, 160, pp. 181-190 (2010).

Ward et al., "Integration of Lead Optimization with Crystallography for a Membrane-Bound Ion Channel Target: Discovery of a New Class of AMPA Receptor Positive Allosteric Modulators," J. Med. Chem., 54(1), pp. 78-94 (2011).

Ward et al., "Pharmacological characterization of N-[(2S)-5-(6-fluoro-3-pyridinyl)-2,3-dihydro-1H-inden-2-yl]-2-propanesulfonamide: a novel, clinical AMPA receptor positive allosteric modulator," British Journal of Pharmacology, 174, pp. 370-385 (2017).

Yamada, "Therapeutic potential of positive AMPA receptor modulators in the treatment of neurological disease," Exp. Opin. Invest. Drugs, 9(4), pp. 765-778 (2000).

Zanos et al., "NMDAR inhibition-independent antidepressant actions of ketamine metabolites," Nature, 533, pp. 481-486, 18 pages (2016).

International Search Report and Written Opinion received for Application No. PCT/GB2018/050370, dated Mar. 20, 2018, 10 pages.

International Search Report and Written Opinion received for Application No. PCT/GB2019/050578, dated May 7, 2019, 10 pages.

* cited by examiner

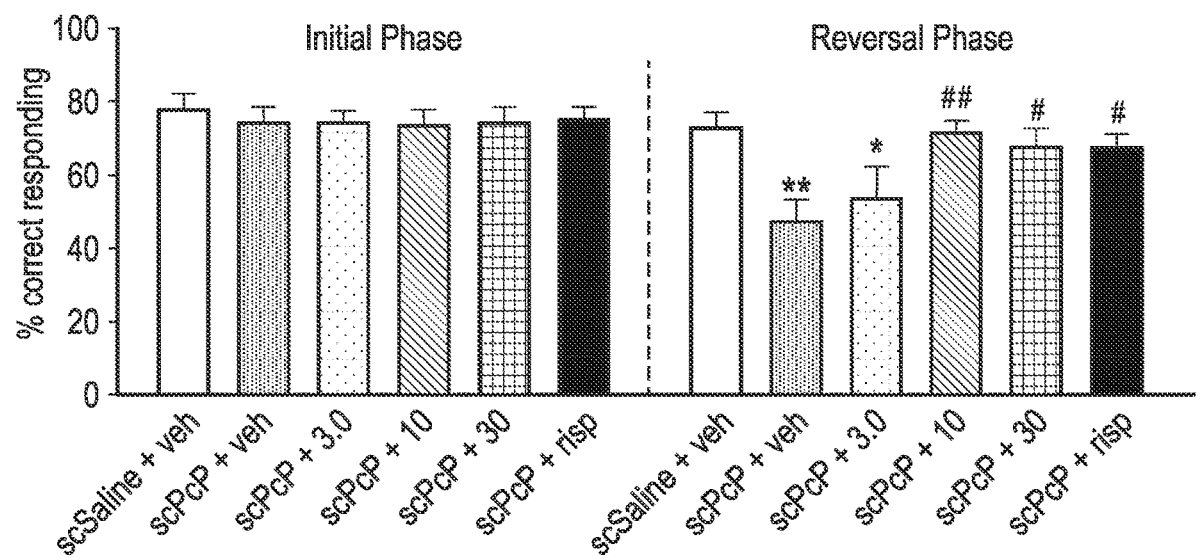

COMPOUNDS THAT MODULATES AMPA RECEPTOR FUNCTION

CROSS-REFERENCES TO RELATED APPLICATIONS

This application is a U.S. National Phase Application of PCT International Application No. PCT/GB2019/050578, filed Mar. 1, 2019, which is an International Application of and claims the benefit of priority to British Patent Application No. 1803340.7, filed on Mar. 1, 2018, the entire contents of which are herein incorporated by reference.

This invention relates to compounds of the formula (I) defined herein; to pharmaceutical compositions comprising the compounds. More specifically, the invention relates to compounds which are useful as AMPA (α-amino-3-hydroxy-5-methyl-4-isoxazole propionic acid) glutamate receptor modulators. The invention also relates to uses of the compounds and methods of treatment employing the compounds, particularly in the treatment or prevention of diseases or conditions in which potentiation of the AMPA receptor is beneficial, for example in the treatment of neurological or neuropsychiatric disease, particularly the treatment of depressive disorders, mood disorders and cognitive dysfunction associated with neuropsychiatric disorders such as schizophrenia. The invention further comprises methods for preparing the compounds and intermediates used in the preparation of the compounds.

BACKGROUND

Glutamate is the major mediator of excitatory neurotransmitter in the mammalian brain, and is involved in rapid point-to-point (synaptic) communication between neurons. The functions of glutamate are mediated via three types of fast acting ion channels; the kainate, AMPA and N-methyl-D-aspartate (NMDA) subtypes; and by the more modulatory metabotropic G-protein coupled (mGlu1-8) receptors.

AMPA receptors are tetrameric comprising four subunits (GluA1-GluA4) (Traynelis et al., Glutamate receptor ion channels: structure, regulation, and function; Pharmacol. Rev. 2010, 62, 405-496). Functional AMPA receptors can be formed from homo- or hetero-tetramers. Native receptors are almost exclusively heteromeric which leads to a diversity of receptor subunit composition in the human brain.

Studies of the X-ray structure of the membrane-bound channel show that the AMPA receptor comprises (1) an amino terminal domain (ATD), which is involved in the assembly of subunits and is the site of action for a number of molecules that modulate AMPA receptor function; (2) a ligand binding domain (LBD) including two polypeptide segments S1 and S2, which binds glutamate; (3) a transmembrane domain (TMD) containing a pore-forming ion channel; and (4) a C-terminal intracellular domain. In addition to the various subunit permutations, an additional layer of complexity is created by the existence of a number of splice variants (flip and flop variants) and sites for post-translational modification (Seeburg et al.; RNA editing of brain glutamate receptor channels: mechanism and physiology. Brain Res Brain Res Rev. 1998, 26: 217-229). RNA editing results in a positively charged arginine (R) residue replacing the genomically encoded glutamine (Q) in the M2 re-entrant loop of the GluA2 subunit, thereby restricting $Ca^{2+}$ flux through the channel and essentially rendering the receptor permeable to just $Na^+$ and $K^+$, which is deemed crucial for adult synaptic function and plasticity (Sommer et al.; RNA editing in brain controls a determinant of ion flow in glutamate-gated channels; Cell 1991, 105: 11-19; and Seeburg et al.; Genetic manipulation of key determinants of ion flow in glutamate receptor channels in the mouse. Brain Res. 2001, 907, 233-243). Extensive structural studies have been carried out on LBD constructs (Sobolevsky et al., Nature, 2009, 462, 745-756).

AMPA receptors are the most highly-expressed ionotropic glutamate receptors in the brain and are responsible for the majority of fast synaptic transmission. AMPA receptor mediated cell depolarization leads to calcium influx via NMDA receptors and the induction of synaptic plasticity (Derkach et al., 2007, Nat. Rev. Neurosci., 8:101-113).

Synaptic plasticity is the cellular process that underlies learning and memory. AMPA receptors are actively trafficked into synapses in response to neuronal activation and a functional correlate of this is that they play a crucial role in long-term potentiation, the electrophysiological correlate of synaptic plasticity (Malinow et al., Annual Review of Neuroscience, 2002, 25, 103-126).

Abnormalities in glutamatergic neurotransmissions are associated with a variety of CNS disorders and the alterations in the function of the kainate, AMPA and/or NMDA subtypes of glutamate ion channels have been explored as therapeutic targets. Of these ion channel subtypes, AMPA receptors interact very closely with NMDA receptors and together they are associated with synaptic plasticity.

AMPA modulators can also produce effects on in vivo electrophysiological measurements such as long-term potentiation, AMPA induced currents and neuronal firing rates (Hampson et al., Psychopharmacology (Berl). 2009, 202(1-3), 355-69). The observation that AMPA receptor expression increases after learning a behavioural task (Cammarota et al., Neurobiol. Learn. Mem., 1995, 64, 257-264) or after exposure to a single fear-inducing stimulus (Liu et al., Nature neuroscience, 2010, 13(2), 223-31) further emphasizes the importance of AMPA receptors in relation to learning, memory and synaptic plasticity.

In view of the critical role of AMPA receptors in the synaptic plasticity that underlies cognition, AMPA receptor modulators are expected to useful in enhancing cognitive function. AMPA receptor modulators may also be useful in the treatment of cognitive dysfunction associated with medical disorders (e.g. cognitive dysfunction associated with psychotic disorders, depressive disorders or neurodegenerative disorders). AMPA receptor modulators may be useful in the treatment of, for example, schizophrenia, Alzheimer's disease, bipolar disorder, attention deficit hyperactivity disorder, depression or anxiety, particularly in the treatment of cognitive dysfunction associated with these disorders.

Although potentiation of AMPA receptors has been shown to promote cognition, it has also been found that AMPA potentiation by certain compounds is linked to undesirable convulsant effects and seizures (Yamada Exp. Opin. Investig. Drugs, 2000, 9, 765-777). Direct activation of AMPA receptors using receptor agonists increases the risk of overstimulation and the induction of convulsant effects. This has led to research into the development of allosteric (i.e., non-glutamate binding site) AMPA receptor potentiators as a means of enhancing neuroplasticity and thus treating various neuropsychiatric disorders (Kalivas et al., Neuropsychopharmacology, 2008; 33:2).

Positive allosteric modulators (PAMs) of the AMPA receptor (AMPA-PAMs) stabilize the AMPA receptor in its active conformation following glutamate binding resulting in increased synaptic currents, thereby promoting synaptic transmission and plasticity (Mellor. The AMPA receptor as a therapeutic target: current perspectives and emerging possibilities. Future Med. Chem. 2010, 2, 877-891; and O'Neill et al., AMPA receptor potentiators as cognitive enhancers. Idrugs, 2007, 10, 185-192). Positive allosteric modulators (PAMs) are use-dependent drugs and as such only act when endogenous glutamate is released. PAM potentiation of AMPA receptors may therefore reduce the risk of undesirable side effects associated with AMPA potentiation such as convulsions.

AMPA receptor potentiation using PAMs have shown beneficial effects, including increased ligand affinity for the receptor (Arai et al., Neuroreport. 1996, 7, 221, 1-5.); reduced receptor desensitization and reduced receptor deactivation (Arai et al., 2000, 58, 802-813); and facilitate the induction of LTP in vivo (Staubli et al., Proc. Natl. Acad. Sci. 1994, 91(1), 1158-1162). The efficacy of various AMPA receptor PAMs in pre-clinical and clinical models of psychiatric disorders, such as schizophrenia, are described in (Morrow et al., Current Opinion in Drug Discovery and Development, 2006, 9(5), 571-579).

Around 1% of the population will suffer from schizophrenia at some point in their life. Symptoms such as paranoia and/or hearing voices can be reasonably well treated by existing medications. However, known drugs have little effect on other symptoms of the disease including lack of motivation, impaired social function, and, particularly, impaired cognition. Cognitive dysfunction manifests itself as difficulties with attention, memory and problem solving and result in patients experiencing a "brain fog". These largely untreated symptoms remain a huge barrier to the resumption of a fully functional, "normal" life for affected individuals.

The recognition of the unmet clinical need in schizophrenia triggered the NIH- and FDA sponsored Measurement and Treatment Research to Improve Cognition in Schizophrenia (MATRICS) initiative that mapped out the regulatory path for treatments for the cognitive impairment associated with schizophrenia (CIAS). Most therapeutic approaches to the treatment of cognitive impairment in schizophrenia have focused on the glutamate system aiming to either directly or indirectly increase NMDA receptor function (Field et al., Trends Mol. Med., 2011, 17, 689-98). Direct approaches to increasing NMDA receptor function include glycine transporter type 1 (GlyT1) inhibitors (e.g. R1678, Roche). Indirect approaches include mGluR2 positive allosteric modulators (PAMs), mGluR5 PAMs, mGluR2/3 agonists (for example pomaglumetad methionil, LY2140023 Lilly) and D-amino acid oxidase inhibitors. However, there remains a need for new therapies which improve cognitive performance in subjects with schizophrenia and other CNS conditions.

Clinical studies have shown that ketamine provides rapid relief from the symptoms of depression, often in a matter of minutes. This finding has generated significant research interest, because conventional anti-depressants such as SSRI's often take weeks or even months to show anti-depressant effects. Initial studies also suggest that ketamine may have the potential to provide potent fast-acting antidepressant effects even in traditionally difficult to treat patients with severe treatment resistant depression (Berman et al.; Antidepressant effects of ketamine in depressed patients; Biol. Psychiatry. 2000, 47(4), 351-354). More recently Daly et al., JAMA Psychiatry, 2018, 75(2), 139-148) report a phase 2 study showing that intranasal administration esketamine was efficacious in patients with treatment-resistant depression and that the onset of effects were rapid and sustained. However, ketamine has several side-effects, including hallucinogenic and addictive properties, which would make abuse of the drug likely. It is therefore unlikely that ketamine will be widely adopted as a treatment for depression.

It has recently been found that the antidepressant effects observed with ketamine are attributable to a metabolite of ketamine, (2R,6R)-hydroxynorketamine, and that this metabolite acts as an AMPA receptor potentiator. In mouse models, the metabolite provides rapid anti-depressant-like effects which persist for at least three days (Zanos et al., NMDA receptor inhibition-independent antidepressant actions of a ketamine metabolite. Nature, May 4, 2016) Aleksandrova et al., (J. Psychiatry. Neurosci., 2017; 42(4), 222-229) also indicates that AMPA receptors play a key role in mediating the anti-depressant effects of ketamine and suggests that agents which enhance the function of AMPA receptors may be beneficial in the treatment of depression.

Accordingly, AMPA receptor potentiators may be useful in the treatment of, for example, depressive disorder (e.g. major depressive disorder, persistent depressive disorder (dysthymia) or substance/medication induced depressive disorders), anxiety or bipolar-disorders. AMPA receptor potentiators may be particularly useful in the treatment of treatment resistant depressive disorders, for example in the treatment of depression that is resistant to conventional anti-depressant therapies including, but not limited to, tricyclic antidepressants, MAOIs and/or SSRIs.

S47445 is a tricyclic AMPA-PAM of the formula:

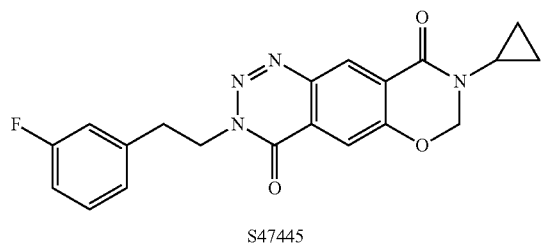

S47445

This compound is described to be a selective AMPA-PAM and shows pro-cognitive effects in rodent models as well as providing neuroprotective effects. The compound is stated to be in clinical trials for the treatment of major depressive disorder and Alzheimer's disease (Bretin et al.; Pharmacological characterisation of S 47445, a novel positive allosteric modulator of AMPA receptors; PLoS ONE. 2017, 12(9), e0184429).

Goffin et al., describe certain 7-phenoxy-substituted 3,4-dihydro-2H-1,2,4-benzothiadiazine 1,1-dioxides as AMPA-PAMs (J. Med. Chem., 2018, 61 (1), pp 251-264).

WO2009/147167 discloses certain indane derivatives which are described as potentiators of AMPA receptors.

WO2007/107539, WO2008/053031, WO2008/148832, WO2008/148836 and Ward et al., J. Med. Chem. 2011, 54, 78-94 disclose certain pyrazole derivatives as potentiators of AMPA receptors.

WO2010/150192 describes certain isopropylsulphonamide derivatives as potentiators of AMPA receptors. This patent application discloses the compound PF-4958242 as example 4. It has been reported that PF-4958242 provided a relatively narrow therapeutic window between the pro-cognitive effects and pro-convulsant activity (J. Med. Chem., 2015, 58 (10), 4291-4308).

WO2009062930; WO2009053448; WO2009038752; WO2007107539; Ward et al., British Journal of Pharmacology, 2010, 160, 181-190, 2010; and Ward et al., British Journal of Pharmacology, 2017, 174, 370-385, describe certain compounds that are stated to be AMPA receptor potentiators.

There remains a need for compounds which potentiate AMPA receptors to, for example, provide a pro-cognitive effect. There is also a need for potentiators of AMPA receptors which have a wide therapeutic window between the desirable pro-cognitive effects and the onset of undesirable side-effects, particularly pro-convulsant activity.

An object of the present invention is to provide compounds which potentiate AMPA receptors. Such compounds may be useful for the treatment of diseases associated with glutamatergic disorders, for example as described herein, including but not limited to the use of the compounds in the treatment of major depressive disorder, bipolar disorders or Alzheimer's disease. The compounds may be useful for enhancing cognitive function and/or synaptic plasticity and/or an imbalance in excitatory/inhibitory neurotransmission, particularly when associated with central nervous system (CNS) disorders. In particular the compounds may be useful in the treatment of neurological or neuropsychiatric disease. More particularly the compounds may be useful for the treatment of cognitive impairment associated with a neurological or neuropsychiatric disease.

BRIEF SUMMARY OF THE DISCLOSURE

In accordance with one aspect of the present invention there is provided a compound of the formula (I), or a pharmaceutically acceptable salt thereof:

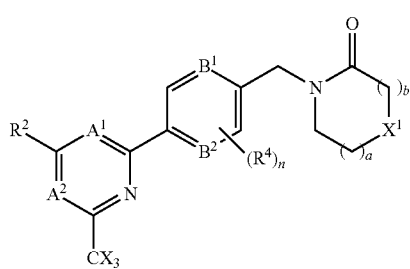

(I)

$A^1$ is N or $CR^1$;
$A^2$ is N or $CR^3$;
and wherein only a single one of $A^1$ and $A^2$ may be N;
$R^1$ is selected from the group consisting of: H, CN, $C_{1-4}$ alkyl, $C_{1-4}$ haloalkyl, $C_{3-4}$ cycloalkyl, —$C_{1-4}$ alkyl-$OR^{A1}$ and —$C(O)NR^{A1}R^{B1}$;
$R^2$ is selected from the group consisting of: H, CN, $C_{1-4}$ alkyl, $C_{1-4}$ haloalkyl, $C_{3-4}$ cycloalkyl, —$C_{1-4}$ alkyl-$OR^{A2}$ and —$C(O)NR^{A2}R^{B2}$;
$R^3$ is selected from H, $C_{1-4}$ alkyl, $C_{1-4}$ haloalkyl, $C_{3-4}$ cycloalkyl, —$C_{1-4}$ alkyl-$OR^{A3}$ and —$C(O)NR^{A3}R^{B3}$;
each X is independently H or F, provided at least one X is F;
$B^1$ and $B^2$ are independently CH or N;
$R^4$ is halo;
$X^1$ is O or $CH_2$;
$R^{A1}$, $R^{B1}$, $R^{A2}$, $R^{B2}$, $R^{A3}$ and $R^{B3}$ are each independently selected from: H and $C_{1-4}$ alkyl;
a is an integer selected from 0, 1 or 2;
b is an integer selected from 0, 1 or 2;
a+b is 0, 1, 2 or 3; and
n is 0, 1 or 2;
with the following provisos:
(i) $R^1$, $R^2$ and $R^3$ are not all H;
(ii) when $A^1$ is N, at least one of $R^2$ and $R^3$ is $C_{1-4}$ alkyl or $C_{1-4}$ haloalkyl;
(iii) when $A^2$ is N, at least one of $R^1$ and $R^2$ is $C_{1-4}$ alkyl or $C_{1-4}$ haloalkyl; and
(iv) when $A^1$ is $CR^1$, $R^1$ is —$CH_2OH$ and $B^1$ is N, then $R^2$ is not H.

In accordance with another aspect of the present invention there is provided a compound of the formula (I), or a pharmaceutically acceptable salt thereof:

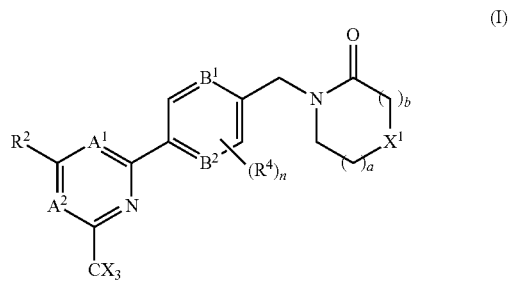

(I)

$A^1$ is N or $CR^1$;
$A^2$ is N or $CR^3$;
and wherein only a single one of $A^1$ and $A^2$ may be N;
$R^1$ is selected from the group consisting of: H, CN, $C_{1-4}$ alkyl, $C_{1-4}$ haloalkyl, $C_{3-4}$ cycloalkyl, —$C_{1-4}$ alkyl-$OR^{A1}$ and —$C(O)NR^{A1}R^{B1}$;
$R^2$ is selected from the group consisting of: H, CN, $C_{1-4}$ alkyl, $C_{1-4}$ haloalkyl, $C_{3-4}$ cycloalkyl, —$C_{1-4}$ alkyl-$OR^{A2}$ and —$C(O)NR^{A2}R^{B2}$;
$R^3$ is selected from H, $C_{1-4}$ alkyl, $C_{1-4}$ haloalkyl, $C_{3-4}$ cycloalkyl, —$C_{1-4}$ alkyl-OH and —$C(O)NR^{A3}R^{B3}$;
each X is independently H or F, provided at least one X is F;
$B^1$ and $B^2$ are independently CH or N;
$R^4$ is halo;
$X^1$ is O or $CH_2$;
$R^{A1}$, $R^{B1}$, $R^{A2}$, $R^{B2}$, $R^{A3}$ and $R^{B3}$ are each independently selected from: H and $C_{1-4}$ alkyl;
a is an integer selected from 0, 1 or 2;
b is an integer selected from 0, 1 or 2;
a+b is 0, 1, 2 or 3; and
n is 0, 1 or 2;
with the following provisos:
(i) $R^1$, $R^2$ and $R^3$ are not all H;
(ii) when $A^1$ is N, at least one of $R^2$ and $R^3$ is $C_{1-4}$ alkyl or $C_{1-4}$ haloalkyl;
(iii) when $A^2$ is N, at least one of $R^1$ and $R^2$ is $C_{1-4}$ alkyl or $C_{1-4}$ haloalkyl;
(iv) when $A^1$ is $CR^1$, $R^1$ is —$CH_2OH$ and $B^1$ is N, then $R^2$ is not H; and
(v) when $A^1$ is $CR^1$, $R^1$ is —CN and $B^1$ is N, then $R^2$ is not H.

Also provided is a pharmaceutical formulation comprising a compound of the invention and a pharmaceutically acceptable excipient.

In some embodiments the pharmaceutical composition may be a combination product comprising an additional therapeutic agent. The additional therapeutic agent may be one or more agents used in the treatment of a CNS condition, for example a neurological or psychiatric condition, particularly therapeutic agents used for the treatment of psychotic conditions such as schizophrenia and related conditions. The additional therapeutic may be one or more agents used in the treatment of depressive disorders (e.g. major depressive disorders). Additional therapeutic agents that may be used together with the compounds of the invention are set out in the Detailed Description of the invention below.

Also provided is a compound of the invention for use as a medicament.

Also provided a compound of the invention for use in the treatment of glutamatergic disorders, especially glutamatergic disorders modulated by an AMPA receptor.

Also provided is a compound of the invention for use in the treatment of a condition which is modulated by an AMPA receptor. Suitably the compound of the invention is for use in the treatment of a condition in which AMPA receptor function is impaired.

Also provided are methods of treating a condition which is modulated by an AMPA receptor in a subject in need thereof by administering an effective amount of a compound of the invention to the subject.

A compound of the invention may be for use in the treatment of a condition in which potentiation of an AMPA receptor is beneficial. Accordingly, it may be that the compound of the invention is for use in enhancing synaptic plasticity in a subject. It may be that the compound of the invention is for use in the treatment of an imbalance in excitatory/inhibitory neurotransmission in a subject.

It may be that the compound of the invention is for use in the treatment or prevention of central nervous system (CNS) disorders associated with an alteration in one or more of cognitive function, synaptic plasticity, or an imbalance in excitatory/inhibitory neurotransmission. For example, a compound of the invention may be for use in the treatment of any of the central nervous system (CNS) disorders disclosed herein, including neurological or neuropsychiatric disorders, for example a condition selected from schizophrenia, bipolar disorder, attention-deficit hyperactivity disorder (ADHD), depression, Alzheimer's disease, Huntington's disease, Parkinson's disease, Down syndrome and other neurodevelopmental disorders, motor neuron diseases (e.g. amyotrophic lateral sclerosis), ataxia, respiratory depression and hearing disorders (for example hearing loss and tinnitus). It may be that the compound of the invention is for use in the treatment of obsessive-compulsive disorder, addiction or mood disorders (including major depressive disorders and bipolar disorders). In some embodiments, a compound of the invention is for use in the treatment of a depressive disorder, for example the treatment of a depressive disorder that is resistant to conventional anti-depressant therapies. In some embodiments, a compound of the invention is for use in the treatment of a depressive disorder or a mood disorder (e.g., a major depressive disorder, an anxiety disorder, a disruptive mood dysregulation disorder, anhedonia or suicidal ideation (suicidal thoughts)).

Also provided is a compound of the invention for use in the alteration of cognitive function, particularly for the enhancement of cognitive function, in a subject. More particularly there is provided a compound of the invention for use in the treatment of a cognitive impairment. Still more particularly there is provided a compound of the invention for use in the treatment of cognitive impairment associated with a disease or a condition. It may be that a compound of the invention is for use in the treatment of cognitive impairment associated with a psychiatric or neurological disorder, for example any of the psychiatric or neurological disorders described herein.

In a particular embodiment, there is provided a compound of the invention is for use in the treatment of cognitive dysfunction associated with schizophrenia.

BRIEF DESCRIPTION OF THE DRAWINGS

FIG. 1 shows the results from the sub-chronic PCP-induced reversal learning in female Lister Hooded rats study described in the Examples in which one of the exemplified compounds, UoS26478 was tested compared to risperidone. The FIGURE shows the mean % of correct lever presses in the initial phase and the reversal phase of the study (n=9-10 per group). "veh" refers to saline vehicle, "scPCP" refers to sub-chronic phencyclidine. "+3.0", "+10" and "+30" refers to the dose (mg/kg) of UoS26478 orally administered to the rats. "Risp" refers to risperidone and this was administered I.P. at a dose of 0.1 mg/kg).

DETAILED DESCRIPTION

Given below are definitions of terms used in this application. Any term not defined herein takes the normal meaning as the skilled person would understand the term.

Reference herein to a "compound of the invention" is a reference to any of the compounds disclosed herein including compounds of the formulae (I), (II), (III), (IV), (V), (VI) and (VII) or a pharmaceutically acceptable salt, solvate, or salt of a solvate thereof, including any of the Examples listed herein.

The term $C_{m-n}$ refers to a group with m to n carbon atoms.

The term "halo" refers to one of the halogens, group 17 of the periodic table. In particular the term refers to fluorine, chlorine, bromine and iodine. Preferably, the term refers to fluorine or chlorine.

The term "$C_{1-4}$ alkyl" refers to a linear or branched hydrocarbon chain containing 1, 2, 3 or 4 carbon atoms, for example methyl, ethyl, n-propyl, iso-propyl, n-butyl, sec-butyl and tert-butyl.

The term "$C_{1-4}$ haloalkyl", refers to a $C_{1-4}$ alkyl group substituted with at least one halogen atom independently chosen at each occurrence, for example fluorine, chlorine, bromine and iodine. The halogen atom may be present at any position on the $C_{1-4}$ alkyl chain. For example, $C_{1-4}$ haloalkyl may refer to chloromethyl, fluoromethyl, difluoromethyl, trifluoromethyl, chloroethyl (e.g. 1-chloroethyl or 2-chloroethyl), trichloroethyl (e.g. 1,2,2-trichloroethyl, 2,2,2-trichloroethyl), fluoroethyl (e.g. 1-fluoroethyl or 2-fluoroethyl), trifluoroethyl (e.g. 1,2,2-trifluoroethyl or 2,2,2-trifluoroethyl), chloropropyl, trichloropropyl, fluoropropyl, trifluoropropyl. A $C_{1-4}$ haloalkyl group may be a $C_{1-4}$ fluoroalkyl group, i.e. a $C_{1-4}$ alkyl group substituted with at least one fluorine atom (e.g. fluoromethyl, difluoromethyl or trifluoromethyl, particularly trifluoromethyl).

The term "—$C_{1-4}$alkyl-OR$^{4x}$", where x=1, 2 or 3, refers to a $C_{1-4}$ alkyl group substituted by an —OR$^{4x}$ group. Examples of —$C_{1-4}$alkyl-OR$^{4x}$ groups include —CH$_2$OH, —CH$_2$OMe, —CH$_2$OEt, —CH$_2$CH$_2$OH, —CH$_2$CH$_2$OMe, —CH(OH)CH$_3$, —CH(OMe)CH$_3$, —CH$_2$CH(OH)CH$_3$ or —CH$_2$CH(OMe)CH$_3$.

The term "$C_{3-4}$ cycloalkyl" includes a saturated hydrocarbon ring system containing 3 or 4 carbon atoms (cyclopropyl or cyclobutyl).

The group $R^4$ (when present) may be located on any carbon atom in the central ring of formula (I). For example, when $B^1$ and/or $B^2$ are CH, an $R^4$ group may be present on the carbon represented by $B^1$ and/or $B^2$.

In the compounds of the invention only a single one of $A^1$ and $A^2$ may be N. Thus $A^1$ may be CR$^1$ and $A^2$ may be CR$^3$; or $A^1$ may be N and $A^2$ is CR$^3$; or $A^1$ may be CR$^1$ and $A^2$ is N. However, $A^1$ and $A^2$ are not both N together.

A bond terminating in a "⌢" or "*" represents that the bond is connected to another atom that is not shown in the structure. A bond terminating inside a cyclic structure and not terminating at an atom of the ring structure represents that the bond may be connected to any of the atoms in the ring structure where allowed by valency.

The invention contemplates pharmaceutically acceptable salts of the compounds of the invention in so far as such compounds may form salts. These may include the acid addition and base salts of the compounds. These may be acid addition and base salts of the compounds. Suitable pharmaceutically acceptable salts are described in for example "Handbook of Pharmaceutical Salts: Properties, Selection, and Use" by Stahl and Wermuth (Wiley-VCH, Weinheim, Germany, 2002). Salts may be formed using well known methods.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J. Pharm. Sci, 64 (8), 1269-1288 by Haleblian (August 1975).

Hereinafter all references to compounds of the invention include references to salts, solvates and complexes thereof and to solvates and complexes or salts thereof.

Compounds of the invention may exist in a single crystal form or in a mixture of crystal forms or they may be amorphous all such forms are encompassed by the present invention. Thus, compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

Certain compounds of the invention are capable of existing in stereoisomeric forms. It will be understood that the invention encompasses the use of all optical isomers of the compounds of the invention. Where a compound has a stereocentre, both (R) and (S) stereoisomers are contemplated by the invention, equally mixtures of stereoisomers or a racemic mixture are contemplated by the present application. Where the compound is a single stereoisomer the compounds may still contain other enantiomers as impurities. Hence a single stereoisomer does not necessarily have an enantiomeric excess (e.e.) of 100% but could have an e.e. or d.e. of about at least 85%. Enantiomerically pure forms are a particular aspect of the invention. Conventional techniques for the preparation/isolation of individual enantiomers when necessary include chiral synthesis from a suitable optically pure precursor or resolution of the racemate (or the racemate of a salt or derivative) using, for example, chiral high pressure liquid chromatography (HPLC).

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, "Stereochemistry of Organic Compounds" by E. L. Eliel and S. H. Wilen (Wiley, 1994).

The present invention also includes all pharmaceutically acceptable isotopically-labelled compounds of formulae (I) to (VII) defined herein, wherein one or more atoms are replaced by atoms having the same atomic number, but an atomic mass or mass number different from the atomic mass or mass number most commonly found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, (D) may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labelled compounds can generally be prepared by conventional techniques known to those skilled in the art or by processes analogous to those described using an appropriate isotopically-labelled reagent in place of the non-labelled reagent previously employed.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention.

Prodrugs of the compounds of the invention are also contemplated within the scope of the invention. A prodrug is a compound which acts as a drug precursor which, upon administration to a subject, undergoes conversion by metabolic or other chemical processes to yield a compound of formulae (I) to (VII) defined herein. For example, an —OH group may be converted to an ester or a carbamate, which upon administration to a subject will undergo conversion back to the free hydroxyl group. Examples of prodrugs and their uses are well known (e.g., Berge et al., "Pharmaceutical Salts", J. Pharm. Sci. 1977, 66, 1-19). The prodrugs can be prepared in situ during the final isolation and purification of the compounds, or by separately reacting the purified compound with a suitable esterifying agent.

The terms "treating", or "treatment" refer to any beneficial effect in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease.

An "effective amount" is an amount sufficient to accomplish a stated purpose (e.g. achieve the effect for which it is administered, treat a disease, reduce enzyme activity, increase enzyme activity, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The therapeutically effective amount of a compound of the invention can be initially estimated from cell culture assays. Target concentrations will be those concentrations of active compound(s) that are capable of achieving the therapeutic effect described herein, as measured using the methods described herein or known in the art.

Therapeutically effective amounts for use in humans can also be determined from animal models using known methods. For example, a dose for humans can be formulated to achieve a concentration that has been found to be effective in animals. The dosage in humans can be adjusted by monitoring compound effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

A prophylactic or therapeutic treatment regimen is suitably one that does not cause substantial toxicity and yet is effective to treat the clinical symptoms demonstrated by the particular patient. This determination of a dosage regimen is generally based upon an assessment of the active compound by considering factors such as compound potency, relative bioavailability, patient body weight, presence and severity of adverse side effects, preferred mode of administration and the toxicity profile of the selected agent.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

Compounds

In certain embodiments the compound of formula (I) is of the formula (II), or a pharmaceutically acceptable salt thereof:

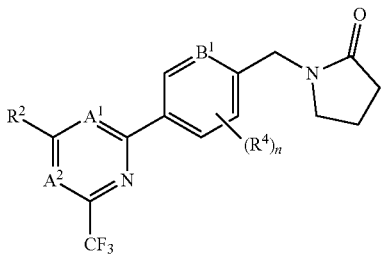
(II)

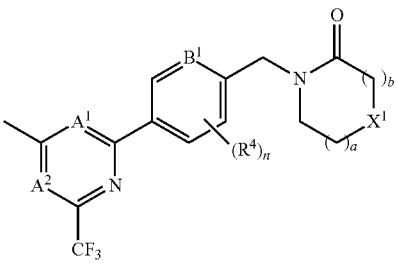
(VI)

In certain embodiments the compound of formula (I) is of the formula (III), or a pharmaceutically acceptable salt thereof:

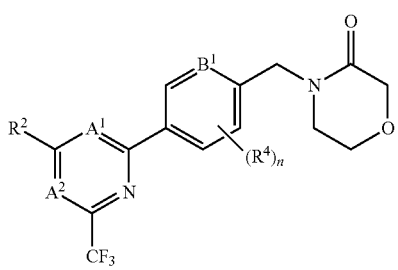
(III)

In certain embodiments the compound of formula (I) is of the formula (VII), or a pharmaceutically acceptable salt thereof:

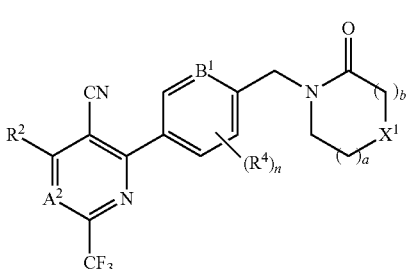
(VII)

In certain embodiments the compound of formula (I) is of the formula (IV), or a pharmaceutically acceptable salt thereof:

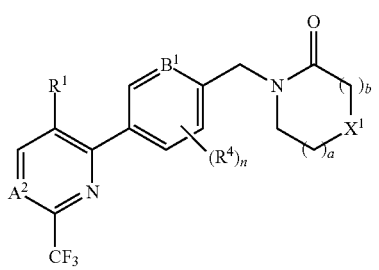
(IV)

In certain embodiments the compound of formula (I) is of the formula (V), or a pharmaceutically acceptable salt thereof:

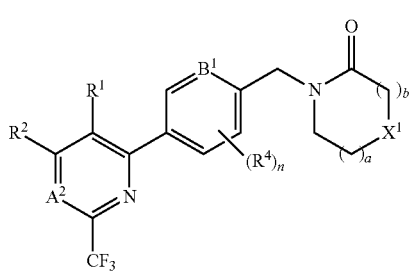
(V)

In certain embodiments the compound of formula (I) is of the formula (VI), or a pharmaceutically acceptable salt thereof:

Particular compounds of the invention include, for example, compounds of formulae (I), (II), (III), (IV), (V), (VI) or (VII), or a pharmaceutically acceptable salt thereof, wherein, unless otherwise stated, each of $R^1$, $R^2$, $R^3$, $R^4$, $A^1$, $A^2$, $B^1$, $B^2$, X, $X^1$, a, b and n has any of the meanings defined hereinbefore or in any one or more of paragraphs (1) to (58) hereinafter:

(1) The group CX is —$CHF_2$ or —$CF_3$.
(2) The group CX is —$CF_3$.
(3) $A^1$ is $CR^1$.
(4) $A^1$ is $CR^1$ and $R^1$ is selected from the group consisting of CN, $C_{1-4}$ alkyl, $C_{1-4}$ haloalkyl, $C_{3-4}$ cycloalkyl, —$C_{1-4}$ alkyl-$OR^{A1}$ and —$C(O)NR^{A1}R^{B1}$.
(5) $A^1$ is $CR^1$ and $R^1$ is selected from the group consisting of: H, CN, $C_{1-3}$ alkyl, $C_{1-3}$ fluoroalkyl, alkyl-OH, —$C_{1-3}$ alkyl-OMe, —$C(O)NH_2$; —$C(O)NHMe$ and —$C(O)N(Me)_2$.
(6) $A^1$ is $CR^1$ and $R^1$ is selected from the group consisting of: CN, $C_{1-3}$ alkyl, $C_{1-3}$ fluoroalkyl, alkyl-OH, —$C_{1-3}$ alkyl-OMe, —$C(O)NH_2$; —$C(O)NHMe$ and —$C(O)N(Me)_2$.
(7) $A^1$ is $CR^1$ and $R^1$ is selected from the group consisting of: H, CN, methyl, ethyl, —$CH_2F$, —$CH_2OH$, —$CH_2OMe$, —$C(O)NH_2$; —$C(O)NHMe$ and —$C(O)N(Me)_2$.
(8) $A^1$ is $CR^1$ and $R^1$ is selected from the group consisting of: H, CN, methyl, —$CH_2F$ and —$CH_2OH$ (e.g. $R^1$ is selected from the group consisting of: H, CN, methyl and —$CH_2F$).
(9) $A^1$ is $CR^1$ and $R^1$ is —CN.
(10) $A^1$ is $CR^1$ and $R^1$ is methyl or ethyl, preferably methyl.
(11) $A^1$ is $CR^1$ and $R^1$ is —$CH_2F$.
(12) $A^1$ is $CR^1$ and $R^1$ is —$CH_2OH$.
(13) $A^1$ is $CR^1$ and $R^1$ is H.
(14) $A^1$ is N.
(15) $A^1$ is N and $A^2$ is $CR^3$.
(16) $A^1$ is N, $R^2$ is methyl or ethyl, and $A^2$ is CH.
(17) $R^2$ is selected from the group consisting of: $C_{1-4}$ alkyl, $C_{1-4}$ haloalkyl, $C_{3-4}$ cycloalkyl, —$C_{1-4}$ alkyl-$OR^{A2}$ and —$C(O)NR^{A2}R^{B2}$.

(18) $R^2$ is selected from the group consisting of: H, $C_{1-4}$ alkyl, $C_{1-4}$ haloalkyl and —$C_{1-4}$ alkyl-$OR^{42}$.
(19) $R^2$ is selected from the group consisting of: H, $C_{1-3}$ alkyl, $C_{1-3}$ fluoroalkyl, alkyl-OH and —$C_{1-3}$alkyl-OMe.
(20) $R^2$ is selected from the group consisting of: $C_{1-3}$ alkyl, $C_{1-3}$ fluoroalkyl, —$C_{1-3}$ alkyl-OH and —$C_{1-3}$ alkyl-OMe.
(21) $R^2$ is selected from the group consisting of: H, $C_{1-3}$ alkyl, —$C_{1-3}$ alkyl-OH and —$C_{1-3}$ alkyl-OMe.
(22) $R^2$ is selected from the group consisting of: H, methyl, ethyl, —$CH_2OH$ and —$CH_2OMe$.
(23) $R^2$ is selected from the group consisting of: H, methyl and —$CH_2OH$.
(24) $R^2$ is selected from the group consisting of: methyl and —$CH_2OH$.
(25) $R^2$ is H.
(26) $A^2$ is N.
(27) $A^2$ is N and $A^1$ is $CR^1$.
(28) $A^2$ is N, $A^1$ is $CR^1$, and $R^1$ is as defined in any of (3) to (13) above.
(29) $A^2$ is N, $A^1$ is $CR^1$, and $R^1$ is methyl or —$CH_2F$.
(30) $A^2$ is $CR^3$ and $R^3$ is selected from the group consisting of: $C_{1-4}$ alkyl, $C_{1-4}$ haloalkyl, $C_{3-4}$ cycloalkyl, —$C_{1-4}$ alkyl-$OR^{43}$ and —$C(O)NR^{43}R^{B3}$.
(31) $A^2$ is $CR^3$ and $R^3$ is selected from the group consisting of: $C_{1-4}$ alkyl, $C_{1-4}$ haloalkyl, $C_{3-4}$ cycloalkyl, —$C_{1-4}$ alkyl-OH and —$C(O)NR^{43}R^{B3}$
(32) $A^2$ is $CR^3$ and $R^3$ is selected from the group consisting of: H, $C_{1-3}$ alkyl, $C_{1-3}$ haloalkyl, alkyl-$OR^{43}$ and —$C(O)NR^{43}R^{B3}$.
(33) $A^2$ is $CR^3$ and $R^3$ is selected from the group consisting of: H, $C_{1-3}$ alkyl, $C_{1-3}$ haloalkyl, alkyl-OH and —$C(O)NR^{43}R^{B3}$
(34) $A^2$ is $CR^3$ and $R^3$ is selected from the group consisting of: H, $C_{1-3}$ alkyl, $C_{1-3}$ haloalkyl and —$C_{1-3}$ alkyl-$OR^{43}$.
(35) $A^2$ is $CR^3$ and $R^3$ is selected from the group consisting of: H, $C_{1-3}$ alkyl, $C_{1-3}$ haloalkyl and —$C_{1-3}$ alkyl-OH.
(36) $A^2$ is $CR^3$ and $R^3$ is selected from the group consisting of: H, $C_{1-3}$ fluoroalkyl and —$C_{1-3}$ alkyl-OH.
(37) $A^2$ is $CR^3$ and $R^3$ is selected from the group consisting of: H, —$CH_2F$ and —$CH_2OH$.
(38) $A^2$ is $CR^3$ and $R^3$ is H.
(39) $B^2$ is CH.
(40) $B^1$ and $B^2$ are both N.
(41) $B^1$ is N and $B^2$ is CH.
(42) $B^1$ and $B^2$ are both CH.
(43) $R^4$ is F.
(44) n is 0 or 1.
(45) n is 0 or 1 and $R^4$ is F.
(46) n is 0.
(47) n is 1 and $R^4$ is F.
(48) $X^1$ is $CH_2$.
(49) $X^1$ is O.
(50) a+b is 1, 2 or 3.
(51) a+b is 1 or 2.
(52) The group of the formula:

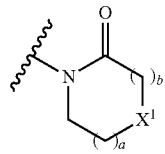

is selected from the group consisting of:

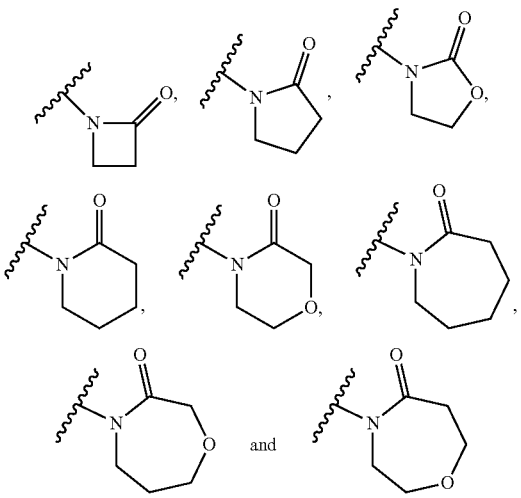

for example a group selected from:

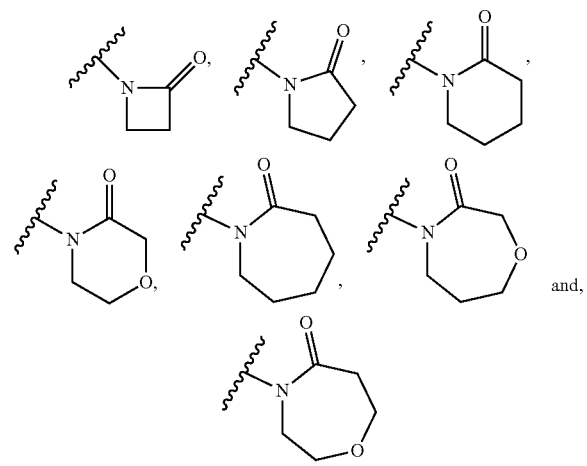

(53) The group of the formula:

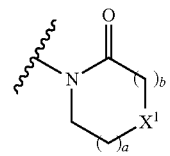

is selected from:

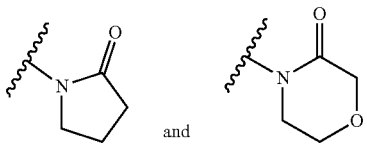 [SMILES: *N1CCCC1=O ; *N1CCOCC1=O]

and

(54) The group of the formula:
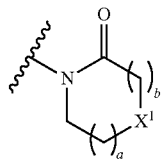
is
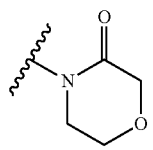
(55) The group of the formula:
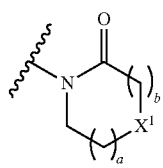
is
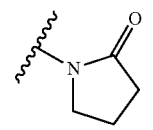 [SMILES: *N1CCCC1=O]
(56) The group of the formula:
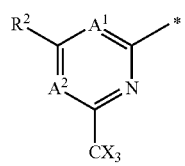
is selected from the group consisting of:
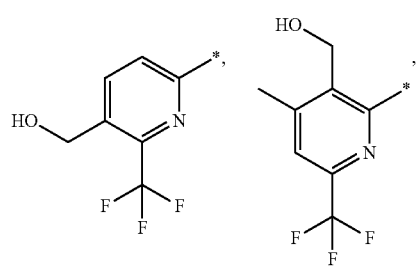
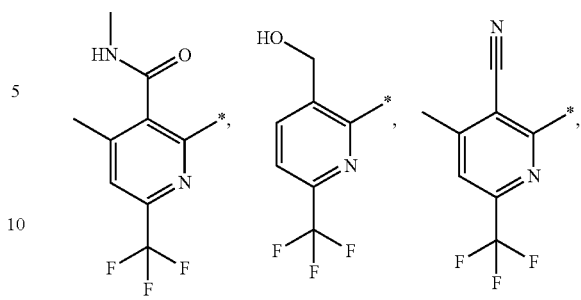
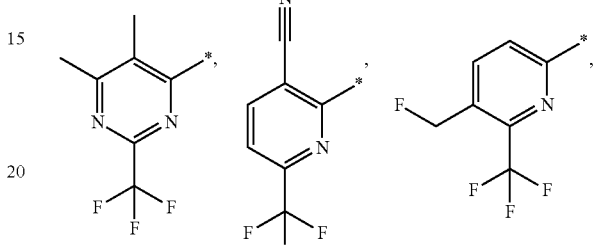
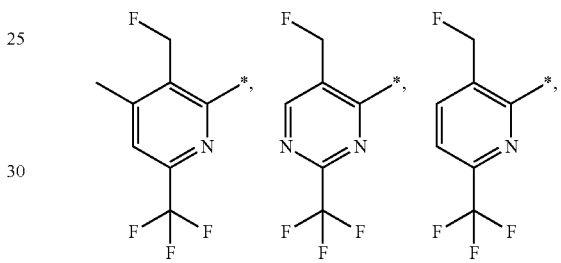
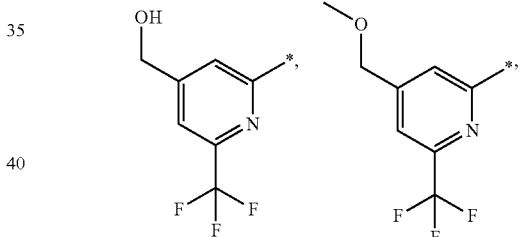
and
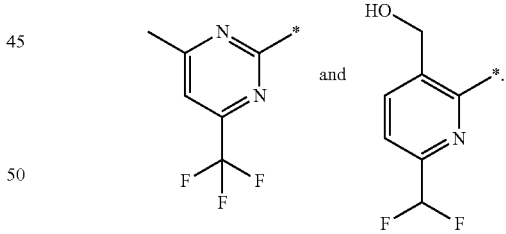
(57) The group of the formula:
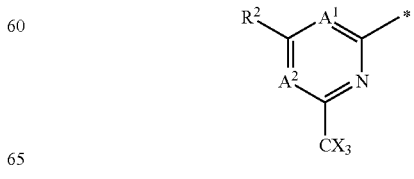

is selected from the group consisting of:

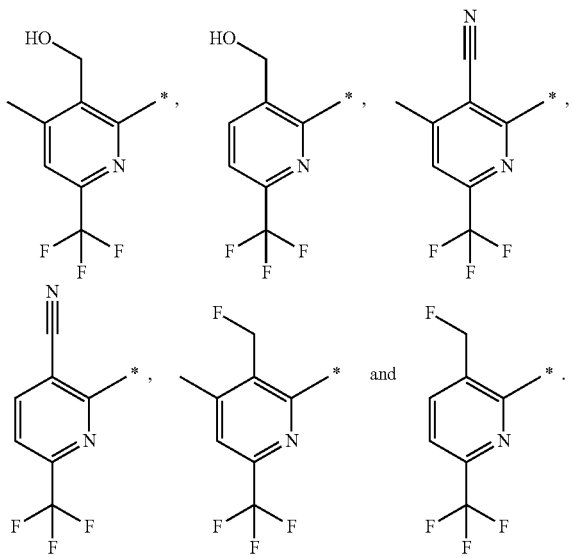

(58) when $A^1$ is N, $R^2$ is $C_{1-4}$ alkyl or $C_{1-4}$ haloalkyl (e.g. $R^2$ is methyl or ethyl).

In certain embodiments there is provided a compound of the formula (I) wherein:
$A^1$ is N or $CR^1$;
$A^2$ is N or $CR^3$;
and wherein only a single one of $A^1$ and $A^2$ may be N;
$R^1$ is selected from the group consisting of: H, CN, methyl, fluoromethyl and hydroxymethyl;
$R^2$ is selected from the group consisting of: H, methyl and hydroxymethyl;
$R^3$ is selected from H, fluoromethyl and hydroxymethyl;
each X is F;
$B^1$ is CH or N;
$B^2$ is CH;
$X^1$ is O or $CH_2$;
a is an integer selected from 0, 1 or 2;
b is an integer selected from 0, 1 or 2;
a+b is 0, 1, 2 or 3; and
n is 0;
with the following provisos:
$R^1$, $R^2$ and $R^3$ are not all H;
(ii) when $A^1$ is N, at least one of $R^2$ and $R^3$ is methyl; and
(iii) when $A^2$ is N, at least one of $R^1$ and $R^2$ is methyl
(iv) when $A^1$ is $CR^1$, $R^1$ is hydroxymethyl and $B^1$ is N, then $R^2$ is not H.

Preferably in this embodiment the group of the formula:

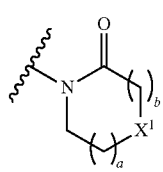

is selected from:

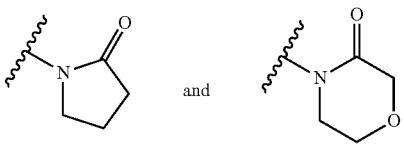 [SMILES: *N1CCCC1=O ; *N1CCOCC1=O]

In certain embodiments there is provided a compound of the formula (I) wherein $B^1$ is N; $B^2$ is CH; and $R^1$ is not H.

In certain embodiments there is provided a compound of the formula (I) wherein $B^1$ is N; $B^2$ is CH;
$R^1$ is selected from the group consisting of: CN, $C_{1-3}$ alkyl, $C_{1-3}$ haloalkyl, alkyl-OH, —$C_{1-3}$ alkyl-OMe, —C(O)NH$_2$; —C(O)NHMe and —C(O)N(Me)$_2$; and
$R^2$ is selected from any of (17) to (25) above. Preferably in this embodiment n is 0.

In certain embodiments there is provided a compound of the formula (I) wherein $B^1$ is N; $B^2$ is CH;
$R^1$ is selected from the group consisting of: CN, $C_{1-3}$ alkyl, $C_{1-3}$ fluoroalkyl, alkyl-OH, and —$C_{1-3}$ alkyl-OMe; and
$R^2$ is selected from the group consisting of: H, $C_{1-3}$ alkyl, $C_{1-3}$ fluoroalkyl, alkyl-OH and —$C_{1-3}$ alkyl-OMe. Preferably in this embodiment n is 0.

In certain embodiments there is provided a compound of the formula (I) wherein $B^1$ is N; $B^2$ is CH;
$R^1$ is selected from the group consisting of: CN, methyl and —CH$_2$F; and
$R^2$ is selected from H and methyl.
Preferably in this embodiment n is 0 or n is 1 and $R^4$ is F, more preferably n is 0.

In certain embodiments in the compounds of the formulae (I), (II), (III), (IV), (IV), (V), (VI) and (VII) n is 0.

In certain embodiments in the compound of formula (I) $B^1$ and $B^2$ are both CH and n is 0.

In certain embodiments in the compounds of the formulae (I), (II), (III), (IV), (V), (VI) and (VII) n is 0 and $B^1$ is CH.

In certain embodiments in the compounds of the formulae (I), (II) and (III), n is 0 and the group of the formula:

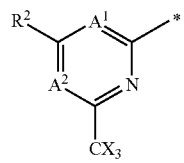

is selected from:

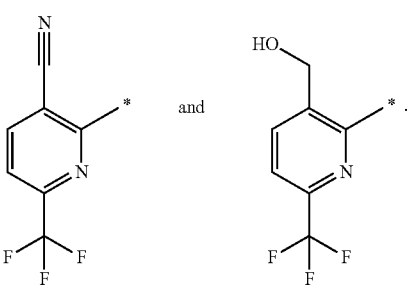

Preferably in these embodiments $B^1$ and $B^2$ are CH.

In certain embodiments in the compound of the formula (IV) $R^1$ is not H

In certain embodiments in the compound of the formula (IV) R¹ is not H (for example R¹ is as defined in any of (4) to (12) above); and
A² is CH or N (preferably A² is CH).

In certain embodiments in the compound of the formula (IV) R¹ is selected from the group consisting of: CN, $C_{1-2}$ fluoroalkyl, —$C_{1-2}$ alkyl-$OR^{A1}$ and —$C(O)NR^{A1}R^{B1}$;
$R^{A1}$ and $R^{B1}$ are each independently selected from the group consisting of: H, methyl and ethyl, preferably H and methyl; and
A² is CH or N, preferably CH.

In certain embodiments in the compound of the formula (IV) R¹ is selected from the group consisting of: CN, $C_{1-2}$ fluoroalkyl, —$C_{1-2}$ alkyl-OH and —C(O)NH(Me); and
A² is CH or N, preferably CH.

In certain embodiments in the compound of the formula (IV) R¹ is selected from the group consisting of: CN, fluoromethyl and hydroxymethyl; and
A² is CH or N, preferably CH.

In the above five embodiments of the compound of the formula (IV) n is preferably 0. More preferably n is 0 and B¹ is CH.

In certain embodiments in the compound of the formula (V) R¹ and R² are not H.

In certain embodiments in the compound of the formula (V) R¹ is selected from the group consisting of: CN, $C_{1-2}$ alkyl, $C_{1-2}$ fluoroalkyl, —$C_{1-2}$ alkyl-$OR^{A1}$ and —$C(O)NR^{A1}R^{B1}$;
R² is $C_{1-2}$ alkyl;
$R^{A1}$ and $R^{B1}$ are each independently selected from the group consisting of: H, methyl and ethyl, preferably H and methyl; and
A² is CH or N, preferably CH.

In certain embodiments in the compound of the formula (V) R¹ is selected from the group consisting of: CN, $C_{1-2}$ alkyl, $C_{1-2}$ fluoroalkyl, —$C_{1-2}$ alkyl-OH and —C(O)NH(Me);
R² is $C_{1-2}$ alkyl;
A² is CH or N, preferably CH.

In certain embodiments in the compound of the formula (V) R¹ is selected from the group consisting of: CN, methyl, fluoromethyl and hydroxymethyl;
R² is $C_{1-2}$ alkyl;
A² is CH or N, preferably CH.

In the above four embodiments of the compound of the formula (V) n is preferably 0. More preferably n is 0 and B¹ is CH.

In certain embodiments in the compound of the formula (VI) A¹ is selected from N and CR¹ (preferably CR¹);
R¹ is selected from the group consisting of: CN, $C_{1-2}$ alkyl, $C_{1-2}$ fluoroalkyl, —$C_{1-2}$ alkyl-OH and —C(O)NH(Me); and
A² is CH.

Preferably in this embodiment of the compound of the formula (VI) n is 0. More preferably n is 0 and B¹ is CH.

In certain embodiments in the compound of the formula (VII) R² is selected from the group consisting of H and $C_{1-2}$ alkyl; and
A² is CH or N, preferably CH.

Preferably in this embodiment of the compound of the formula (VII) n is 0. More preferably A² is CH, n is 0 and B¹ is CH.

In certain embodiments in the compound of the formula (VII) R² is H, A² is CH, n is 0 and B¹ is CH.

It may be that in any of the embodiments of the compounds of the formulae (I), (IV), (V), (VI) and (VII) herein a+b is 1, 2 or 3, preferably a+b is 1 or 2.

Preferably in any of the embodiments of the compounds of the formulae (I), (IV), (V), (VI) and (VII) herein, the group of the formula:

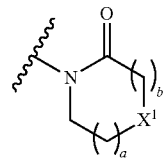

is selected from:

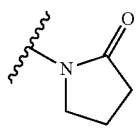 and 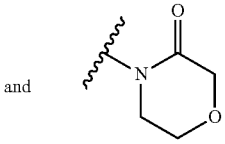

In certain embodiments in the compound of formula (V) the group of the formula:

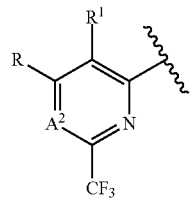

is selected from the group consisting of:

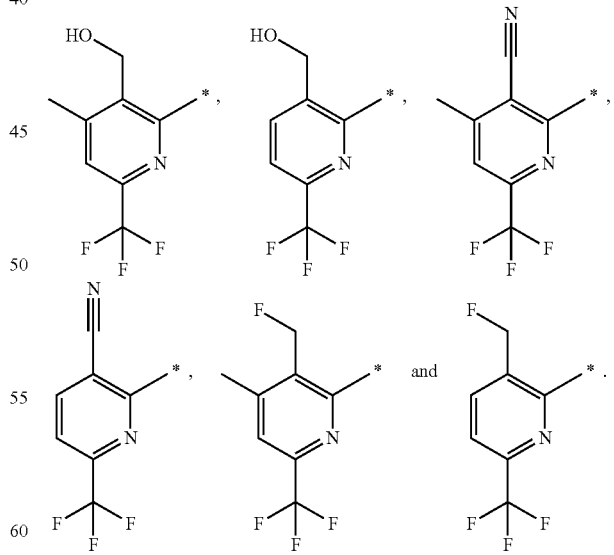

Suitably in this embodiment A² is CH; and n is 0.
Suitably in this embodiment A² is CH; n is 0 and B¹ is CH.
In another embodiment there is provided a compound of the formula (I) selected from:

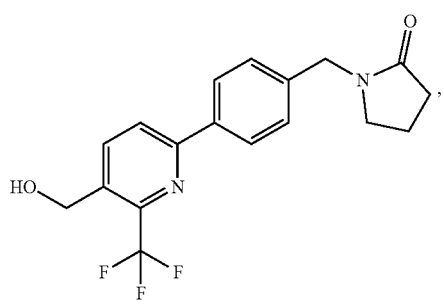
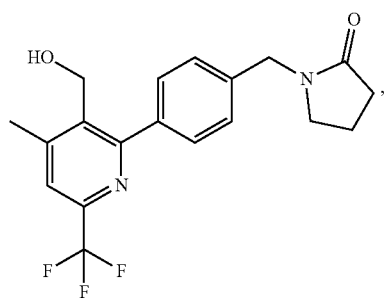
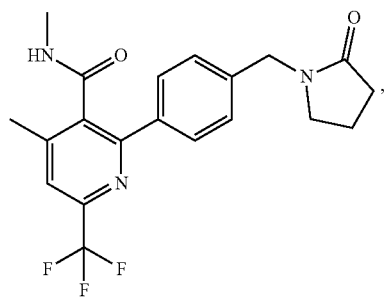
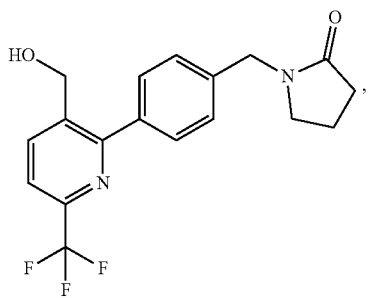
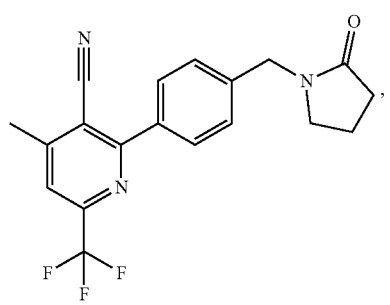
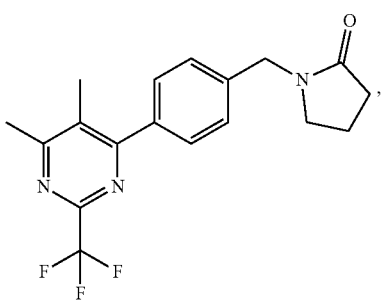
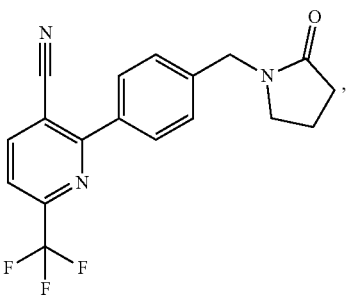
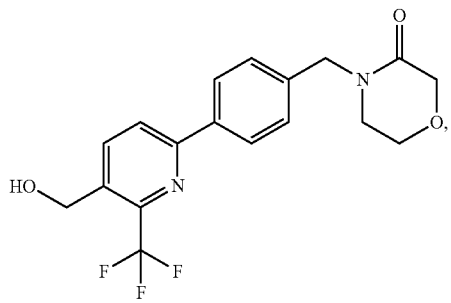
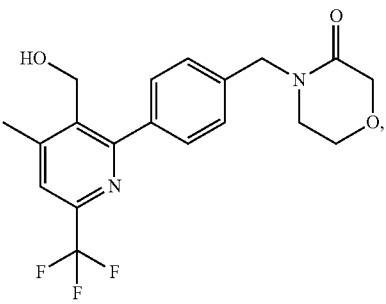
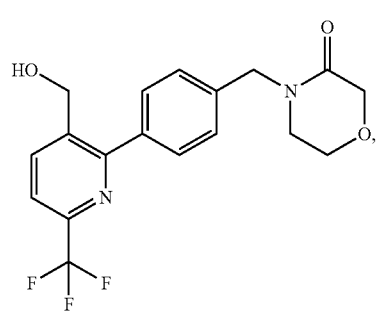

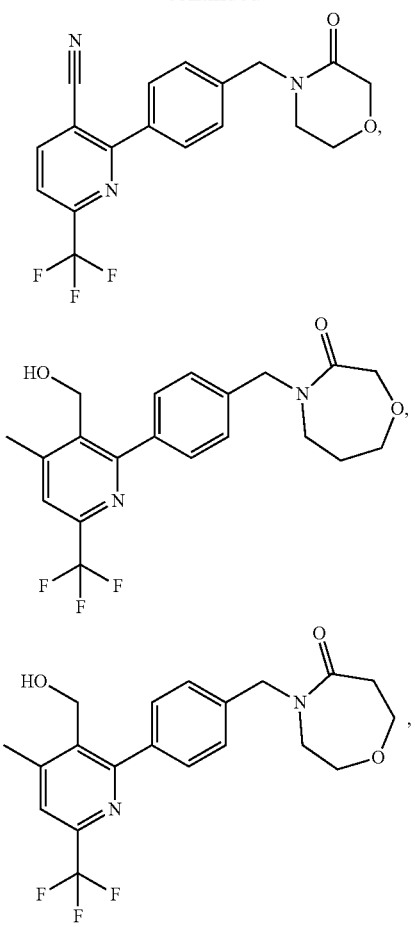
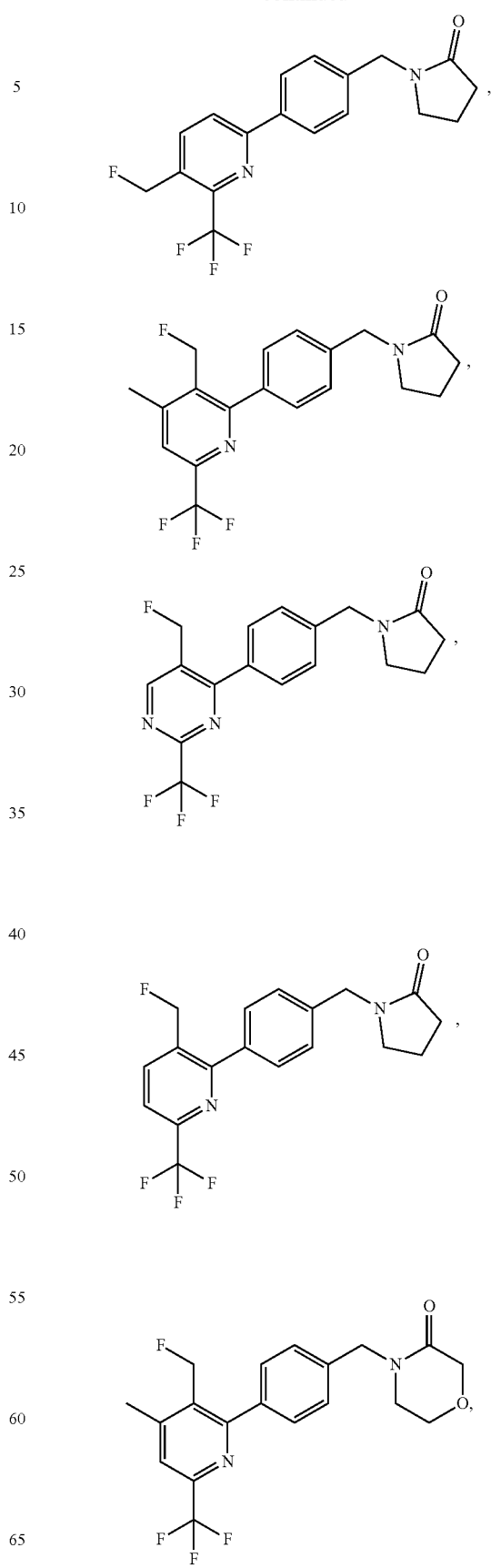

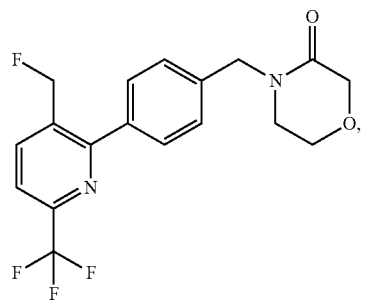

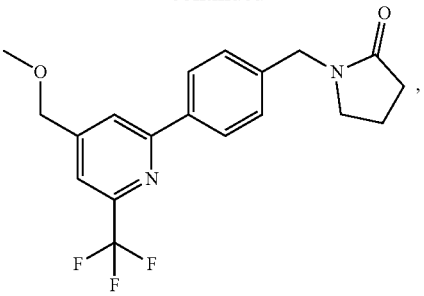

Without wishing to be bound by theory, the compounds of the invention are thought to potentiate AMPA receptors by acting as positive allosteric modulators (PAMs) of the AMPA receptor. An "allosteric modulator" is an agent is an agent which indirectly modulates the effects of an agonist or inverse agonist at a receptor. Allosteric modulators bind to a site distinct from that of the orthosteric agonist binding site. Generally allosteric modulators induce a conformational change within the protein structure of the receptor. A "positive allosteric modulator" (PAM) induces an amplification of the orthosteric agonist's effect, either by enhancing the binding affinity or the functional efficacy of the orthosteric agonist for the target receptor. Accordingly, the compounds of the invention are expected to potentiate the effect of AMPA receptors when endogenous glutamate is released. The compounds of the invention have little or no effect upon channel currents per se and are only able to enhance ion flux through the receptor in the presence of the endogenous glutamate ligand. Accordingly, a compound of the invention may potentiate AMPA receptors by, for example, (i) slowing the rate at which the receptor desensitizes in the continued presence of glutamate; and/or (ii) slowing the rate at which the receptor deactivates after removal of glutamate; and/or (iii) enhancing or prolonging glutamatergic synaptic currents, thereby promoting synaptic transmission and plasticity (e.g. long-term potentiation (LTP) of synapses). Preferred compounds potentiate AMPA receptor effects (e.g. enhancing cognition) without significantly corrupting spatial and temporal information.

Compounds of the invention are thought to bind on the twofold axis of the GluA2 ligand binding domain (LBD) dimer which is formed by residues that act as 'hinges' between the two structural domains of each LBD. Modulators binding at this site may act to slow receptor deactivation by stabilizing the clamshell dimer in its closed cleft glutamate bound conformation and/or slow desensitization by stabilizing the dimer interface (Ward et al., British Journal of Pharmacology, 2010, 160 181-190).

Activation of the AMPA receptor by glutamate opens the pore of the ion channel permitting the inward flow of sodium, resulting in the depolarization of the neuronal membrane. This change in the intracellular charge releases the $Mg^{2+}$ cation from the N-methyl-D-aspartate (NMDA) receptor channel, permitting passage of $Ca^{2+}$ through the NM DA receptor pore into the postsynaptic neurone and triggering $Ca^{2+}$-dependent signal transduction cascades, trafficking of extra-synaptic AMPA receptors and high conductance GluA1 homomers to the postsynaptic density, leading to the induction of forms of synaptic plasticity (Passafaro et al.; Subunit-specific temporal and spatial patterns of AMPA receptor exocytosis in hippocampal neurons. Nat Neurosci 2001, 4, 917-926).

The potentiation of AMPA receptors by the compounds of the invention may be assessed by measuring calcium ion influx via AMPA receptors upon exposure of the receptor to glutamate in the presence of a test compound. One such assay is the calcium ion influx assay described in the Examples using cells which express human GluR2 flip (GluA2 flip) AMPA receptor subunits which form functional homotetrameric AMPA receptors. The GluA2 flip sub-units are highly expressed in cortical and sub-cortical brain tissue (Ward et al., 2010, ibid). The Examples show that the compounds of the invention are potent potentiators of AMPA receptors in the presence of the glutamate ligand.

The effects of a compound of the invention in-vitro could also be determined using human inducible pluripotent stem cell (iPSC)-derived glutamate neurons (e.g. iCell® GlutaNeurons ex. Cellular Dynamics International) using multielectrode array electrophysiology. An analogous method is described in Dage et al., (pharmacological characterisation of ligand- and voltage-gated ion channels expressed in human iPSC-derived forebrain neurons, Psychopharmacology. 2014, 231(6):1105-1124).

The compounds of the invention are expected to enhance cognition. The effect on cognition can be assessed in-vivo using known models of behavioural cognition. For example, a novel object recognition (NOR) model as described in Ennaceur et al., (Behav. Brain Res. 1988, 31, 47-59). The test relies on a rat's natural tendency to explore novelty and involves two trials. In the first (T1) the rat is exposed to two identical objects for a brief period of time (3 min). After a delay (inter trial interval: ITI), the rat is placed back in the chamber with one of the familiar objects it encountered in the first phase and an additional novel object (T2). Rodents typically spend more time exploring the novel object over the familiar object, which is interpreted as reflecting the rodent's memory for the familiar object and its desire to explore a novel object. Because the task relies on the rodent's preference for novelty, it does not require any rule learning and hence no pre-training. Task difficulty can be increased by increasing the delay between T1 and T2. In a variant of this method memory loss in the rat can be induced using a pharmacological agent, for example sub-chronic phencyclidine, instead of the intertrial interval (ITI) time delay. Certain of the compounds exemplified herein have been tested in the NOR model and exhibited a minimum effective dose in the NOR test of less than 10 mg/kg, when administered orally.

Suitably the compounds of the invention provide a wide therapeutic window between the desirable pro-cognitive effects and undesirable side-effects, particularly pro-convulsive effects which may result from over-activation of AMPA receptors.

The potential for a compound to induce convulsive effects may be determined using a variety of models. For example, in-vitro pro-convulsant liability may be assessed using rodent neuronal electrophysiology hippocampus slices to assess potentially convulsive effects of a compound at different concentrations. The liability of a compound to induce repetitive firing being an in-vitro surrogate of convulsant activity.

Potential pro-convulsant effects in-vivo may be assessed using for example a maximum electroshock threshold (MEST) test. In the MEST test, corneal application of electrical current (CC of approximately 60-70 mA, 0.1 ms duration) in the rat induces tonic and full tonic-clonic seizures. In order to assess the potential of a compound to reduce seizure threshold activity, rats are pre-treated with compound, saline vehicle, or picrotoxin as a positive control 30 min before testing. Models for assessing the convulsant effects of compounds are known and described in, for example Ward et al., J. Med. Chem. 2011, 54, 78-94, and Loscher et al., Epilepsy Res. 1991, 8: 79-84.

Suitably the compound of the invention does not show any pro-convulsant activity in the MEST test at doses which are at least 50 times greater than the minimum efficacious dose in the NOR test. For example, no pro-convulsive effects are observed in the MEST test at doses which are greater than 75 times, or preferably greater than 100 times the minimum efficacious dose in the NOR test.

The compounds of the invention suitably have a favourable drug metabolism and pharmacokinetic (DMPK) profile, for example low clearance, high oral bioavailability, high brain penetration and a half-life providing a reasonable duration of action following dosing of the compound.

Suitably the compounds of the invention exhibit a low in-vitro intrinsic clearance (CLi) in the presence of rat, dog and/or human liver microsomes. For example, compounds of the invention preferably have a CLi of less than 100 μL/min/kg in rat and human microsomes. The CLi can be measured using known methods, such as those illustrated in the Examples.

Human P-glycoprotein (P-gp, MDR1) is highly expressed in the blood brain barrier and poses a barrier to brain penetration for P-gp substrates. Compounds with a high P-gp efflux liability may exhibit low penetration of the blood-brain barrier resulting in low, possibly sub-therapeutic, brain concentration of the compound.

Suitably compounds of the invention exhibit an efflux ratio of less than 5, preferably less than 2 when measured in an efflux assay using Madin-Darby canine kidney (MDCK) cell line transfected with human MDR1 as described in Feng et al., Drug Metabolism and Disposition, The American Society for Pharmacology and Experimental Therapeutics, Vol 36 (2), 2008, 268-275. Compounds of the invention suitably exhibit a high membrane permeability in, for example the PAMPA, assay described in Feng et al.

The biological properties of the compounds may be assessed using the methods described herein including the Examples. The properties of the compounds may also be assessed using the methodology and screening cascade described in Ward et al., 2010 ibid, for example FIG. 6 therein.

Pharmaceutical Compositions

In accordance with another aspect, the present invention provides a pharmaceutical composition comprising a compound of the invention and a pharmaceutically acceptable excipient.

Conventional procedures for the selection and preparation of suitable pharmaceutical compositions are described in, for example, "Pharmaceuticals—The Science of Dosage Form Designs", M. E. Aulton, Churchill Livingstone, 1988; and Remington: The Science and Practice of Pharmacy, 20th Edition, Lippincott, Williams and Wilkins, 2000.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing). Suitably the compound of the invention is administered orally, for example in the form of a tablet, capsule, granule or powder dosage form.

The compositions of the invention may be obtained by conventional procedures using conventional pharmaceutical excipients, well known in the art. Thus, compositions intended for oral use may contain, for example, one or more fillers, binders, colouring, sweetening, flavouring and/or preservative agents. Pharmaceutical excipients suitable for the preparation of dosage forms are well known, for example as described in the Handbook of Pharmaceutical Excipients, Seventh Edition, Rowe et al.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients, which may vary from about 5 to about 98 percent by weight of the total composition.

Therapeutic Uses and Applications

The Background section herein provides information on the potentiation of AMPA receptors and the potential therapeutic benefits expected to arise therefrom. It is to be understood that this disclosure is also considered to be part of the Detailed Description of the Invention.

The compounds of the invention potentiate AMPA receptors. Accordingly, a compound of the present invention for use in the treatment of a condition which is modulated by an AMPA receptor.

Suitably the compound of the invention is for use in the treatment of a condition in which AMPA receptor function is impaired. Accordingly, the compound of the invention may be for use in the treatment of a condition in which potentiation of an AMPA receptor is beneficial.

Suitably a compound of the invention is for use in the treatment of a condition in which glutamatergic neurotransmission is dysfunctional. Accordingly, it may be that a compound of the invention is for use in the treatment of a neurological or psychiatric condition associated with glutamate dysfunction. Such glutamatergic disorders are known and include one or more of the conditions described herein.

It may be that the compound of the invention is for use in the treatment of cognitive dysfunction. Cognitive dysfunction may arise as a result of, for example, ageing or as an effect of a disease or condition. In particular a compound of the invention may be for use in the treatment of cognitive dysfunction associated with a neuropsychiatric disease. It may be that a compound of the invention is for use in the treatment of conditions where long-term potentiation (LTP or synaptic plasticity) has been impaired, for example in the treatment of Huntington's disease, e.g. to improve synaptic plasticity and/or memory in a subject with Huntington's disease.

It may be that the compound of the invention is for use in the treatment or prevention central nervous system (CNS) disorders associated with an alteration in one or more of cognitive function, synaptic plasticity, or an imbalance in excitatory/inhibitory neurotransmission.

It may be that the compound of the invention is for use in the treatment of cognitive dysfunction associated with a neurological disorder or a neuropsychiatric condition, for example cognitive dysfunction associated with a glutamatergic disorder.

Reference to "cognitive dysfunction" or "cognitive impairment" are used interchangeably herein and refer to a loss or impairment of intellectual functions, including but not limited to one or more of memory, reasoning, problem solving, verbal recall, concentration, attention, speed of processing, executive function, social cognition, verbal learning, visual learning and perception.

A compound of the invention may be for use in the treatment of cognitive impairment, for example impairment of attention, orientation, memory, memory disorders, amnesia, amnesic disorders, age related cognitive impairment, age-associated memory impairment, language function learning disorders and attention disorders.

AMPA receptor modulators have been shown to be beneficial in pre-clinical models of other diseases, for example, depressive disorders (Quirk et al.: a novel positive allosteric modulator of AMPA receptors; CNS Drug Rev., 2002, 8, 255-282; and O'Neill et al., AMPA receptor potentiators: application for depression and Parkinson's disease; Curr. Drug Targets, 2007, 8, 603-620); Huntington's disease (Simmons et al., Up-regulating BDNF with an ampakine rescues synaptic plasticity and memory in Huntington's disease knockin mice. Proc. Natl. Acad. Sci. USA, 2009, 106, 4906-4911); stroke (Dicou et al., Positive allosteric modulators of AMPA receptors are neuroprotective against lesions induced by an NMDA agonist in neonatal mouse brain. Br. Res, 2003, 970, 221-225) and Parkinson's disease (Bloss et al., Behavioural and biological effects of chronic S18986, a positive AMPA receptor modulator, during aging. Exp Neurol., 2008, 210: 109-117).

A compound of the invention may be for use in the treatment of one or more of the conditions listed below, for example those listed in the 5 bullet points below. In some embodiments a compound of the invention may be for use in the treatment of one or more of enhancing cognitive function and/or synaptic plasticity and/or an imbalance in excitatory/inhibitory neurotransmission cognitive impairment associated with one or more of the following conditions:

psychosis and psychotic disorders, for example schizophrenia, schizo-affective disorder, schizophreniform diseases, brief reactive psychosis, child onset schizophrenia, "schizophrenia-spectrum" disorders such as schizoid or schizotypal personality disorders, acute psychosis, alcohol psychosis, drug-induced psychosis, autism (including Asperger's disorder and Rett's disorder), delirium, mania (including acute mania), manic depressive psychosis, hallucination, endogenous psychosis, organic psychosyndrome, paranoid and delusional disorders, puerperal psychosis, and psychosis associated with neurodegenerative diseases such as Alzheimer's disease;

substance related disorders; for example, selected from substance abuse substance dependence, substance intoxication, substance withdrawal, alcohol-related disorders, amphetamine related disorders, cannabis related disorders, cocaine related disorders, and nicotine-related disorders, opioid related disorders (for example opioid dependence, opioid abuse, opioid intoxication, opioid withdrawal or opioid induced psychotic disorder);

neurodegenerative diseases, for example selected from Alzheimer's disease; amyotrophic lateral sclerosis; motor neurone disease; motor disorders; Parkinson's disease; dementia in Parkinson's disease; dementia in Huntington's disease; neuroleptic-induced Parkinsonism and tardive dyskinesias; neurodegeneration following stroke, cardiac arrest, pulmonary bypass, traumatic brain injury, spinal cord injury or perinatal hypoxia; and demyelinating diseases such as multiple sclerosis and amyotrophic lateral sclerosis;

depression, for example bipolar depression (including type I and type II), unipolar depression, single or recurrent major depressive episodes with or without psychotic features, catatonic features, melancholic features, atypical features (e.g. lethargy, over-eating/obesity, hypersomnia) or postpartum onset, seasonal affective disorder and dysthymia, depression-related anxiety, psychotic depression; and a disorder selected from post-traumatic stress syndrome, attention deficit disorder, attention deficit hyperactivity disorder, drug-induced disorders (for example disorders induced by phencyclidine, ketamine, opiates, cannabis, amphetamines, dissociative anaesthetics, amphetamine, cocaine and other psychostimulants); Huntingdon's chorea; tardive dyskinesia; dystonia; myoclonus; spasticity; obesity; stroke; sexual dysfunction; sleep disorders including narcolepsy and other conditions resulting from sleep disorder; migraine; trigeminal neuralgia, hearing loss; tinnitus, ocular damage, retinopathy, macular degeneration; and pain (including acute and chronic pain, severe pain, intractable pain, neuropathic pain, and post-traumatic pain).

In embodiments a compound of the invention is for use in the treatment of cognitive impairment associated with any of the conditions listed above. For example a compound of the invention may be for use in the treatment of cognitive impairment associated with or resulting from stroke, Alzheimer's disease, Huntington's disease, Pick disease, Aids-related dementia, Multiinfarct dementia, alcoholic dementia, hypothyroidism-related dementia, and dementia associated to other degenerative disorders such as cerebellar atrophy and amyotrophic lateral sclerosis, delirium, depression trauma, head trauma, aging, neurodegeneration, drug-induced states, neurotoxic agents, autism, Down's syndrome, psychosis, post-electroconvulsive treatment; anxiety disorders (including generalised anxiety disorder, social anxiety disorder, agitation, tension, social or emotional withdrawal in psychotic patients, panic disorder and obsessive compulsive disorder), substance-induced persisting dementia, substance-induced persisting amnesic disorder or substance induced psychotic disorder.

Accordingly one embodiment provides a compound of the invention for use in the treatment of a neurological or neuropsychiatric disease or condition. For example, a compound of the invention may be for use in the treatment of Alzheimer's disease, Parkinson's disease, Huntington's disease, Amyotrophic Lateral Sclerosis, schizophrenia, obsessive-compulsive disorder, addiction and mood disorders (including major depressive disorders and bipolar disorder). Particularly the compound of the invention may be for use in the treatment of cognitive dysfunction associated with any such condition.

In a particular embodiment there is provided a compound of the invention for use in the treatment of schizophrenia. For example, a compound of the invention may be for use in the treatment a subtype of schizophrenia selected from paranoid type, disorganised type, catatonic type, undifferentiated type and residual type schizophrenia.

The assessment of the cognitive effects of the compounds in humans suffering from schizophrenia can be assessed using known methods, for example using the MATRICS Consensus Cognitive Battery (MCCB) is a standardized battery for use with adults with schizophrenia (Buchanan et al., A summary of the FDA-NIMH-MATRICS workshop on clinical trial design for neurocognitive drugs for schizophrenia. Schizophr. Bull. 2005; 31(1):5-19).

Depressive Disorders

As disclosed in the Background section ketamine has been shown to be effective in the treatment of depression and that the effects of ketamine are attributable to AMPA receptor potentiation by a metabolite of ketamine (see e.g. Zanos 2016 ibid). Accordingly, compounds of the invention are expected to be useful in the treatment of depressive disorders, particularly major depressive disorders.

Major depressive disorder (MDD) (also known as clinical depression, major depression, unipolar depression, unipolar disorder or recurrent depression) is defined in the International Statistical Classification of Diseases and Related Health Problems (ICD-10) as a mental disorder characterized by a pervasive and persistent low mood that is accompanied by low self-esteem and by a loss of interest or pleasure in normally enjoyable activities. Depressive disorders also include milder forms of depression, including for example mood-disorders. The depressive disorder may be a hereditary depressive disorder and/or a depressive disorder induced by reaction to environmental or biological stress factors, for example, acute life events, childhood exposure to adversity or stress caused by the signs or symptoms of a medical condition, for example depression that arises from pain in a subject. Depressive disorders may also be associated with or caused by other medical conditions, for example, psychotic disorders, cognitive disorders, eating disorders, anxiety disorders or personality disorders. The depressive disorder may be an acute depressive disorder, a recurrent depressive disorder or a chronic depressive disorder.

In embodiments a compound of the invention is for use in the treatment of a depressive disorder selected from major depressive disorder, dysthymic disorder (persistent depressive disorder), atypical depression, melancholic depression, psychotic depression, catatonic depression, postpartum depression (PPD), premenstrual syndrome, premenstrual dysphoric disorder (PMDD), seasonal affective disorder (SAD), double depression, depressive personality disorder (DPD), recurrent brief depression (RBD), minor depressive disorder, bipolar disorder, bipolar depression, substance/medication-induced depressive disorder (including alcohol-induced and benzodiazepine-induced), post-schizophrenic depression and a depressive disorder caused by or associated with another medical condition (e.g. depressions caused by or associated with a dementia, metabolic disorder, multiple sclerosis, cancer, chronic pain, chemotherapy and/or chronic stress. In some embodiments a compound of the invention is for use in the treatment of a depressive disorder which has an associated anxious component or anxiety disorder. For example, the treatment of a depressive disorder described herein with an associated anxiety disorder as described herein (e.g. selected from a panic disorder, panic disorder with agoraphobia, a social phobia, a specific phobia (e.g. an animal or environmental phobia), post-traumatic distress disorder, an acute stress disorder, an obsessive compulsive disorder (OCD) and panic attacks).

In some embodiments a compound of the invention is for use in the treatment of a mood disorder. Mood disorders are conditions in which a patient's mood changes to depression (often with associated anxiety) and/or to elation. The mood disorders may be acute or recurrent and are often triggered by stressful events or situations. Examples of mood disorders include, manic episodes (e.g. hypomania, mania with psychotic symptoms or mania without psychotic symptoms); a bipolar affective disorder (e.g. manic depression or a manic depressive illness, psychosis or reaction); a depressive episode (e.g. mild, moderate or severe depressive episode); a recurrent depressive disorder; a persistent mood disorders (e.g. cyclothymia or dysthymia); or anhedonia.

Various symptoms are associated with depressive disorders and mood disorders such as MDD, for example, persistent anxious or sad feelings, feelings of helplessness, hopelessness, pessimism, worthlessness, low energy, restlessness, irritability, fatigue, loss of interest in pleasurable activities or hobbies, excessive sleeping, over-eating, appetite loss, insomnia, thoughts of suicide, and suicide attempts. The presence, severity, frequency, and duration of these symptoms vary on a case to case basis. In some embodiments, a patient may have at least one, at least two, at least three, at least four, or at least five of these symptoms.

The effect of a compound of the invention on a depressive disorder or mood disorder may be assessed using known methods. Suitable in-vivo models of depression include for example the animal models described in Zanos et al 2016 ibid including the learned helplessness assay and female urine sniffing test after chronic mild stress. In human the effect of a compound on depressive or mood disorders may be assessed by, for example, an improvement in a patient's symptoms using a suitable clinical scoring or rating system such as a depression symptoms rating scale. Reference to a "depression symptoms rating scale" refers to any one of a number of standardized questionnaires, clinical instruments, or symptom inventories utilized to measure symptoms and symptom severity in depressive disorders. Such rating scales are often used in clinical studies to define treatment outcomes, based on changes from the study's entry point(s) to endpoint(s). Examples of depression symptoms rating scales include, but are not limited to, The Quick Inventory of Depressive-Symptomatology Self-Report (QIDS-SRi6), the 17-Item Hamilton Rating Scale of Depression (HRSDn), the 30-Item Inventory of Depressive Symptomatology (IDS-C30), The Montgomery-Åsberg Depression Rating Scale (MADRS), or The Beck's Depression Scale Inventory. Such ratings scales may involve patient self-report or be clinician rated.

Generally, a 50% or greater reduction in a depression ratings scale score over the course of a clinical trial (starting point to endpoint) is often considered to be a favourable response for most depression symptoms rating scales, although lower % reductions may provide a benefit and are contemplated herein. Generally, "remission" in clinical studies of depression refers to achieving at, or below, a particular numerical rating score on a depression symptoms rating scale (for instance, less than or equal to 7 on the HRSD17; or less than or equal to 5 on the QIDS-SRie; or less than or equal to 10 on the MADRS).

In some embodiments, a compound of the invention is for use in the treatment of a depressive condition or mood disorder (e.g. as described herein), wherein the compound provides a rapid effect on the depressive condition or mood disorder. For example, wherein the compound of the invention provides a clinically meaningful effect on the condition or disorder within 1, 2, 3, 4, 6, 8, 12, 24 or 36 hours after administration of the compound to a subject. The clinical effect of the compound may be assessed using a suitable depression symptoms rating scale.

In some embodiments, a compound of the invention is for use in the treatment of a depressive condition or mood disorder (e.g. as described herein), wherein the compound provides a sustained effect on the condition or disorder following administration of the compound to subject. For example, wherein the compound provides a clinically meaningful effect on the condition or disorder which persists 1 week, 2 weeks, 3 weeks, 4 weeks, 6 weeks, 8 weeks or 12 weeks after administration of the compound to a subject. The clinical effect of the compound may be assessed using a suitable depression symptoms rating scale.

In some embodiments a compound of the invention is for use in the treatment of a treatment resistant depressive disorder. In this embodiment the depressive disorder may be any of the depressive disorders described herein.

Treatment resistant depression (TRD), sometimes referred to as refractory depression, occurs in subjects suffering from a depressive disorder who are non-responsive or poorly responsive to one or more, standard pharmacological treatments for the depressive disorder. Examples of standard pharmacological treatments for the depressive disorder including tricyclic antidepressants, monoamine oxidase inhibitors (MAOIs), selective serotonin reuptake inhibitors (SSRIs), serotonin-norepinephrine reuptake inhibitors (SNRIs), ketamine, esketamine or other NMDA modulators, double and triple uptake inhibitors, anxiolytic drugs, atypical anti-depressants and/or anti-psychotic treatments. TRD may also occur in subjects with a depressive disorder who are poorly responsive or non-responsive to one or more non-pharmacological treatments of the depressive disorder (e.g. psychotherapy, electroconvulsive therapy, vagus nerve stimulation and/or transcranial magnetic stimulation).

A treatment resistant-subject may be identified as one who fails to experience alleviation of one or more symptoms of depression (e.g. persistent anxious or sad feelings, feelings of helplessness, hopelessness, pessimism) despite undergoing one or more, preferably 2 or more standard pharmacological or non-pharmacological treatment, such as two, three or four different antidepressant drugs. A treatment-resistant subject may also a subject that does not experience a 50% reduction in depressive symptoms after 2 courses of a standard pharmacological treatment for the depressive disorder.

Suicide Ideation

In some embodiments, a compound of the invention is for use in the treatment of suicide ideation. Suicidal behaviour is one of the leading causes of injury and death worldwide. Suicide ideation, or suicidal thoughts, is often association with or caused by depressive disorders and mood disorders.

Accordingly, in certain embodiments there is provided a compound of the invention for use in the treatment or prevention of suicide ideation. It may be that a compound of the invention is for use in the treatment or prevention of suicide ideation in a subject with a depressive disorder or a mood disorder. Examples of depressive conditions or mood disorders are as described herein.

The effects of a compound of the invention may be assessed using a suitable clinical scoring system, for example a suitable suicidal ideation rating scale for the measurement of the severity of suicide ideation. Such suicidal ideation symptoms rating scales include, but are not limited to, Scale for Suicidal Ideation (SSI), the Suicide Status Form (SSF), or the Columbia Suicide Severity Rating Scale (C-SSRS).

Anxiety

In embodiments, a compound of the invention is for use in the treatment of an anxiety disorder. Anxiety is a feeling of apprehension or fear that lingers due to an individual's perception of persistent and unrelenting stress. Anxiety is typically accompanied by various physical symptoms including twitching, trembling, muscle tension, headaches, sweating (e.g., night sweats), dry mouth, or difficulty swallowing. Some people also report dizziness, a rapid or irregular heart rate, shortness of breath, increased rate of respiration, fatigue, nausea, diarrhoea, or frequent need to urinate when they are anxious. Fatigue, irritable mood, sleeping difficulties, decreased concentration, sexual problems, or nightmares are also common. Some people are more sensitive to stress and are thus more likely to develop anxiety disorders. The propensity to succumb to anxiety attacks may be due to genetic predisposition or by previous (e.g. childhood) exposure to certain stresses. Anxiety may also be induced by or associated with medical conditions, for example pain, especially in patients suffering with chronic pain.

Examples of anxiety disorders include separation anxiety disorder, selective mutism, specific phobia, social anxiety disorder (social phobia), panic disorder, panic attack, agoraphobia, post-traumatic stress disorders (PTSD), generalized anxiety disorder, substance/medication-induced anxiety disorder, anxiety disorder due to another medical disorder (e.g. depression), other specified anxiety disorder, or unspecified anxiety disorder. As mentioned above the anxiety disorder may be associated with or be caused by a depressive disorder.

The effect of a compound if the invention in the treatment of an anxiety disorder may be assessed using a suitable anxiety symptom rating scale. Such scales are well-known and include, for example standardized questionnaires, clinical instruments, or symptom inventories utilized to measure symptoms and symptom severity in anxiety. Examples of anxiety symptoms rating scales include, but are not limited to, State-Trait Anxiety Inventory (STAI), the Hamilton Anxiety Rating Scale (HAM-A), the Beck Anxiety Inventory (BAI), and the Hospital Anxiety and Depression Scale-Anxiety (HADS-A). Such ratings scales may involve patient self-reporting or be clinician rated. Generally, a 50% or greater reduction in an anxiety ratings scale score over the course of a clinical trial (starting point to endpoint) is typically considered a favourable response, although lower reductions may also be beneficial and are contemplated.

The effects of a compound of the invention in the treatment of a depressive disorders, mood disorders and anxiety disorders may also be assessed using suitable pre-clinical models. For example, in a forced swim test in rodent; a novelty-suppressed feeding model, a learned helplessness model or a chronic mild stress and social interaction model. Such models are well-known and described in for example, Wang et al The Recent Progress in animal models of depression Prog. Neuro-Psychopharm. Biol Psych. 2017 vol. 77, 99-109; Duman, Vit. Horm. 2010 vol. 82, 1-21 or WO 2017/165877.

Respiratory Depression

AMPA receptor potentiators have been found to be useful in the treatment of respiratory depression in preclinical models (Dai et al; A brain-targeted ampakine compound protects against opioid-induced respiratory depression. Eur. J. Pharmacol, 2017, 809:122-9). Accordingly, in another embodiment there is provided a compound of the invention for use in the treatment or prevention of respiratory depression in a subject. For example, a compound of the invention may be for use in the treatment of respiratory depression wherein the respiratory depression is associated with the effect of alcohol, an opiate, an opioid (e.g. fentanyl), or a barbiturate on the subject. In another embodiment a compound of the invention is for use in the treatment or prevention of respiratory depression associated with a condition associated with central sleep apnea, stroke-induced central sleep apnea, obstructive, sleep apnea resulting from Parkinson's disease, congenital hypoventilation syndrome, sudden infant death syndrome, Retts syndrome, Cheney-Stokes respiration, Ondines Curse, spinal muscular atrophy, amyotrophic lateral sclerosis, Prader-Willi's syndrome, spinal cord injury, traumatic brain injury or drowning.

Also provided is a method of treating any of the foregoing conditions in a subject in need thereof by administering an effective amount of a compound of the invention to the subject.

Also provided in the use of a compound of the invention for the manufacture of a medicament for the any of the foregoing conditions.

An effective amount of a compound of the present invention for use in therapy of a condition is an amount sufficient to symptomatically relieve in a subject, particularly a human, the symptoms of the condition or to slow the progression of the condition.

Reference to a "subject" or "patient" herein refers to, for example a warm-blooded mammal, for example a human, non-human primate, cow, horse, pig, goat, sheep, dog, cat, rabbit, mouse or rat. Preferably the subject is a human.

The size of the dose for therapeutic or prophylactic purposes of a compound of the invention will naturally vary according to the nature and severity of the conditions, the age and sex of the animal or patient and the route of administration, according to well-known principles of medicine.

In using a compound of the invention for therapeutic or prophylactic purposes it will generally be administered so that a daily dose in the range, for example, a daily dose selected from 0.001 mg/kg to 20 mg/kg, 0.005 mg/kg to 15 mg/kg or 0.01 mg/kg to 10 mg/kg body weight is received, given if required in divided doses. In general, lower doses will be administered when a parenteral route is employed. Thus, for example, for intravenous or intraperitoneal administration, a dose in the range, for example, 0.001 mg/kg to 1 mg/kg body weight will generally be used. The daily dose administered orally may be, for example a total daily dose selected from 0.1 mg to 1000 mg, 0.5 mg to 1000 mg, 1 mg to 500 mg or 1 mg to 250 mg. Typically, unit dosage forms will contain about 0.1 mg to 1000 mg, preferably about 0.5 mg to 500 mg of a compound of this invention.

Combinations

The compound of the invention can be administered alone or can be co-administered together with another therapeutic agent to a subject. The compounds of the invention can be used in co-administered with one or more other active drugs known to be useful in treating a disease (e.g. a drug useful in the treatment of one of the diseases or conditions described herein such as a CNS condition).

By "co-administer" it is meant that a compound of the invention is administered at the same time, prior to, or after the administration of one or more additional therapeutic agent. Co-administration is meant to include simultaneous or sequential administration of the compound and the additional therapeutic agent. Thus, the compound of the invention can be combined, when desired, with other therapeutic agents. For simultaneous administration, the compound of the invention and the therapeutic agent may comprise a single pharmaceutical composition. Alternatively, the compound of the invention and the additional therapeutic agent may be comprised in two separate pharmaceutical compositions, which may be administered to the subject simultaneously or sequentially.

The compound of the invention and the one or more additional therapeutic agent may be administered to the subject using the same route of administration or by different routes of administration. For example, the compound of the invention and additional therapeutic agent may be administered orally as a single pharmaceutical composition or as two separate compositions. Alternatively, the compound of the invention may be administered to the subject orally and the therapeutic agent may be administered by a different route of administration, e.g. parenterally. The administrations to the subject may occur substantially simultaneously or sequentially.

Co-administration includes administering one active agent within 0.5, 1, 2, 4, 6, 8, 10, 12, 16, 20, 24, 48 hours or 1 week of a second active agent. Co-administration includes administering two active agents simultaneously, approximately simultaneously (e.g., within about 1, 5, 10, 15, 20, or 30 minutes of each other), or sequentially in any order.

Additional Therapeutic Agent

The additional therapeutic agent may be any therapeutic agent suitable for use in the treatment or prophylaxis of any of the conditions described herein. For example, when the compound of the invention is for use in the treatment of a neurological, psychiatric condition, depressive disorder or mood disorder, the compound of the invention may be co-administered with one or more additional therapeutic agents selected from include antidepressants, antipsychotics, Alzheimer's drugs and anti-anxiety agents.

Accordingly, a compound of the invention may be co-administered with one or more additional therapeutic agents selected from:

typical antipsychotics, for example chlorpromazine, thioridazine, mesoridazine, fluphenazine, perphenazine, prochlorperazine, trifluoperazine, thiothixine, haloperidol, molindone or loxapine;

atypical antipsychotics, for example clozapine, olanzapine, risperidone, quetiapine, aripiprazole, ziprasidone, amisulpride, ziprasidone, paliperidone or bifeprunox;

anticholinergics, for example benztropine, biperiden, procyclidine or trihexyphenidyl;

nicotine acetylcholine agonists, for example ispronicline, varenicline and MEM 3454;

cholinesterase inhibitors, for example donepezil and galantamine antihistamines, for example diphenhydramine;

dopaminergics, for example amantadine;

serotonin reuptake inhibitors, for example citalopram, escitalopram, fluoxetine, fluvoxamine, paroxetine, sertraline or venlafaxine;

dual serotonin/noradrenaline reuptake inhibitors (SNRIs), for example venlafaxine, desvenlafaxine, duloxetine, milnacipran or levomilnacipran;

triple reuptake inhibitors (serotonin, norepinephrine, dopamine reuptake inhibitors, SNDRIs), for example, mazindol, nefazodone or sibutramine;

noradrenaline (norepinephrine) reuptake inhibitors, for example reboxetine;

NK-1 receptor antagonists, for example aprepitant or maropitant, corticotropin releasing factor (CRF) antagonists, α-adrenoreceptor antagonists;

tricyclic antidepressants, for example amitriptyline, clomipramine, imipramine, maprotiline, nortriptyline or trimipramine, doxepin, trimipramine, dothiepin, butriptyline, iprindole, lofepramine, nortriptyline, protriptyline, amoxapine or desipramine;

monoamine oxidase inhibitors, for example isocarboxazid, moclobemide, phenelzine, selegiline, or tranylcypromine;

atypical anti-depressants, for example bupropion, lithium, nefazodone, trazodone or viloxazine;

other antidepressants, for example bupropion, mianserin, mirtazapine or trazodone;

anxiolytics, for example benzodiazepines (e.g. alprazolam or lorazepam and others below), barbiturates (e.g. secobarbital, pentobarbital, butabarbital, phenobarbital, or amobarbital);

cognitive enhancers, for example cholinesterase inhibitors (such as tacrine, donepezil, rivastigmine or galantamine;

stimulants, for example methylphenidate, amphetamine formulations or pemoline;

mood stabilisers, for example lithium, sodium valproate, valproic acid, divalproex, carbamazepine, lamotrigine, gabapentin, topiramate or tiagabine;

NMDA receptor antagonists, for example memantine, ketamine and esketamine;

benzodiazepines, for example alprazolam, chlordiazepoxide, clonazepam, chlorazepate, diazepam, halazepam, lorazepam, oxazepam or prazepam; and 5-HT1A receptor agonists or antagonists, for example buspirone, flesinoxan, gepirone and ipsapirone.

According to another aspect of the invention there is provided a compound of the invention and another therapeutic agent for use in the conjoint treatment of a condition which is modulated by an AMPA receptor.

Co-administration of a compound of the invention with another therapeutic agent may be beneficial in preventing or reducing negative side effects associated with the other therapeutic agent. For example, certain therapeutic agents may affect cognitive function in a subject. Accordingly, a further aspect of the invention provides a compound of the invention for use in the treatment of cognitive dysfunction resulting from the administration of another therapeutic agent to a subject.

In these last two embodiments the therapeutic agent may be any of the therapeutic agents other than the compound of the invention described herein, for example an anti-psychotic agent.

In a particular embodiment there is provided a compound of the invention and another therapeutic agent for use in the conjoint treatment of schizophrenia, wherein the other therapeutic agent is a typical antipsychotic (for example chlorpromazine, thioridazine, mesoridazine, fluphenazine, perphenazine, prochlorperazine, trifluoperazine, thiothixine, haloperidol, molindone or loxapine) or an atypical antipsychotic (for example clozapine, olanzapine, risperidone, quetiapine, aripiprazole, ziprasidone, amisulpride, ziprasidone, paliperidone, bifeprunox or talnetant). In this embodiment the conjoined treatment provides a treatment of cognitive impairment associated with schizophrenia.

In another embodiment there is provided a compound of the invention and an anti-depressant for use in the conjoint treatment of a depressive condition (e.g. a major depressive disorder). The anti-depressant may be any anti-depressant other than an AMPA receptor modulator of the invention. For example, a compound of the invention may be for use with an anti-depressant in the conjoined treatment of a depressive disorder, wherein the anti-depressant is selected from a tricyclic antidepressant, a monoamine oxidase inhibitor, a selective serotonin reuptake inhibitor, a serotonin-norepinephrine reuptake inhibitor, an NMDA modulator, a double or triple uptake inhibitor, an anxiolytic drug and an atypical anti-depressant.

Also contemplated is a compound of the invention and a non-pharmacological treatment of a depressive condition for use in the conjoint treatment of a depressive condition (e.g. a major depressive disorder). The non-pharmacological treatment of a depressive condition may be, for example psychotherapy, electroconvulsive therapy, vagus nerve stimulation and/or transcranial magnetic stimulation)

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

Synthesis

The skilled person will appreciate that adaptation of methods known in the art could be applied in the manufacture of the compounds of the present invention.

For example, the skilled person will be immediately familiar with standard textbooks such as "Comprehensive Organic Transformations—A Guide to Functional Group Transformations", RC Larock, Wiley-VCH (1999 or later editions), "March's Advanced Organic Chemistry—Reactions, Mechanisms and Structure", MB Smith, J. March, Wiley, (5th edition or later) "Advanced Organic Chemistry, Part B, Reactions and Synthesis", F A Carey, R J Sundberg, Kluwer Academic/Plenum Publications, (2001 or later editions), "Organic Synthesis—The Disconnection Approach", S Warren (Wiley), (1982 or later editions), "Designing Organic Syntheses" S Warren (Wiley) (1983 or later editions), "Guidebook To Organic Synthesis" R K Mackie and D M Smith (Longman) (1982 or later editions), etc., and the references therein as a guide.

The skilled chemist will exercise judgement and skill as to the most efficient sequence of reactions for synthesis of a given target compound and will employ protecting groups as necessary. This will depend inter alia on factors such as the nature of other functional groups present in a particular substrate. Clearly, the type of chemistry involved will influence the choice of reagent that is used in the said synthetic steps, the need, and type, of protecting groups that are employed, and the sequence for accomplishing the protection/deprotection steps. These and other reaction parameters will be evident to the skilled person by reference to standard textbooks and to the examples provided herein.

Sensitive functional groups may need to be protected and deprotected during synthesis of a compound of the invention. This may be achieved by conventional methods, for example as described in "Protective Groups in Organic Synthesis" by T W Greene and P G M Wuts, John Wiley & Sons Inc. (1999), and references therein.

Compounds of the formula (I) may be prepared by coupling a compound of the formula (VIII) with a compound of the formula (IX):

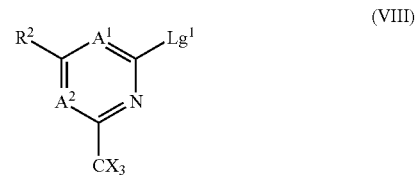

(VIII)

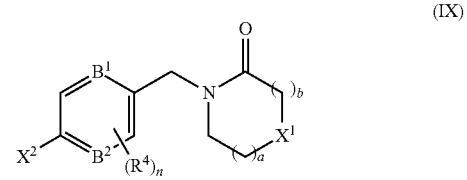

(IX)

wherein:

$Lg^1$ is halo, for example Cl;

$X^2$ is a boronic acid or an ester thereof;

$A^1$, $A^2$, $R^2$, $R^4$, $B^1$, $B^2$, X, $X^1$, n, a and b are as defined herein.

The coupling reaction is suitably carried out as a Suzuki coupling reaction in the presence of a suitable catalyst (for example a palladium or nickel catalyst) and a suitable base (e.g. an alkali metal carbonate, phosphate, alkoxide or hydroxide, or an organic amine).

The preparation of representative compounds are illustrated in Schemes 1 to 6 below.

Scheme 1
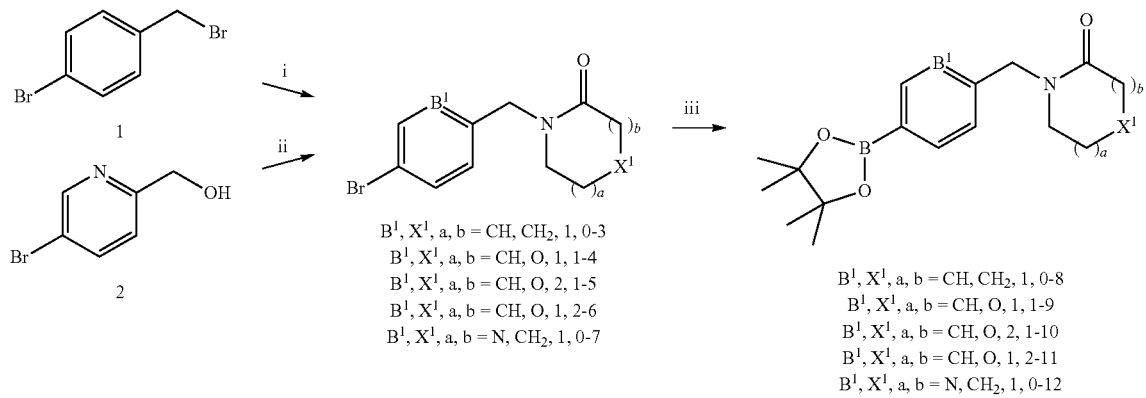
Reagents and conditions: (i) a) Amide, NaH (60% dispersion in mineral oil), DMF, 0° C., 30 min; b) (1), 0° C. to RT, 18 h, 90-99%; (ii) a) Amide, NaH (60% dispersion in mineral oil) DMF, 0° C., 30 min; b) (2), MsCl, DIPEA, DCM, 0° C. to RT, 16 h 76%; (iii) (Bpin)$_2$, KOAc, Pd(dppf)Cl$_2$, 1,4-dioxane or DMSO, 80-90° C., 4-5 h 23-95%.
Scheme 2
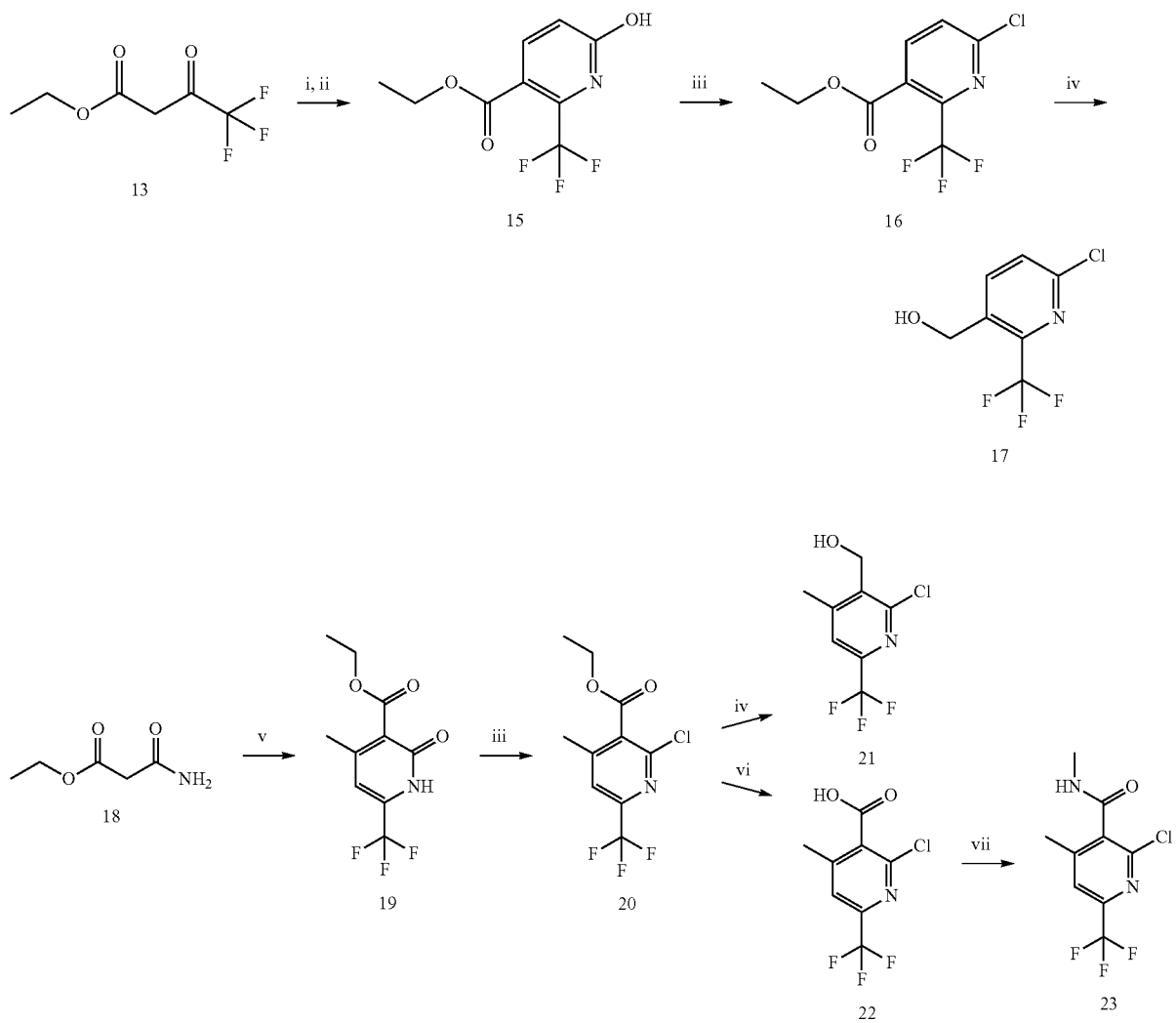

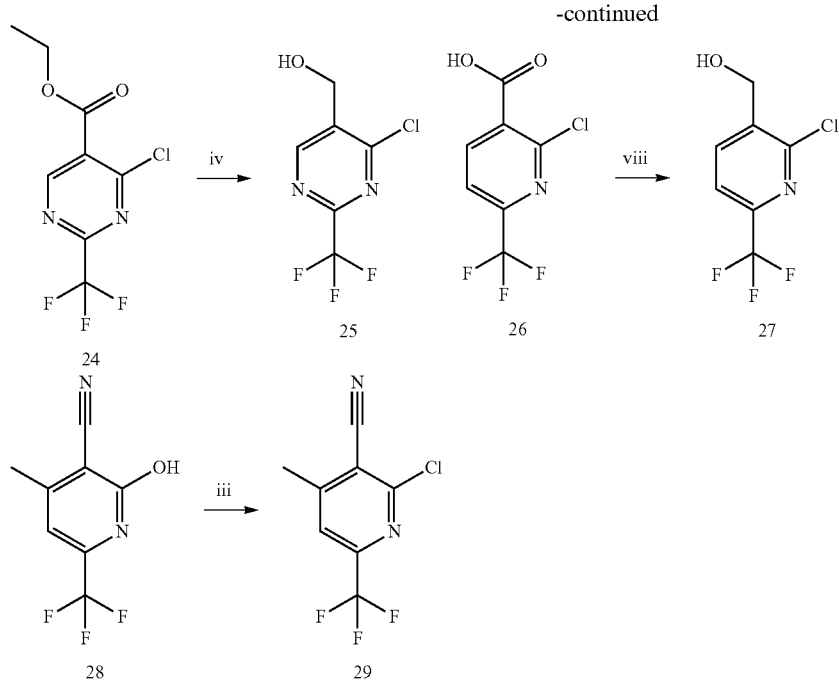

Reagents and conditions: (i) Acrylamide, pTsOH·H₂O, toluene, reflux, 48 h, 31%; (ii) NBS, CCl₄, reflux, 18 h, 32%; (iii) PhOP(O)Cl₂, 165-170° C., 30 min, 36-77%; (iv) DIBAL—H, DCM, 0° C. to RT, 18 h, 23-78%; (v) (E)-1,1,1-trifluoro-4-methoxy-pent-3-en-2-one, NaOEt, EtOH, reflux, 18 h, 73%; (vi) NaOH, THF, EtOH, 50° C., 24 h, 80%; (vii) MeNH₂, HATU, DIPEA, DMF, RT, 72 h, 26%; (viii) BH₃, THF, 0° C. to RT, 16 h, 100%.

Scheme 3

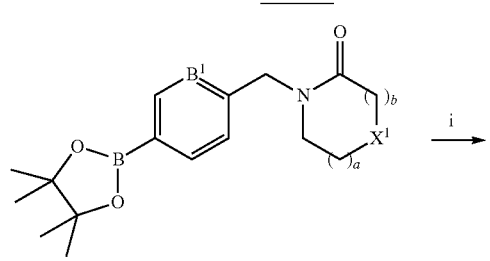

$B^1, X^1, a, b$ = CH, CH₂, 1, 0-8
$B^1, X^1, a, b$ = CH, O, 1, 1-9
$B^1, X^1, a, b$ = CH, O, 2, 1-10
$B^1, X^1, a, b$ = CH, O, 1, 2-11
$B^1, X^1, a, b$ = N, CH₂, 1, 0-12

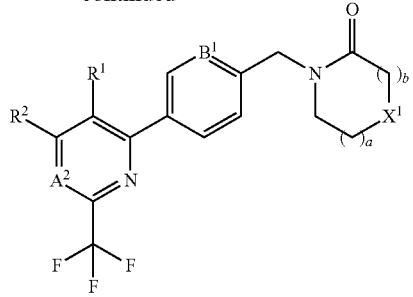

$R^1$ = H, CH₃, CN, CH₂F or C(O)NHCH₃,
$R^2$ = H or CH₃
$A^2$ = N, C—H, C—CH₃ or C—CH₂F

Reagents and conditions: (i) Ar—Cl, Pd(PPh₃)₂Cl₂ or Pd(dppf)Cl₂, Na₂CO₃, MeCN or 1,4-dioxane, H₂O, 95° C./3 h or 135-145° C./15-30 min, 29-94%; (ii) Deoxo-Fluor®, DCM, 0° C. to RT, 2-72 h, 43-98%.

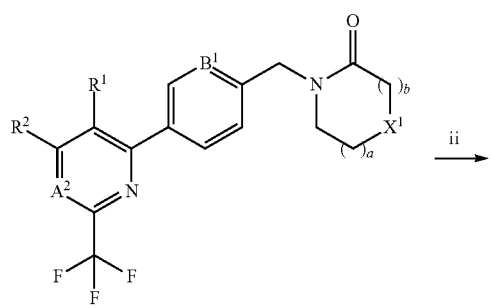

$R^1$ = H, CH₃, CN, CH₂OH or C(O)NHCH₃,
$R^2$ = H or CH₃
$A^2$ = N, C—H, C—CH₃ or C—CH₂OH

| Boronic ester | Reaction-(i) | | | Reaction-(ii) | |
|---|---|---|---|---|---|
| | Ar-Cl | Product | Yield (%) | Product | Yield (%) |
| 8 | 17 | 32 | 54 | 49 | 49 |
| 8 | 21 | 33 | 35 | 50 | 71 |
| 8 | 23 | 34 | 41 | — | — |
| 8 | 25 | 35 | 56 | 51 | 98 |
| 8 | 27 | 36 | 94 | 52 | 72 |
| 8 | 29 | 37 | 62 | — | — |
| 8 | 30 | 38 | 31 | — | — |
| 8 | 31 | 39 | 59 | — | — |
| 9 | 17 | 40 | 29 | — | — |
| 9 | 21 | 41 | 42 | 53 | 62 |
| 9 | 27 | 42 | 57 | 54 | 92 |

47
-continued

| | Reaction-(i) | | | Reaction-(ii) | |
|---|---|---|---|---|---|
| Boronic ester | Ar-Cl | Product | Yield (%) | Product | Yield (%) |
| 9 | 31 | 43 | 53 | — | — |
| 10 | 21 | 44 | 87 | — | — |
| 11 | 21 | 45 | 85 | — | — |
| 12 | 21 | 46 | 50 | 55 | 43 |
| 12 | 27 | 47 | 53 | 56 | 63 |
| 12 | 31 | 48 | 84 | — | — |

Scheme 4

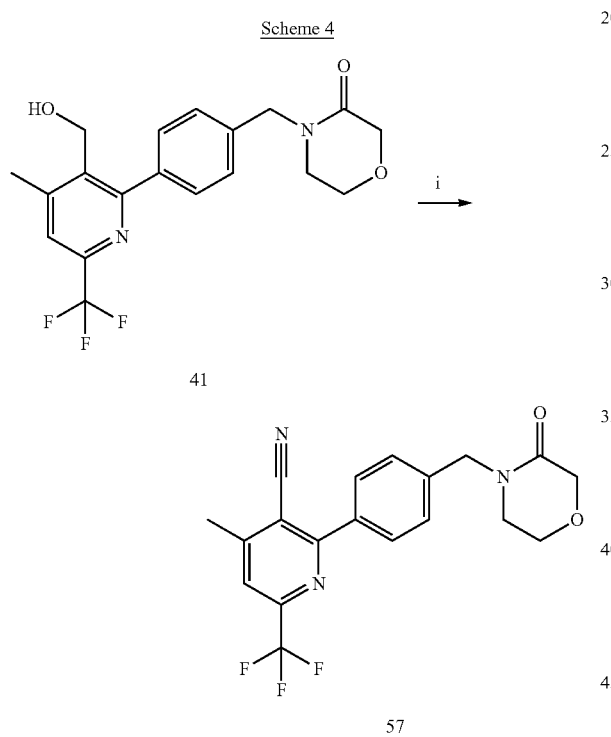

41

57

Reagents and conditions: (i) ammonium acetate, (diacetoxyiodo)benzene, TEMPO, MeCN:H₂O (9:1), RT, 18 h, 48%.

Scheme 5

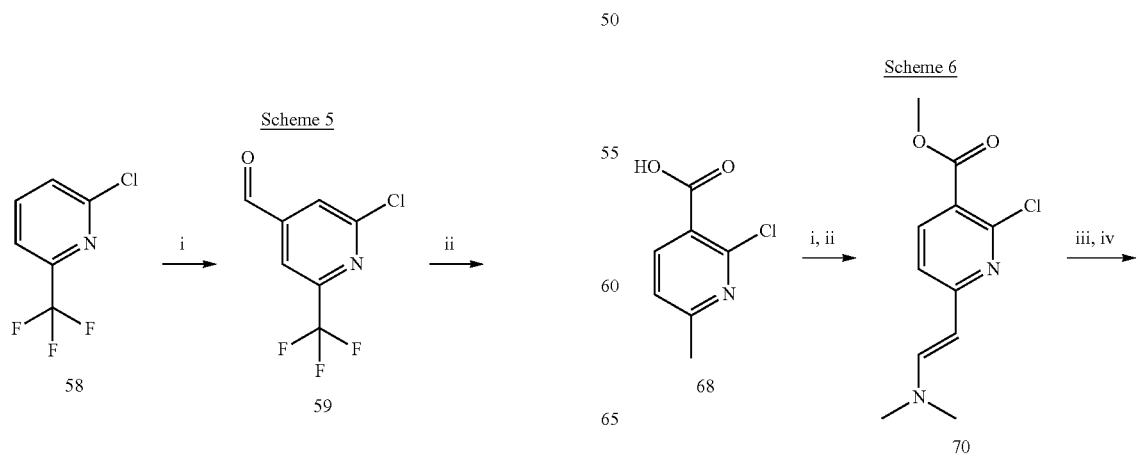

58

59

48
-continued

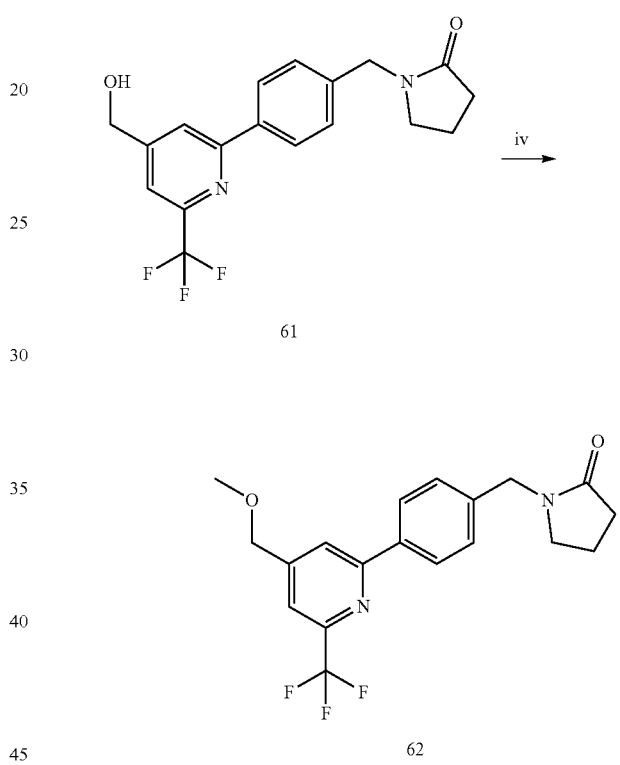

60

61

62

Reagents and conditions: (i) TMPMgCl·LiCl, DMF, THF, -78° C. to RT, 16 h, 34%; (ii) (8), Pd(PPh₃)₂Cl₂, Na₂CO₃, MeCN, H₂O, 145° C., 20 min, 48%; (iii) NaBH₄, MeOH, RT, 3 h, 25%; (iv) MeI, NaH (60% dispersion in mineral oil), THF, RT, 18 h, 56%.

Scheme 6

68

70

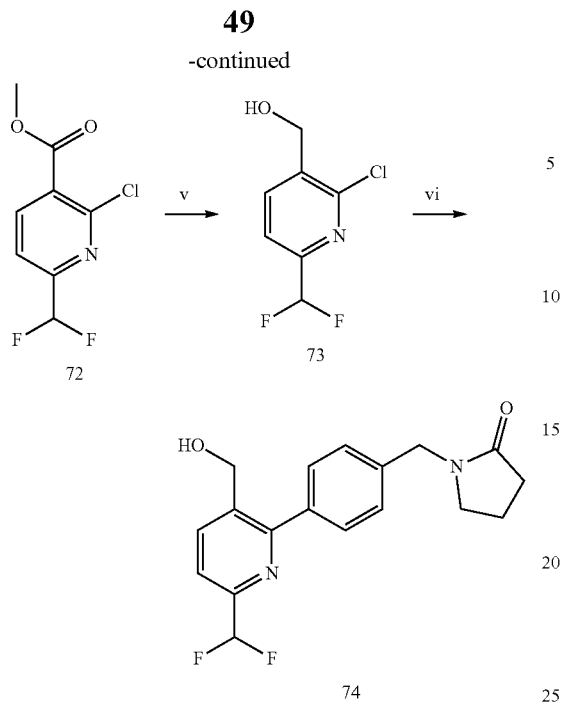

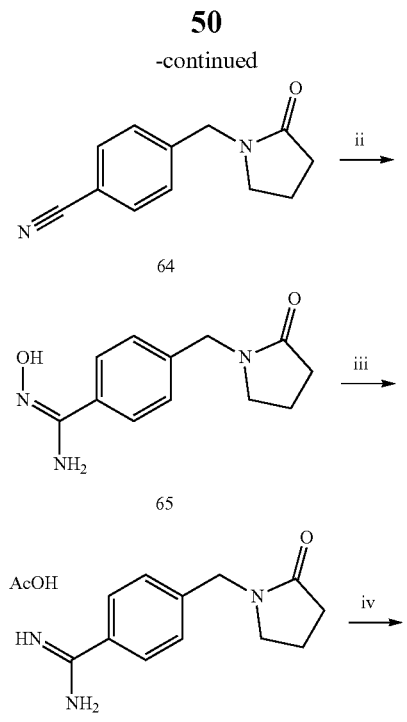

Reagents and conditions: (i) MeI, K₂CO₃, DMF, RT, 18 h, 91%; (ii) DMF—DMA, DMF, 120° C., 24 h, 86%; (iii) NaIO₄, THF, H₂O, RT, 2 h, 14%; (iv) Deoxo-Fluor®, DCM, 0° C. to RT, 16 h, 48%; (v) DIBAL—H, DCM, 0° C. to RT, 2 h, 83%; (vi) (8), Pd(PPh₃)₂Cl₂, Na₂CO₃, MeCN, H₂O, 135° C., 15 min, 49%.

Compounds of the formula (I) wherein A¹ is N may also be prepared by cyclising a compound of the formula (X) with a compound of the formula (XI):

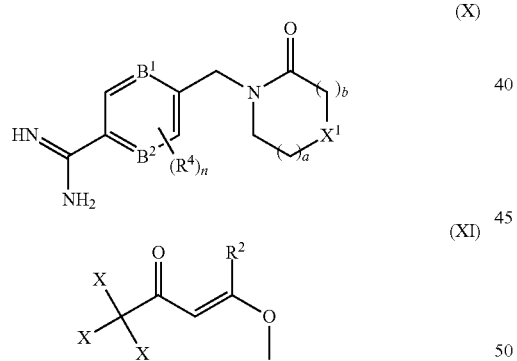

wherein R², R⁴, B¹, B², X, X¹, n, a and b are as defined herein.

Representative compounds may be prepared according to Scheme 7 below:

Scheme 7

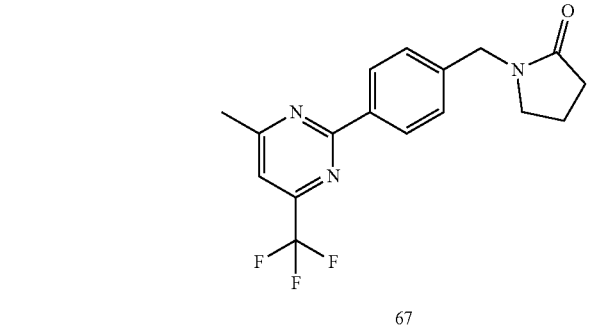

Reagents and conditions: (i) a) Pyrrolidin-2-one, NaH (60% dispersion in mineral oil), DMF, 0° C., 30 min; b) (63), 0° C. to RT, 16 h, 82%; (ii) NH₂OH·HCl, K₂CO₃, EtOH, reflux, 16 h, 76%; iii) Ac₂O, 10% Pd/C, H₂, AcOH, RT, 24 h, 84%; (iv) (E)-1,1,1-trifluoro-4-methoxy-3-penten-2-one, NaOEt, EtOH, reflux, 18 h, 74%.

Certain intermediates used in the preparation of compounds of the invention are novel and form a further feature of the invention. Accordingly, also provided is a compound of the formula (XII) or (XIII), or a pharmaceutically acceptable salt thereof:

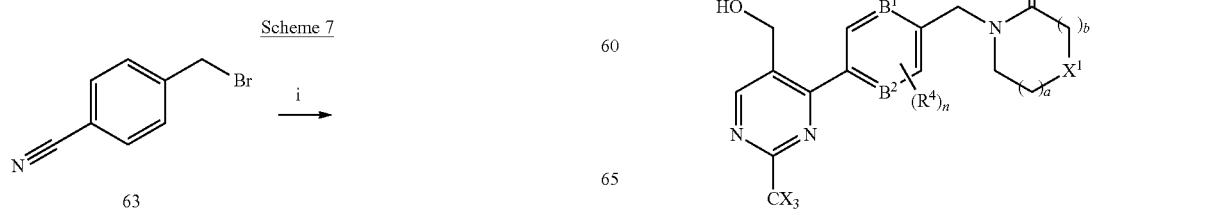

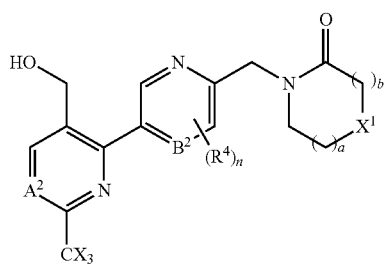
wherein $A^2$, $B^1$, $B^2$, $R^4$, X, $X^1$, a, b, and n have any of the values defined herein.
Examples of compounds of the formulae (XII) and XIII) include a compound selected from
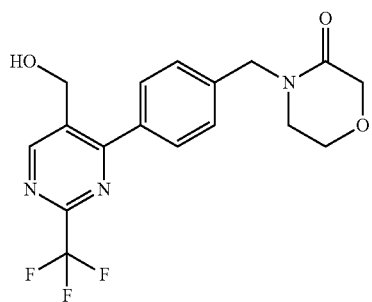
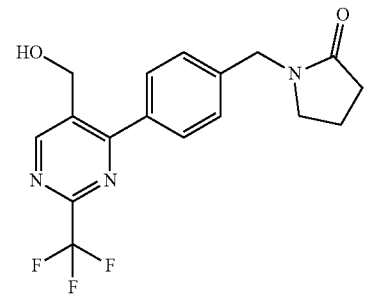
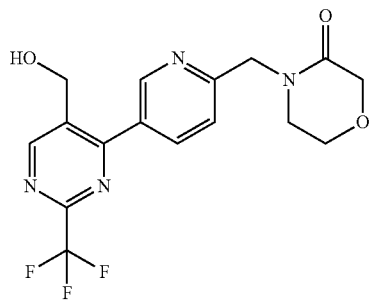
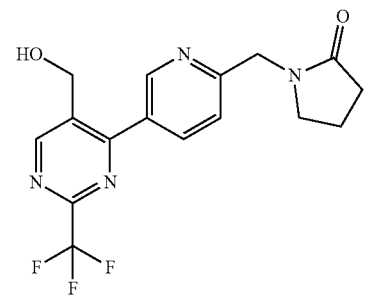
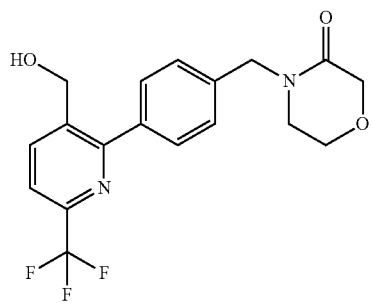
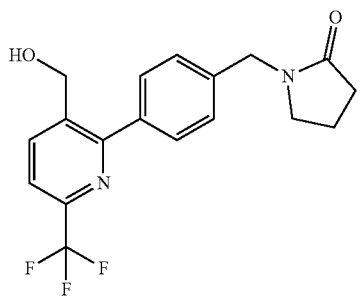
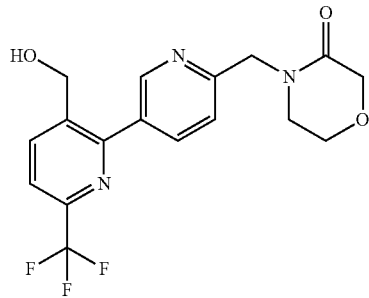
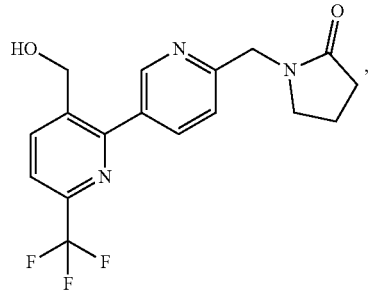
or a pharmaceutically acceptable salt thereof.
For example a compound selected from:
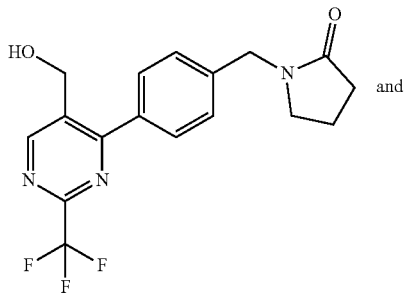

[Structure: HOCH2-substituted pyridine linked to pyridine-CH2-pyrrolidinone, with CF3 group]

or a pharmaceutically acceptable salt thereof.

Further Embodiments

Also disclosed are the following numbered clauses as further embodiments illustrating the invention:

1. A compound of the formula (I), or a pharmaceutically acceptable salt thereof:

(I)

[Structure of formula (I)]

$A^1$ is N or $CR^1$;
$A^2$ is N or $CR^3$;
and wherein only a single one of $A^1$ and $A^2$ may be N;
$R^1$ is selected from the group consisting of: H, CN, $C_{1-4}$ alkyl, $C_{1-4}$ haloalkyl, $C_{3-4}$ cycloalkyl, —$C_{1-4}$ alkyl-$OR^{A1}$ and —$C(O)NR^{A1}R^{B1}$;
$R^2$ is selected from the group consisting of: H, CN, $C_{1-4}$ alkyl, $C_{1-4}$ haloalkyl, $C_{3-4}$ cycloalkyl, —$C_{1-4}$ alkyl-$OR^{A2}$ and —$C(O)NR^{A2}R^{B2}$;
$R^3$ is selected from H, $C_{1-4}$ alkyl, $C_{1-4}$ haloalkyl, $C_{3-4}$ cycloalkyl, —$C_{1-4}$ alkyl-$OR^{A3}$ and —$C(O)NR^{A3}R^{B3}$;
each X is independently H or F, provided at least one X is F;
$B^1$ and $B^2$ are independently CH or N;
$R^4$ is halo;
$X^1$ is O or $CH_2$;
$R^{A1}$, $R^{B1}$, $R^{A2}$, $R^{B2}$, $R^{A3}$ and $R^{B3}$ are each independently selected from: H and $C_{1-4}$ alkyl;
a is an integer selected from 0, 1 or 2;
b is an integer selected from 0, 1 or 2;
a+b is 0, 1, 2 or 3; and
n is 0, 1 or 2;
with the following provisos:
$R^1$, $R^2$ and $R^3$ are not all H;
(ii) when $A^1$ is N, at least one of $R^2$ and $R^3$ is $C_{1-4}$ alkyl or $C_{1-4}$ haloalkyl;
(iii) when $A^2$ is N, at least one of $R^1$ and $R^2$ is $C_{1-4}$ alkyl or $C_{1-4}$ haloalkyl; and
(iv) when $A^1$ is $CR^1$, $R^1$ is —$CH_2OH$ and $B^1$ is N, then $R^2$ is not H.

2. The compound of clause 1, wherein the group —$CX_3$ is —$CF_3$.

3. The compound of clause 1 or clause 2, wherein $B^2$ is CH.

4. The compound of clause 1, wherein the compound is of the formula (III), or a pharmaceutically acceptable salt thereof:

(III)

[Structure of formula (III)]

5. The compound of any of clauses 1 to 4, wherein n is 0.

6. The compound of any of clauses 1 to 5, wherein $B^1$ is N.

7. The compound of any of clauses 1 to 5, wherein $B^1$ is CH.

8. The compound of any of clauses 1 to 7, wherein $A^1$ is N or $CR^1$ and $R^1$ is selected from the group consisting of: H, CN, $C_{1-3}$ alkyl, $C_{1-3}$ fluoroalkyl, alkyl-OH, —$C_{1-3}$ alkyl-OMe, —$C(O)NH_2$; —$C(O)NHMe$ and —$C(O)N(Me)_2$.

9. The compound of any of clauses 1 to 8, wherein $A^1$ is $CR^1$ and $R^1$ is CN.

10. The compound of any of clauses 1 to 9, wherein $R^2$ is selected from the group consisting of: H, $C_{1-3}$ alkyl, $C_{1-3}$ fluoroalkyl, alkyl-OH and —$C_{1-3}$ alkyl-OMe.

11. The compound of any of clauses 1 to 10, wherein $A^2$ is N or $CR^3$ and $R^3$ is selected from the group consisting of: H, $C_{1-3}$ fluoroalkyl and —$C_{1-3}$ alkyl-OH.

12. The compound of any of clauses 1 to 7, wherein the group of the formula:

[Structure showing pyrimidine core with $R^2$, $A^1$, $A^2$, $CX_3$ substituents]

is selected from the group consisting of:

[Two pyridine structures with HOCH2, methyl, and CF3 substituents]

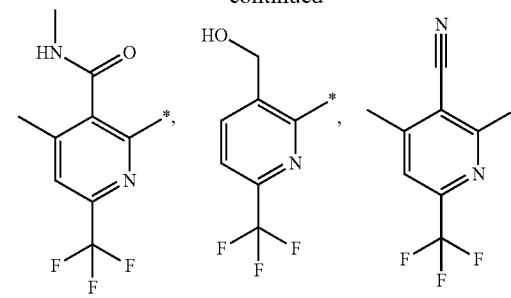
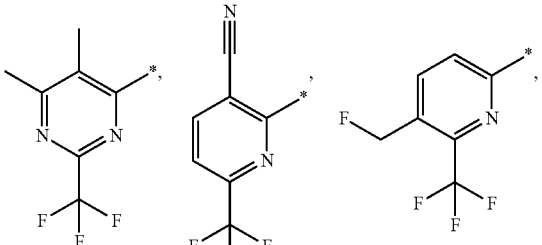
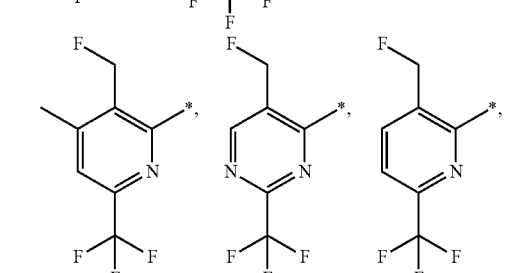
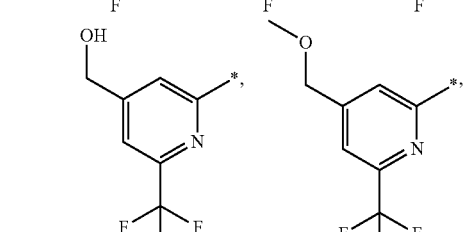
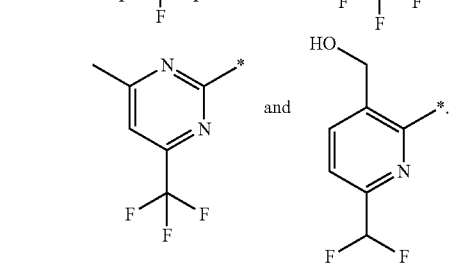
13. The compound of clause 1 selected from:
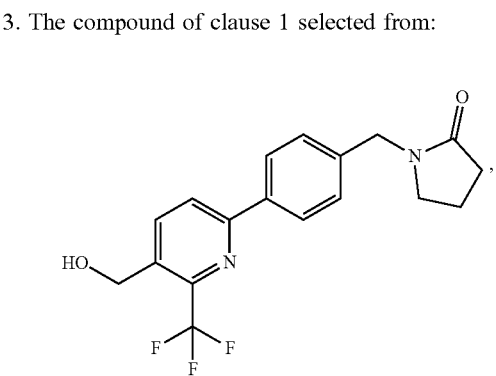
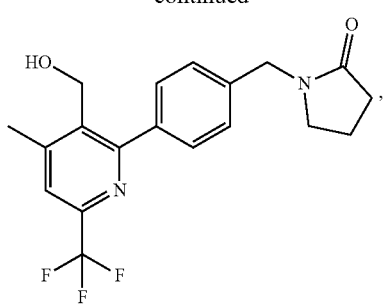
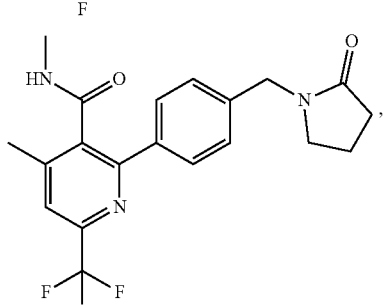
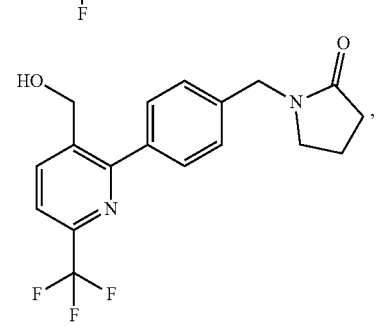
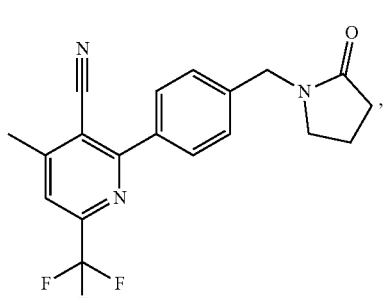
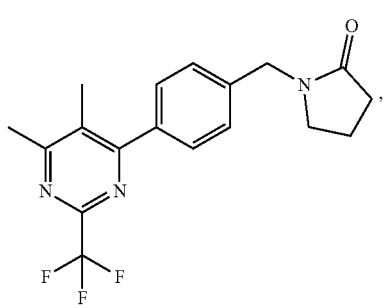

57
-continued
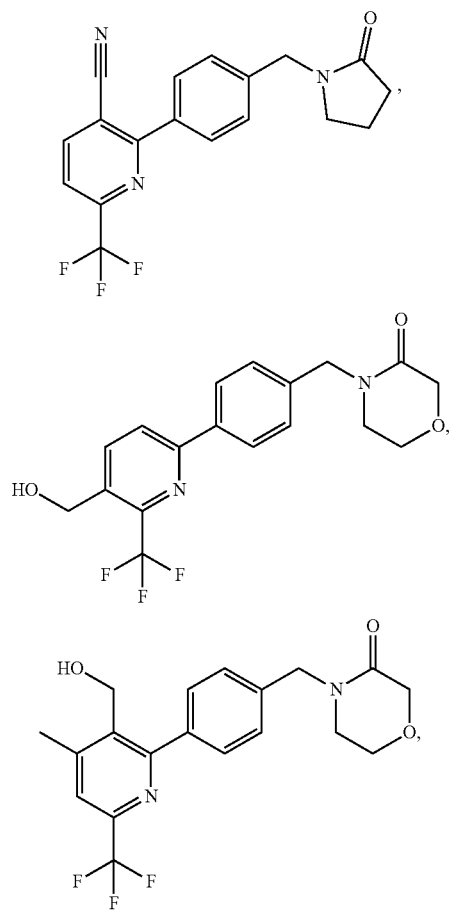
58
-continued
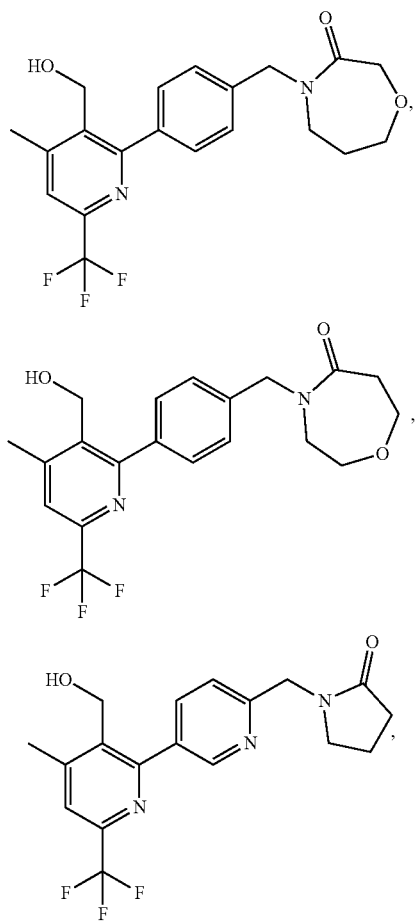
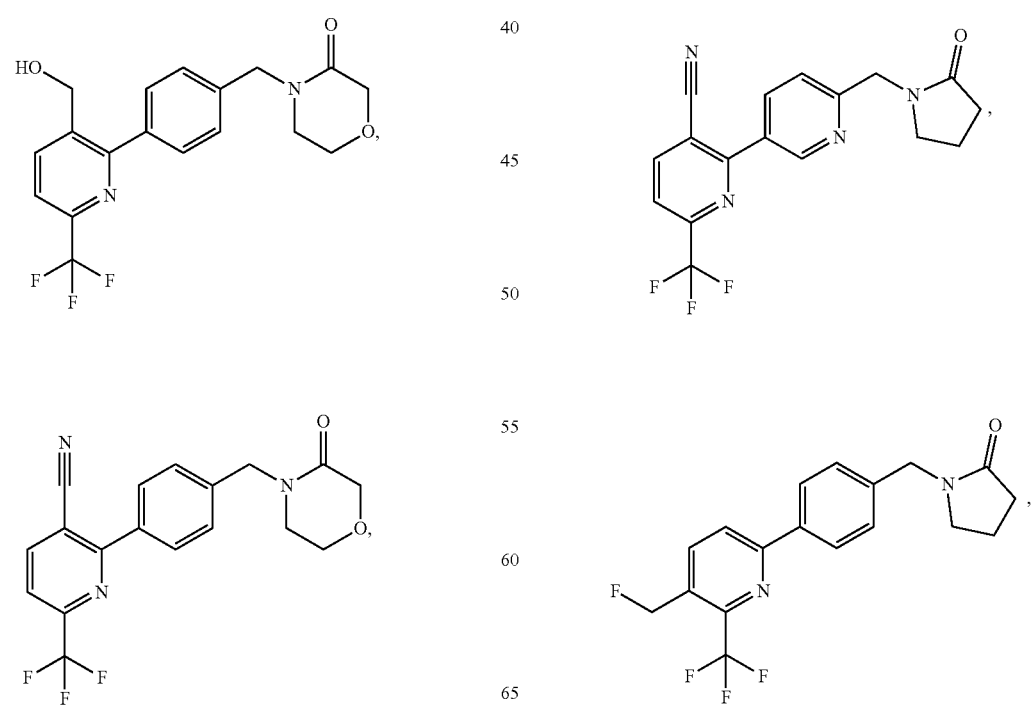

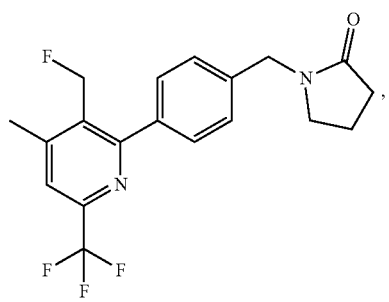
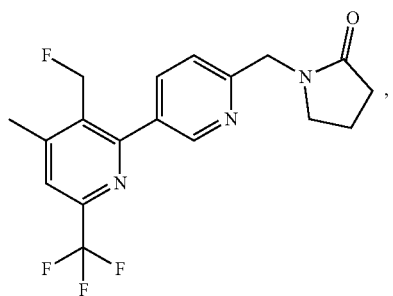

14. A pharmaceutical formulation comprising a compound of any of clauses 1 to 13 and a pharmaceutically acceptable excipient.

15. A compound of any of clauses 1 to 13, for use as a medicament.

16. A compound of any of clauses 1 to 13 for use in the treatment of a condition which is modulated by an AMPA receptor.

17. A compound of any of clauses 1 to 13, for use in the treatment of a depressive disorder or a mood disorder.

18. A compound of any of clauses 1 to 13, for use in the treatment of a treatment-resistant depressive disorder.

19. A compound of any of clauses 1 to 13, for use in the treatment of cognitive dysfunction.

20. The compound for the use of clause 19, wherein the cognitive dysfunction is associated with a neurological or neuropsychiatric disorder.

21. A compound of any of clauses 1 to 13 for use in the treatment of a central nervous system disorder associated with an alteration in one or more of cognitive function, synaptic plasticity or an imbalance in excitatory/inhibitory neurotransmission.

22. A compound for the use of clause 20 or clause 21, wherein the disorder is selected from: schizophrenia, bipolar disorder, attention-deficit hyperactivity disorder, a depressive disorder, a neurodegenerative disorder (for example Alzheimer's disease, Huntington's disease or Parkinson's disease), a neurodevelopmental disorder, a motor neuron disease (for example amyotrophic lateral sclerosis), ataxia, respiratory depression and a hearing disorder.

23. A compound of any of clauses 1 to 13 for use in the treatment of cognitive dysfunction associated with schizophrenia 24. A compound for the use of any of clauses 15 to 23, wherein the compound is co-administered to a subject with an additional therapeutic agent.

25. A compound for the use of clause 24, wherein the additional therapeutic agent is selected from an antipsychotic and an anti-depressant.

26. A compound selected from:

EXAMPLES

Throughout this specification these abbreviations have the following meanings:

Ac=acetyl
Aq.=aqueous
(Bpin)$_2$=Bis(pinacolato)diboron
DCM=dichloromethane
Deoxo-Fluor®=bis(2-methoxyethyl)aminosulfur trifluoride solution
DIBAL-H=diisobutylaluminium hydride
DIPEA=N,N-diisopropylethylamine
DMA=dimethylacetamide
DMF=N,N-dimethylformamide
DMSO=dimethyl sulfoxide
Et=ethyl
EtOAc=ethyl acetate
h=hours
HATU=1-[bis(dimethylamino)methylene]-1H-1,2,3-triazolo[4,5-b]pyridinium 3-oxide hexafluorophosphate
HEPES=4-(2-Hydroxyethyl)-1-piperazineethanesulponic acid
KOAc=potassium acetate
Me=methyl
MeCN=acetonitrile
min=minutes
mol=mole
MsCl=mesyl chloride
NBS=N-bromosuccinimide
Pd(dppf)Cl$_2$=1,1'-Bis(diphenylphosphino)ferrocene]dichloropalladium(II)
Pd(PPh$_3$)$_2$Cl$_2$=bis(triphenylphosphine)palladium(II) dichloride
PhOP(O)Cl$_2$=phenyl dichlorophosphate
pTsOH=para-toluene sulfonic acid
R$_t$=retention time
RT=room temperature
Sat.=saturated
TEMPO=(2,2,6,6-Tetramethylpiperidin-1-yl)oxyl TMPMgCl.LiCl=2,2,6,6-Tetramethylpiperidinylmagnesium chloride lithium chloride complex
THF=tetrahydrofuran Solvents, reagents and starting materials were purchased from commercial vendors and used as received unless otherwise described. All reactions were performed at room temperature unless otherwise stated.

LCMS data was recorded on a Waters 2695 HPLC using a Waters 2487 UV detector and a Thermo LCQ ESI-MS. Samples were eluted through a Phenomenex Luna 3μ C18 50 mm×4.6 mm column, using water and acetonitrile acidified by 0.1% formic acid at 1.5 mL/min and detected at 254 nm.

The methods employed were:
4 Minute Method
The gradient employed was:

| Time (minutes) | % Water + 0.1% formic acid | % MeCN + 0.1% formic acid |
| --- | --- | --- |
| 0.0 | 65 | 35 |
| 3.5 | 10 | 90 |
| 3.9 | 10 | 90 |
| 4.0 | 65 | 35 |

7 Minute Method
The gradient employed was:

| Time (minutes) | % Water + 0.1% formic acid | % MeCN + 0.1% formic acid |
| --- | --- | --- |
| 0.0 | 70 | 30 |
| 5.0 | 10 | 90 |
| 6.0 | 10 | 90 |
| 6.5 | 70 | 30 |
| 7.0 | 70 | 30 |

10 Minute Method
The gradient employed was:

| Time (minutes) | % Water + 0.1% formic acid | % MeCN + 0.1% formic acid |
| --- | --- | --- |
| 0.0 | 95 | 5 |
| 8.0 | 5 | 95 |
| 8.5 | 5 | 95 |
| 9.0 | 95 | 5 |
| 9.5 | 95 | 5 |

NMR was also used to characterise final compounds. NMR spectra were recorded at 400, 500 or 600 MHz on a Varian VNMRS 400, 500 or 600 MHz spectrometer (at 30° C.), using residual isotopic solvent (CHCl$_3$, δ$_H$=7.27 ppm, DMSO δ$_H$=2.50 ppm, MeOH δ$_H$=3.31 ppm) as an internal reference. Chemical shifts are quoted in parts per million (ppm). Coupling constants (J) are recorded in Hertz.

1-[(4-Bromophenyl)methyl]pyrrolidin-2-one (3)

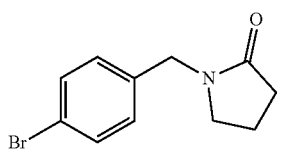 [SMILES: O=C1CCCN1Cc1ccc(Br)cc1]

To a solution of pyrrolidin-2-one (1.3 mL, 16.8 mmol) in N,N-dimethylformamide (10 mL) at 0° C. was added sodium hydride (60% in oil) (0.77 g, 19.2 mmol) portionwise and the mixture was left stirring at 0° C. for about 30 min. Then 4-bromobenzyl bromide (1) (4.00 g, 16.0 mmol) was added portionwise over 5 min. The reaction mixture was allowed to warm to room temperature and stirred for 16 hours. The reaction mixture was quenched with water, diluted with EtOAc (100 mL), the organic layer was washed with brine (3×100 mL), dried (MgSO$_4$) and solvent evaporated under reduced pressure, the crude material was purified by column chromatography (50 g, silica) eluting with petrol:EtOAc (1:1). The desired fractions were concentrated under reduced pressure to afford the title compound as a clear colourless oil (3.74 g, 90%). R$_f$ 0.29 (1:3 ethyl acetate:petrol); $^1$H NMR (500 MHz, Chloroform-d) δ 7.46 (d, J=8.5 Hz, 2H), 7.13 (d, J=8.0 Hz, 2H), 4.41 (s, 2H), 3.26 (t, J=7.1 Hz, 2H), 2.45 (t, J=8.1 Hz, 2H), 2.00 (p, J=7.6 Hz, 2H); LCMS (7 minute method) product at R$_t$=2.83 min and ES$^+$ m/z 254.28, 256.13 [M+H]$^+$ (Br isotope)

1-[[4-(4,4,5,5-Tetramethyl-1,3,2-dioxaborolan-2-yl)phenyl]methyl]pyrrolidin-2-one (8)

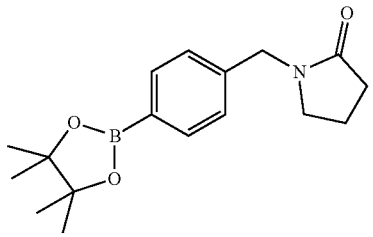 [SMILES: CC1(C)OB(c2ccc(CN3CCCC3=O)cc2)OC1(C)C]

To flask containing 1-[(4-bromophenyl)methyl]pyrrolidin-2-one (3) (3.74 g, 14.7 mmol), bis(pinacolato)diboron (5.61 g, 22.1 mmol), potassium acetate (4.33 g, 44.2 mmol), and Pd(dppf)Cl$_2$ (538 mg, 0.74 mmol) was evacuated and charged with nitrogen 3 times. Dimethyl sulfoxide (40 mL) was added to the solids and the reaction mixture was heated at 90° C. for 4 hours. The reaction mixture was allowed to cool to room temperature where it was diluted with EtOAc (100 mL) and extracted with brine (3×50 mL).

The organic phase was dried over MgSO$_4$, filtered and concentrated under reduced pressure. The residue was purified by flash column chromatography (40 g silica, petrol:EtOAc, 100:0 to 50:50). The desired fractions were concentrated under reduced pressure to afford the title compound as a clear pale yellow oil (4.2 g 95%); R$_f$ 0.39 (1:1 ethyl acetate:petrol); $^1$H NMR (500 MHz, Chloroform-d) δ 7.78 (d, J=7.6 Hz, 2H), 7.25 (d, J=7.7 Hz, 2H), 4.47 (s, 2H), 3.24 (t, J=7.1 Hz, 2H), 2.45 (t, J=8.1 Hz, 2H), 1.99 (p, J=7.6 Hz, 2H), 1.35 (s, 12H); LCMS (7 minute method) product at R$_t$=3.52 min and ES$^+$ m/z 302.11 [M+H]$^+$ 4-[(4-Bromophenyl)methyl]morpholin-3-one (4)

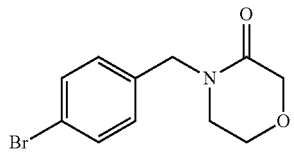

To a solution of morpholin-3-one (2.22 g, 22.0 mmol) in N,N-dimethylformamide (25 mL) at 0° C. was added sodium hydride (60% in oil) (967 mg, 24.2 mmol) portionwise. The reaction mixture was allowed to stir at 0° C. for 30 minutes before the portionwise addition of 4-bromobenzyl bromide (1) (5.00 g, 20.0 mmol). The reaction mixture was allowed to warm to room temperature where it was stirred for 4 hours. The reaction was quenched with deionised water (2 mL), diluted with EtOAc (100 mL) and washed with brine (3×100 mL). The organic phase was dried over MgSO$_4$, filtered and concentrated under reduced pressure to afford the title compound as a colourless oil (5.5 g, 97%); $^1$H NMR (500 MHz, Chloroform-d) δ 7.46 (d, J=8.3 Hz, 2H), 7.15 (d, J=8.1 Hz, 2H), 4.57 (s, 2H), 4.24 (s, 2H), 3.90-3.79 (m, 2H), 3.32-3.19 (m, 2H); LCMS (4 minute method) product at R$_t$=1.80 min and ES$^+$ m/z 269.96, 271.92 [M+H]$^+$ (Br isotope)

4-[[4-(4,4,5,5-Tetramethyl-1,3,2-dioxaborolan-2-yl)phenyl]methyl]morpholin-3-one (9)

To a solution of 1,4-oxazepan-3-one (400 mg, 3.47 mmol) in N,N-dimethylformamide (5 mL) at 0° C. was added sodium hydride (60% in oil) (181 mg, 4.52 mmol) portionwise and the mixture was left stirring at 0° C. for 30 minutes. 4-Bromobenzyl bromide (1) (912 mg, 3.65 mmol) was then added portionwise and the reaction mixture allowed to warm to room temperature where it was stirred for 16 hours. The reaction mixture was quenched with water (2 mL) and concentrated to dryness. The residue was taken up in EtOAc (50 mL) and the organic phase was washed with water (2×50 mL) then saturated brine solution (1×50 mL). The organic phase was dried (MgSO$_4$), filtered and concentrated to dryness under reduced pressure to afford the title compound as a white solid (1.07 g, 99%) as a white solid; $^1$H NMR (500 MHz, Chloroform-d) δ 7.46 (d, J=8.4 Hz, 2H), 7.16 (d, J=8.2 Hz, 2H), 4.56 (s, 2H), 4.31 (s, 2H), 3.81 (t, J=6.0 Hz, 2H), 3.46-3.37 (m, 2H), 1.91-1.80 (m, 2H); LCMS (4 minute method) product at R$_t$=0.53 min and ES$^+$ m/z 284.04, 286.01 [M+H]$^+$ (Br isotope)

4-[[4-(4,4,5,5-Tetramethyl-1,3,2-dioxaborolan-2-yl)phenyl]methyl]-1,4-oxazepan-3-one (10)

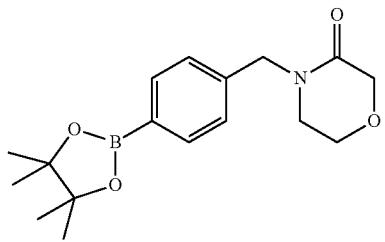 [SMILES: CC1(C)OB(c2ccc(CN3CCOCC3=O)cc2)OC1(C)C]

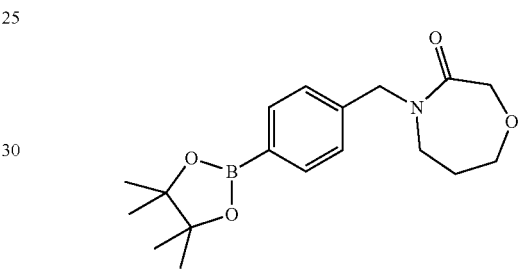

To flask containing 4-[(4-bromophenyl)methyl]morpholin-3-one (4) (5.5 g, 20.3 mmol), bis(pinacolato)diboron (7.76 g, 30.5 mmol), potassium acetate (5.99 g, 61.1 mmol), and Pd(dppf)Cl$_2$ (744 mg, 1.02 mmol) was evacuated and charged with nitrogen 3 times. Dimethyl sulfoxide (55 mL) was added to the solids and the reaction mixture was heated at 90° C. for 4 hours. The reaction mixture was allowed to cool to room temperature where it was diluted with EtOAc (250 mL) and extracted with brine (3×100 mL).

The organic phase was dried over MgSO$_4$, filtered and concentrated under reduced pressure. The residue was purified by flash column chromatography (100 g silica, petrol:EtOAc, 100:0 to 40:60, NOTE: very weak UV signal). The desired fractions were concentrated under reduced pressure to afford the title compound as a white solid (5.3 g, 78%). R$_f$ 0.39 (1:1 ethyl acetate:petrol); $^1$H NMR (500 MHz, Chloroform-d) δ 7.78 (d, J=7.7 Hz, 2H), 7.27 (d, J=7.9 Hz, 2H), 4.63 (s, 2H), 4.25 (s, 2H), 3.90-3.75 (m, 2H), 3.29-3.13 (m, 2H), 1.33 (s, 12H); LCMS (4 minute method) product at R$_t$=2.41 min and ES$^+$ m/z 318.08 [M+H]$^+$ 4-[(4-Bromophenyl)methyl]-1,4-oxazepan-3-one (5)

To bis(pinacolato)diboron (1.43 g, 5.65 mmol), Pd(dppf)Cl$_2$ (138 mg, 0.19 mmol) and 4-[(4-bromophenyl)methyl]-1,4-oxazepan-3-one (5) (1.07 g, 3.77 mmol) under nitrogen was added potassium acetate (1.11 g, 11.3 mmol), followed by dry dimethyl sulfoxide (10 mL) and the reaction mixture was heated at 90° C. for 4 hours. The reaction mixture was cooled to room temperature and diluted with EtOAc (100 mL). The organic phase was washed with brine (3×50 mL), dried (MgSO$_4$), filtered and evaporated under reduced pressure to give the crude product which was purified by flash column chromatography eluting petrol:EtOAc (90:10 to 50:50). The desired fractions were combined and concentrated to dryness under reduced pressure to afford the title compound as a white solid (1.04 g, 84%); $^1$H NMR (500 MHz, Chloroform-d) δ 7.78 (d, J=8.0 Hz, 2H), 7.28 (d, J=8.1 Hz, 2H), 4.63 (s, 2H), 4.32 (s, 2H), 3.80 (t, J=5.9 Hz, 2H), 3.43-3.36 (m, 2H), 1.85-1.76 (m, 2H), 1.35 (s, 12H); LCMS (4 minute method) product at R$_t$=2.20 min and ES$^+$ m/z 332.14 [M+H]$^+$ 4-[(4-Bromophenyl)methyl]-1,4-oxazepan-5-one (6)

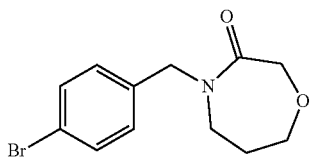 [SMILES: O=C1COCCCN1Cc1ccc(Br)cc1]

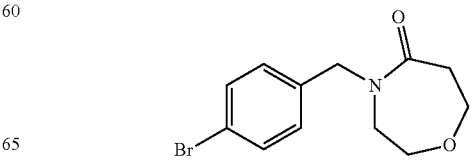

To a solution of 1,4-oxazepan-5-one (400 mg, 3.47 mmol) in N,N-dimethylformamide (5 mL) at 0° C. was added sodium hydride (60% in oil) (181 mg, 4.52 mmol) portionwise and the mixture was left stirring at 0° C. for 30 minutes. 4-Bromobenzyl bromide (1) (912 mg, 3.65 mmol) was then added portionwise and the reaction mixture allowed to warm to room temperature where it was stirred for 16 hours. The reaction mixture was quenched with water (2 mL) and concentrated to dryness. The residue was taken up in EtOAc (50 mL) and this was washed with water (2×50 mL) then saturated brine solution (1×50 mL). The organic phase was dried (MgSO$_4$), filtered and concentrated to dryness under reduced pressure to afford the title compound as a white oily solid (1.12 g, 96%); $^1$H NMR (500 MHz, Chloroform-d) δ 7.46 (d, J=8.4 Hz, 2H), 7.14 (d, J=8.4 Hz, 2H), 4.55 (s, 2H), 3.84-3.75 (m, 2H), 3.63-3.54 (m, 2H), 3.44-3.37 (m, 2H), 2.86-2.79 (m, 2H); LCMS (4 minute method) product at R$_t$=1.50 min and ES$^+$ m/z 284.04, 286.01 [M+H]$^+$ (Br isotope)

4-[[4-(4,4,5,5-Tetramethyl-1,3,2-dioxaborolan-2-yl)phenyl]methyl]-1,4-oxazepan-5-one (11)

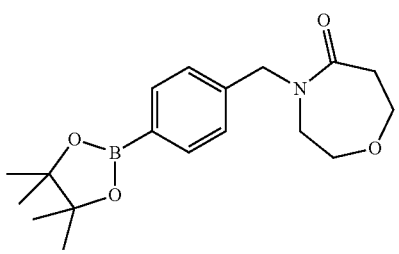 [SMILES: CC1(C)OB(c2ccc(CN3CCOCCC3=O)cc2)OC1(C)C]

To bis(pinacolato)diboron (1.28 g, 5.03 mmol), Pd(dppf)Cl$_2$ (123 mg, 0.17 mmol) and 4-[(4-bromophenyl)methyl]-1,4-oxazepan-5-one (6) (1.12 g, 3.35 mmol) under nitrogen was added potassium acetate (0.99 g, 10.05 mmol), followed by dry dimethyl sulfoxide (10 mL) and the reaction mixture was heated at 90° C. for 4 hours. The reaction mixture was cooled to room temperature and diluted with EtOAc (100 mL). This was washed with brine (3×50 mL), dried (MgSO$_4$), filtered and evaporated under reduced pressure to give the crude product which was purified by flash column chromatography eluting petrol:EtOAc (90:10 to 50:50). The desired fractions were concentrated under reduced pressure to afford the title compound as a white solid (694 mg, 63%); $^1$H NMR (500 MHz, Chloroform-d) δ 7.77 (d, J=7.4 Hz, 2H), 7.30-7.24 (m, 2H), 4.63 (s, 2H), 3.85-3.76 (m, 2H), 3.58-3.51 (m, 2H), 3.44-3.35 (m, 2H), 2.88-2.80 (m, 2H), 1.35 (s, 12H); LCMS (4 minute method) product at R$_t$=2.11 min and ES$^+$ m/z 332.14 [M+H]$^+$ 1-[(5-Bromo-2-pyridyl)methyl]pyrrolidin-2-one (7)

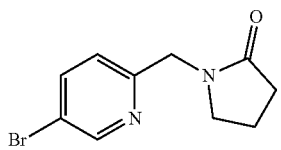 [SMILES: O=C1CCCN1Cc1ccc(Br)cn1]

To a mixture of (5-bromo-2-pyridyl)methanol (2) (5.0 g, 26.6 mmol) and N,N-diisopropylethylamine (5.56 mL, 31.9 mmol) in DCM (50 mL) at 0° C. was added methanesulfonyl chloride (2.37 mL, 30.6 mmol) dropwise. The reaction mixture was allowed to warm to room temperature slowly and after stirring for 16 hours was concentrated under reduced pressure to afford a yellow oil. The yellow oil was dissolved in EtOAc (30 mL), washed with sat. aq. NaHCO$_3$, dried over MgSO$_4$ and concentrated under reduced pressure to afford a yellow oil. To a suspension of sodium hydride (60% in oil) (1.38 g, 34.6 mmol) in tetrahydrofuran (50 mL) cooled at 0° C. was added pyrrolidin-2-one (2.63 mL, 34.6 mmol) slowly (gas evolution). The reaction mixture was stirred for a further 30 minutes at this temperature. The crude mesylate in tetrahydrofuran (50 mL) was added dropwise to the reaction mixture maintaining the temperature below 25° C. The resulting reaction mixture was stirred for 72 hours at room temperature. The solvent was removed under reduced pressure and the residual material diluted with ethyl acetate (50 mL). The organic layer was washed with sat. aq. NaHCO$_3$ (30 mL) and brine (30 mL), dried over MgSO$_4$ and concentrated under reduced pressure. The residue was purified by flash column chromatography (100 g silica, petrol:EtOAc, 100:0 to 0:100). The desired fractions were concentrated under reduced pressure to afford the title compound as a yellow oil (5.4 g, 76%); R$_f$ 0.19 (100% ethyl acetate); $^1$H NMR (500 MHz, Chloroform-d) δ 8.60 (d, J=2.3 Hz, 1H), 7.79 (dd, J=8.3, 2.2 Hz, 1H), 7.19 (d, J=8.3 Hz, 1H), 4.55 (s, 2H), 3.41 (t, J=7.1 Hz, 2H), 2.45 (t, J=8.1 Hz, 2H), 2.05 (p, J=7.6 Hz, 2H); LCMS (4 minute method) product at R$_t$=0.63 min and ES$^+$ m/z 255.11, 257.13 [M+H]$^+$ (Br isotope)

1-[[5-(4,4,5,5-Tetramethyl-1,3,2-dioxaborolan-2-yl)-2-pyridyl]methyl]pyrrolidin-2-one (12)

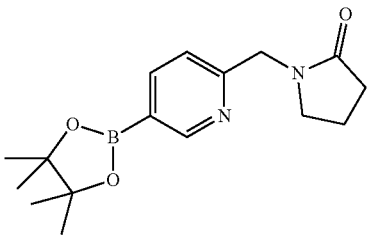 [SMILES: CC1(C)OB(c2ccc(CN3CCCC3=O)nc2)OC1(C)C]

To 1-[(5-bromo-2-pyridyl)methyl]pyrrolidin-2-one (7) (510 mg, 2.00 mmol), bis(pinacolato)diboron (761 mg, 3.00 mmol) and potassium acetate (588 mg, 6.00 mmol) under nitrogen was added Pd(dppf)Cl$_2$ (73 mg, 0.10 mmol), followed by dry 1,4-dioxane (14 mL) and the reaction mixture was heated at 80° C. for 5 hours. The reaction mixture was cooled to room temperature, diluted with EtOAc (100 mL) and the organic phase was washed with brine (3×50 mL), dried (MgSO$_4$), filtered and evaporated under reduced pressure to give the crude product as a runny brown oil. The crude material was purified by flash silica column chromatography eluting petrol:EtOAc (50:50 to 0:100), then 100% EtOAc to 10% MeOH in EtOAc. The desired fractions were concentrated under reduced pressure to afford the title compound as a light brown oil (138 mg, 23%); $^1$H NMR (500 MHz, Chloroform-d) δ 8.87 (s, 1H), 8.05 (d, J=7.7 Hz, 1H), 7.26 (d, J=7.8 Hz, 1H), 4.62 (s, 2H), 3.38 (t, J=7.1 Hz, 2H), 2.45 (t, J=8.1 Hz, 2H), 2.07-1.98 (m, 2H), 1.35 (s, 12H); LCMS (4 minute method) product at R$_t$=0.40 min and ES$^+$ m/z 302.96 [M+H]$^+$

Ethyl 2-hydroxy-6-(trifluoromethyl)-3,4-dihydro-pyridine-5-carboxylate (14)

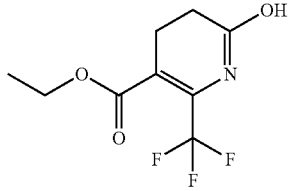 [SMILES: CCOC(=O)C1=C(C(F)(F)F)N=C(O)CC1]

A mixture of ethyl 4,4,4-trifluoroacetoacetate (13) (14.8 mL, 101 mmol), acrylamide (4.5 g, 63.3 mmol) and p-toluenesulfonic acid monohydrate (0.16 g, 0.82 mmol) in toluene (60 mL) was refluxed for about 48 hours with azeotropic removal of water with a Dean-Stark apparatus. The reaction mixture was then concentrated to a small volume, by slow distillation of toluene at atmospheric pressure. Toluene (60 mL) was added and again the reaction mixture was concentrated, through slow distillation of toluene. After repeating this operation three times, the reaction mixture was concentrated under reduced pressure to give a yellow solid. The crude material was dissolved in EtOAc and the insoluble material was filtered off and the filtrate was evaporated under reduced pressure to afford a yellow solid (12 g). The crude material was purified twice by column chromatography (SiO$_2$, 25 g) gradient eluent 100% DCM to 9:1 DCM:MeOH. The desired fractions were concentrated under reduced pressure to afford the title compound as a light yellow solid (4.6 g. 31%); $^1$H NMR (500 MHz, Chloroform-d) δ 4.28 (q, J=7.1 Hz, 2H), 2.85-2.72 (m, 2H), 2.65-2.53 (m, 2H), 1.33 (t, J=7.2 Hz, 3H); LCMS (4 minute method) product at R$_t$=1.17 min and ES$^+$ m/z 238.07 [M+H]$^+$

Ethyl 6-hydroxy-2-(trifluoromethyl)pyridine-3-carboxylate (15)

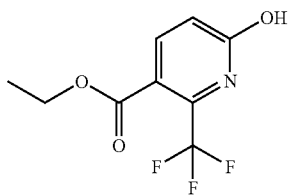 [SMILES: CCOC(=O)c1ccc(O)nc1C(F)(F)F]

A solution of ethyl 2-hydroxy-6-(trifluoromethyl)-3,4-dihydropyridine-5-carboxylate (14) (2.8 g, 11.8 mmol) and N-bromosuccinimide (2.1 g, 11.8 mmol) in carbon tetrachloride (25 mL) was heated at reflux overnight. The resulting precipitate was filtered off and the filtrate was concentrated under reduced pressure to afford a yellow solid that was purified by flash chromatography (silica gel 24 g, eluent gradient: from petrol:EtOAc 9:1 to 1:1. The desired fractions were concentrated under reduced pressure and repurified by column chromatography (SiO$_2$, 10 g, eluent petrol:EtOAC 9:1 to 1:1). The desired fractions were concentrated under reduced pressure to afford the title compound as a white solid (890 mg, 32%); $^1$H NMR (500 MHz, Chloroform-d) δ 8.01 (d, J=9.2 Hz, 1H), 6.87 (d, J=9.2 Hz, 1H), 4.39 (q, J=7.1 Hz, 2H), 1.39 (t, J=7.1 Hz, 3H); LCMS (4 minute method) product at R$_t$=0.44 min and ES$^+$ m/z 236.09 [M+H]$^+$

Ethyl 6-chloro-2-(trifluoromethyl)pyridine-3-carboxylate (16)

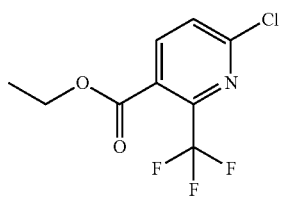 [SMILES: CCOC(=O)c1ccc(Cl)nc1C(F)(F)F]

A mixture of ethyl 6-hydroxy-2-(trifluoromethyl)pyridine-3-carboxylate (15) (890 mg, 3.78 mmol) and phenyl dichlorophosphate (0.85 mL, 5.68 mmol) was heated under microwave irradiation for 30 min at 170° C. The reaction mixture was poured into ice, stirred for 20 min and diluted with ethyl acetate (50 mL). The pH was adjusted to 10, by addition of a sat. aq. solution of sodium bicarbonate (50 mL) and then the organic layer was separated, washed with water, dried over Na$_2$SO$_4$ and concentrated under reduced pressure to give a brown oil which was purified by column chromatography (SiO$_2$, 12 g, gradient elution 100% petrol to 50% EtOAc in petrol). The desired fractions were concentrated under reduced pressure to afford the title compound as a clear oil (650 mg, 68%; $^1$H NMR (500 MHz, Chloroform-d) δ 8.09 (d, J=8.3 Hz, 1H), 7.60 (d, J=8.2 Hz, 1H), 4.44 (q, J=7.1 Hz, 2H), 1.41 (t, J=7.1 Hz, 3H); LCMS (4 minute method) product at R$_t$=2.02 min and ES$^+$ m/z 254.04, 256.02 [M+H]$^+$ (Cl isotope)

[6-Chloro-2-(trifluoromethyl)-3-pyridyl]methanol (17)

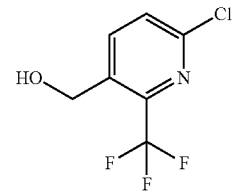 [SMILES: OCc1ccc(Cl)nc1C(F)(F)F]

To a solution of ethyl 6-chloro-2-(trifluoromethyl)pyridine-3-carboxylate (16) (650 mg, 2.56 mmol) in DCM (50 mL) at 0° C. was added diisobutylaluminum hydride (1 M solution in toluene) (7.69 mL, 7.69 mmol) and the mixture was slowly allowed to warm to room temperature and stirred overnight. Diisobutylaluminum hydride (1 M solution in toluene) (7.69 mL, 7.69 mmol) was added to the reaction mixture at 0° C. and allowed to warm up to room temperature and was stirred for 72 hours. The reaction mixture was quenched with sat. aq. Rochelle's salt and stirred for 30 min before concentrating down the solution. The product was then extracted into EtOAc (3×30 mL) the combined organic layers were washed with brine (50 mL), dried (MgSO$_4$) and solvent evaporated to leave a clear oil. The crude was purified by column chromatography (SiO$_2$, 10 g, gradient elution 10% EtOAc in petrol to 50% EtOAc in petrol). The desired fractions were concentrated to dryness under reduced pressure to afford the title compound as a light yellow oil (350 mg, 64%); $^1$H NMR (500 MHz, Chloroform-d) δ 8.14 (d, J=8.3 Hz, 1H), 7.57 (d, J=8.3 Hz, 1H), 4.93 (s, 2H); LCMS (4 minute method) product at R$_t$=1.39 min and ES$^+$ m/z 212.22, 214.22 [M+H]$^+$ (Cl isotope).

Ethyl 4-methyl-2-oxo-6-(trifluoromethyl)-1H-pyridine-3-carboxylate (19)

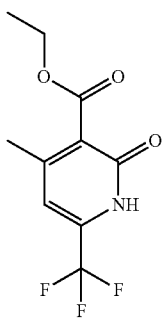 [SMILES: CCOC(=O)c1c(C)cc(C(F)(F)F)[nH]c1=O]

To a solution of ethyl malonate monoamide (18) (2.34 g, 17.9 mmol) and (E)-1,1,1-trifluoro-4-methoxy-pent-3-en-2-one (3.00 g, 17.9 mmol) in ethanol (20 mL) was added sodium ethoxide (21 wt % solution in ethanol) (6.3 mL, 92.7 mmol) and the mixture was heated to 85° C. overnight. Aqueous 2 M HCl (15 mL) was added to the reaction mixture, the solvent concentrated down under reduced pressure and the product extracted into EtOAc (2×30 mL). The combined organic layers were washed with brine (25 mL), dried (MgSO$_4$), filtered and solvent evaporated under reduced pressure to afford the title compound as an orange oil (3.6 g, 73%); $^1$H NMR (500 MHz, Chloroform-d) δ 7.07 (s, 1H), 4.51 (q, J=7.1 Hz, 2H), 2.63 (s, 3H), 1.46 (t, J=7.1 Hz, 3H); LCMS (4 minute method) product at R$_t$=2.20 min and ES$^+$ m/z 249.97 [M+H]$^+$ Ethyl 2-chloro-4-methyl-6-(trifluoromethyl)pyridine-3-carboxylate (20)

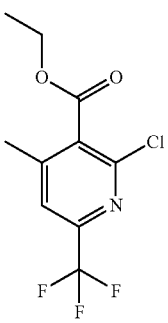 [SMILES: CCOC(=O)c1c(C)cc(C(F)(F)F)nc1Cl]

A mixture of ethyl 4-methyl-2-oxo-6-(trifluoromethyl)-1H-pyridine-3-carboxylate (19) (1.56 g, 6.26 mmol) and phenyl dichlorophosphate (3.27 mL, 21.9 mmol) was heated under microwave irradiation for 30 min at 165° C. The reaction mixture was poured into ice, stirred for 20 min and diluted with ethyl acetate (50 mL). The pH was adjusted to 10, by addition of sat. aq. NaHCO$_3$ (50 mL) and then the organic layer was separated, washed with water, dried over Na$_2$SO$_4$ and concentrated under reduced pressure to give a brown oil which was purified by flash chromatography (silica gel 25 g, eluent gradient: 100% petrol to 50% EtOAc in petrol). The desired fractions were concentrated under reduced pressure to afford the title compound as a yellow oil (615 mg, 36%); $^1$H NMR (500 MHz, Chloroform-d) δ 7.49 (s, 1H), 4.48 (q, J=7.2 Hz, 2H), 2.45 (s, 3H), 1.43 (t, J=7.2 Hz, 3H); LCMS (4 minute method) product at R$_t$=3.03 min and ES$^+$ m/z 268.09 [M+H]$^+$

[2-Chloro-4-methyl-6-(trifluoromethyl)-3-pyridyl]methanol (21)

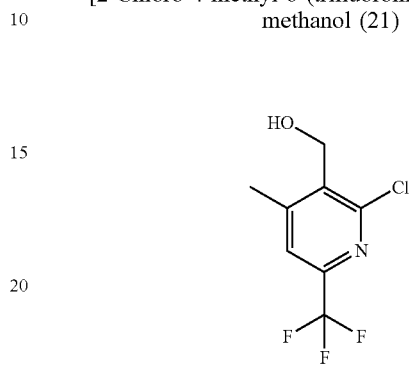

To a solution of ethyl 2-chloro-4-methyl-6-(trifluoromethyl)pyridine-3-carboxylate (20) (800 mg, 2.99 mmol) in DCM (25 mL) at 0° C. was added diisobutylaluminum hydride (1 M solution in toluene) (8.97 mL, 8.97 mmol) and the mixture was slowly allowed to stirred at room temperature. After about an hour more diisobutylaluminum hydride (1 M solution in toluene) (8.97 mL, 8.97 mmol) was added and the reaction was then left to stir at room temperature overnight. The reaction mixture was quenched with sat. aq. Rochelle's salt and stirred for 30 min. The product was then extracted into DCM (3×35 mL) and the combined organic layers were washed with brine (50 mL), dried (MgSO$_4$) and solvent evaporated under reduced pressure to afford the title compound as a white solid (525 mg, 78%); $^1$H NMR (500 MHz, Chloroform-d) δ 7.47 (s, 1H), 4.90 (s, 2H), 2.58 (s, 3H); LCMS (4 minute method) product at R$_t$=1.60 min and ES$^+$ m/z the desired mas ion was not observed.

2-Chloro-4-methyl-6-(trifluoromethyl)pyridine-3-carboxylic Acid (22)

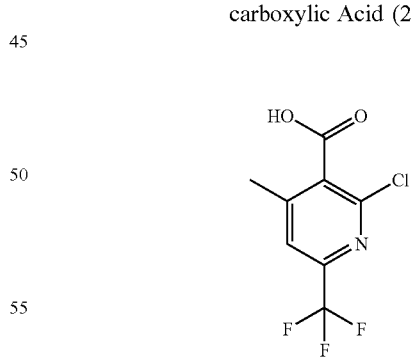

To a solution of ethyl 2-chloro-4-methyl-6-(trifluoromethyl)pyridine-3-carboxylate (20) (488 mg, 1.82 mmol) in tetrahydrofuran (2 mL) and ethanol (0.50 mL) was added sodium hydroxide (1.0 M in H$_2$O) (3.65 mL, 3.65 mmol). The reaction mixture was stirred at room temperature overnight and then heated to 50° C. for a further 24 hours. The solvent was concentrated under reduced pressure, water was added (10 mL) and solution washed with EtOAc (2×10 mL). The aqueous layer was acidified with aqueous HCl (1.0 M)

until neutral pH and the product was extracted into EtOAc (2×10 mL). The combined organic extracts were washed with brine, and dried over MgSO$_4$, filtered, and concentrated under reduced pressure to afford the title compound as a light yellow solid (370 mg, 80%); $^1$H NMR (500 MHz, DMSO-d$_6$) δ 7.97 (s, 1H), 2.43 (s, 3H); LCMS (4 minute method) product at R$_t$=1.55 min and ES$^+$ m/z the desired mass ion was not observed.

2-Chloro-N,4-dimethyl-6-(trifluoromethyl)pyridine-3-carboxamide (23)

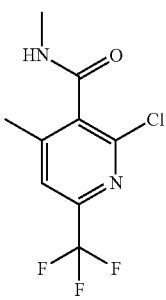 [SMILES: CNC(=O)c1c(C)cc(C(F)(F)F)nc1Cl]

To a solution of HATU (523 mg, 1.38 mmol) in N,N-dimethylformamide (25 mL) were added a solution of methyl amine (2.0 M in THF) (1.88 mL, 3.76 mmol), N,N-diisopropylethylamine (0.44 mL, 2.5 mmol) and 2-chloro-4-methyl-6-(trifluoromethyl)pyridine-3-carboxylic acid (22) (300 mg, 1.25 mmol) at room temperature.

The resulting mixture was stirred at room temperature for 72 hours. The solvent was removed under reduced pressure and the residual material diluted with ethyl acetate (30 mL). The organic layer was washed with brine (30 mL), sat aq. NaHCO$_3$ (30 mL), dried over MgSO$_4$ and concentrated under reduced pressure to give a light orange oil. The crude was dissolved in DCM (20 mL) and washed with brine (15 mL). The organic layer was dried (MgSO$_4$) and the solvent was concentrated under reduced pressure to leave an orange solid. The crude material was purified by column chromatography (SiO$_2$, 10 g, gradient elution 10% EtOAc in petrol to 50% EtOAc in petrol). The desired fractions were combined and concentrated under reduced pressure to afford the title compound a white solid (84 mg, 26%); $^1$H NMR (500 MHz, Chloroform-d) δ 7.48 (s, 1H), 5.89 (s, 1H), 3.06 (d, J=4.9 Hz, 3H), 2.46 (s, 3H); LCMS (4 minute method) product at R$_t$=0.79 min and ES$^+$ m/z 253.09 [M+H]$^+$

[4-Chloro-2-(trifluoromethyl)pyrimidin-5-yl]methanol (25)

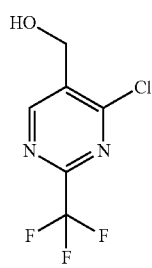

To a solution of ethyl-4-chloro-2-(trifluoromethyl)pyrimidin-5-carboxylate (24) (510 mg, 2.0 mmol) in DCM (10 mL) at 0° C. was added diisobutylaluminum hydride (1 M solution in toluene) (6.0 mL, 6.0 mmol). The mixture was slowly allowed to warm to room temperature and was stirred overnight. The reaction mixture was quenched with sat. aq. Rochelle's salt and stirred for 30 min before concentrating down the solution. The product was then extracted into EtOAc (3×30 mL) and the combined organic layers were washed with brine (50 mL), dried (MgSO$_4$) and solvent evaporated to leave a clear oil. The crude was purified by column chromatography (SiO$_2$, 10 g, gradient elution 10% EtOAc in petrol to 50% EtOAc in petrol). The desired fractions were concentrated under reduced pressure to afford the title compound as a yellow oil (96 mg, 23%); $^1$H NMR (500 MHz, Chloroform-d) δ 9.01 (s, 1H), 4.92 (s, 2H); LCMS (4 minute method) product at R$_t$=0.44 min and ES$^+$ m/z the desired mass ion was not observed.

[2-Chloro-6-(trifluoromethyl)-3-pyridyl]methanol (27)

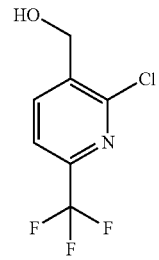 [SMILES: OCc1ccc(C(F)(F)F)nc1Cl]

To a solution of 2-chloro-6-(trifluoromethyl)pyridine-3-carboxylic acid (26) (1.07 g, 4.74 mmol) in tetrahydrofuran (15 mL) at 0° C. was added borane (1.0 M in tetrahydrofuran) (9.49 mL, 9.49 mmol) dropwise and the mixture was slowly allowed to warm up to room temperature and stirred overnight. Borane (1.0 M in tetrahydrofuran) (3.0 mL, 3.0 mmol) was added to the reaction mixture and stirred further for 16 hours. The reaction mixture was quenched with methanol (0.2 mL) and stirred for 30 min before concentrating down the solution. The residue was then diluted with water (30 mL) and extracted into EtOAc (3×30 mL). The combined organic layers were washed with brine (50 mL), dried (MgSO$_4$) and solvent evaporated to leave a clear oil. The crude material was purified by column chromatography (SiO$_2$, 25 g, gradient elution 10% EtOAc in petrol to 50% EtOAc in petrol). The desired fractions were concentrated to dryness under reduced pressure to afford the title compound as a colourless oil (1.02 g, 100%); $^1$H NMR (500 MHz, Chloroform-d) δ 8.11 (d, J=7.6 Hz, 1H), 7.68 (d, J=7.8 Hz, 1H), 4.86 (s, 2H); LCMS (4 minute method) product at R$_t$=0.62 min and ES$^+$ m/z the desired mas ion was not observed.

2-Chloro-4-methyl-6-(trifluoromethyl)pyridine-3-carbonitrile (29)

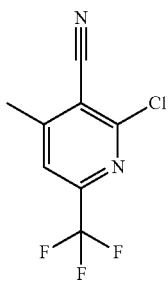

A mixture of 2-hydroxy-4-methyl-6-(trifluoromethyl)nicotinonitrile (28) (200 mg, 0.99 mmol) and phenyl dichlorophosphate (0.52 mL, 3.46 mmol) was heated under microwave irradiation for 30 min at 170° C. The reaction mixture was poured into ice, stirred for 20 min and diluted with ethyl acetate (20 mL). The pH was adjusted to 10, by addition of sat. aq. NaHCO$_3$. The organic layer was separated, washed with brine (20 mL), dried over MgSO$_4$ and concentrated under reduced pressure to afford the title compound as a clear oil (177 mg, 77%); $^1$H NMR (500 MHz, Chloroform-d) δ 7.60 (s, 1H), 2.71 (s, 3H); LCMS (4 minute method) product at R$_t$=0.60 min and ES$^+$ m/z the desired mas ion was not observed.

Example 1: 1-[[4-[5-(Hydroxymethyl)-6-(trifluoromethyl)-2-pyridyl]phenyl]methyl]pyrrolidin-2-one (32)

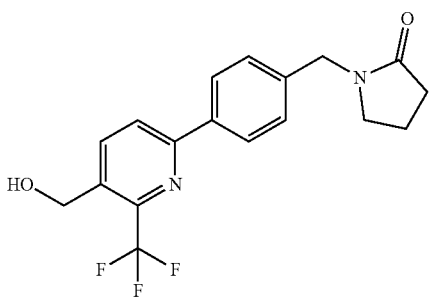 [SMILES: O=C1CCCN1Cc1ccc(-c2ccc(CO)c(C(F)(F)F)n2)cc1]

A mixture of 1-[[4-(4,4,5,5-tetramethyl-1,3,2-dioxaborolan-2-yl)phenyl]methyl]pyrrolidin-2-one (8) (334 mg, 1.11 mmol), bis(triphenylphosphine)palladium(II) dichloride (38 mg, 0.055 mmol), [6-chloro-2-(trifluoromethyl)-3-pyridyl]methanol (17) (235 mg, 1.11 mmol) and sodium carbonate (353 mg, 3.33 mmol) in acetonitrile (15 mL) and water (1 mL) was degassed under a flow of nitrogen and heated in a microwave reactor at 140° C. for 20 min. The reaction was diluted with water (30 mL) and extracted into EtOAc (2×30 mL). The combined organic extracts were dried (MgSO$_4$), filtered and evaporated under reduced pressure to give a beige solid (400 mg) which was purified by column chromatography (12 g, silica) gradient elution 80% EtOAc in petrol to 100% EtOAc. The desired fractions were concentrated to dryness under reduced pressure to afford the title compound as a white solid (210 mg, 54%); $^1$H NMR (500 MHz, Chloroform-d) δ 8.17 (d, J=8.2 Hz, 1H), 8.03 (d, J=8.1 Hz, 2H), 7.93 (d, J=8.2 Hz, 1H), 7.36 (d, J=8.0 Hz, 2H), 4.97 (s, 2H), 4.52 (s, 2H), 3.29 (t, J=7.0 Hz, 2H), 2.47 (t, J=8.1 Hz, 2H), 2.01 (p, J=7.6 Hz, 2H); LCMS (4 minute method) product at R$_t$=1.67 min and ES$^+$ m/z 351.17 [M+H]$^+$ Example 2: 1-[[4-[3-(Hydroxymethyl)-4-methyl-6-(trifluoromethyl)-2-pyridyl]phenyl]methyl]pyrrolidin-2-one (33)

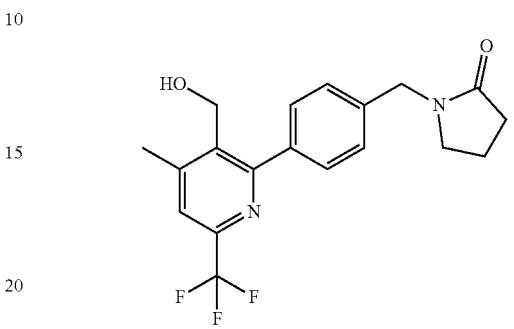

A mixture of 1-[[4-(4,4,5,5-tetramethyl-1,3,2-dioxaborolan-2-yl)phenyl]methyl]pyrrolidin-2-one (8) (200 mg, 0.66 mmol), bis(triphenylphosphine)palladium(II) dichloride (23 mg, 0.03 mmol), [2-chloro-4-methyl-6-(trifluoromethyl)-3-pyridyl]methanol (21) (149 mg, 0.66 mmol) and sodium carbonate (211 mg, 1.99 mmol) in acetonitrile (2 mL) and water (0.50 mL) was degassed under a flow of nitrogen and heated in a microwave reactor at 140° C. for 15 min. The reaction was diluted with water (10 mL) and extracted into EtOAc (2×20 mL). The combined organics were dried (MgSO$_4$), filtered and evaporated under reduced pressure to give a crude mixture which was purified by column chromatography (SiO$_2$, 4 g, gradient elution: 50% EtOAc in petrol to 100% EtOAc). The desired fractions were combined and concentrated to dryness under reduced pressure to afford the title compound as a white solid (85 mg, 35%); $^1$H NMR (500 MHz, Chloroform-d) δ 7.59 (d, J=8.2 Hz, 2H), 7.52 (s, 1H), 7.34 (d, J=8.1 Hz, 2H), 4.71 (s, 2H), 4.51 (s, 2H), 3.31 (t, J=7.1 Hz, 2H), 2.63 (s, 3H), 2.45 (t, J=8.1 Hz, 2H), 2.09-1.94 (m, 2H); LCMS (4 minute method) product at R$_t$=1.79 min and ES$^+$ m/z 365.10 [M+H]$^+$ Example 3: N,4-Dimethyl-2-[4-[(2-oxopyrrolidin-1-yl)methyl]phenyl]-6-(trifluoromethyl)pyridine-3-carboxamide (34)

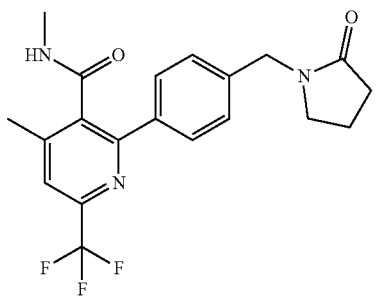 [SMILES: CNC(=O)c1c(C)cc(C(F)(F)F)nc1-c1ccc(CN2CCCC2=O)cc1]

A mixture of 1-[[4-(4,4,5,5-tetramethyl-1,3,2-dioxaborolan-2-yl)phenyl]methyl]pyrrolidin-2-one (8) (90 mg, 0.30 mmol), bis(triphenylphosphine)palladium(II) dichloride (10 mg, 0.010 mmol), 2-chloro-N,4-dimethyl-6-(trifluoromethyl)pyridine-3-carboxamide (23) (75 mg, 0.30 mmol) and sodium carbonate (95 mg, 0.90 mmol) in acetonitrile (8 mL) and water (2 mL) was degassed under a flow of nitrogen and heated in a microwave reactor at 145° C. for 20 min. The reaction was diluted with water (15 mL) and extracted into EtOAc (2×20 mL). The combined organic phases were dried (MgSO₄), filtered and concentrated under reduced pressure to give a crude mixture which was purified by column chromatography (10 g, silica) eluting with 10% EtOAc in petrol to 100% EtOAc. The desired fractions were combined and concentrated under reduced pressure to afford the title compound as a light yellow oil (51 mg, 41%); $^1$H NMR (500 MHz, Chloroform-d) δ 7.74 (d, J=8.2 Hz, 2H), 7.52 (s, 1H), 7.31 (d, J=8.0 Hz, 2H), 5.46 (q, J=5.0 Hz, 1H), 4.50 (s, 2H), 3.28 (t, J=7.0 Hz, 2H), 2.77 (d, J=4.9 Hz, 3H), 2.51 (s, 3H), 2.45 (t, J=8.1 Hz, 2H), 2.04-1.98 (m, 2H); LCMS (4 minute method) product at $R_t$=1.79 min and ES⁺ m/z 392.08 [M+H]⁺

Example 4: 1-[[4-[3-(Hydroxymethyl)-6-(trifluoromethyl)-2-pyridyl]phenyl]methyl]pyrrolidin-2-one (36)

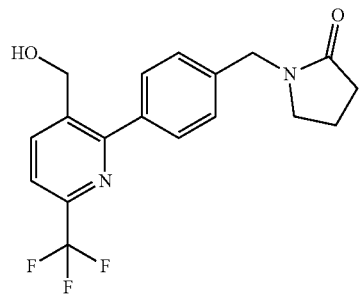

Split across two microwave vials was a mixture of 1-[[4-(4,4,5,5-tetramethyl-1,3,2-dioxaborolan-2-yl)phenyl]methyl]pyrrolidin-2-one (8) (245 mg, 0.81 mmol), bis(triphenylphosphine)palladium(II) dichloride (28.5 mg, 0.041 mmol), [2-chloro-6-(trifluoromethyl)-3-pyridyl]methanol (27) (172 mg, 0.81 mmol) and sodium carbonate (258 mg, 2.44 mmol) in acetonitrile (2 mL) and water (0.5 mL) was degassed under a flow of nitrogen and heated in a microwave reactor at 140° C. for 15 min. The reaction mixtures were combined, diluted with water (30 mL) and extracted into EtOAc (2×30 mL). The combined organic layers were dried (MgSO₄), filtered and evaporated under reduced pressure to give a crude mixture which was purified by column chromatography (10 g, silica) eluting with EtOAc:petrol 1:1 to 100% EtOAc. The desired fractions were concentrated to dryness under reduced pressure to afford the title compound as a colourless oil (268 mg, 94%); $^1$H NMR (500 MHz, Chloroform-d) δ 8.16 (d, J=8.0 Hz, 1H), 7.70 (d, J=8.0 Hz, 1H), 7.53 (d, J=7.9 Hz, 2H), 7.34 (d, J=7.9 Hz, 2H), 4.77 (s, 2H), 4.50 (s, 2H), 3.30 (t, J=7.1 Hz, 2H), 2.46 (t, J=8.1 Hz, 2H), 2.06-1.99 (m, 2H); LCMS (4 minute method) product at $R_t$=1.55 min and ES⁺ m/z 351.11 [M+H]⁺

Example 5: 4-Methyl-2-[4-[(2-oxopyrrolidin-1-yl)methyl]phenyl]-6-(trifluoromethyl)pyridine-3-carbonitrile (37)

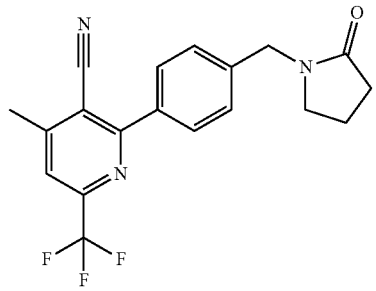 [SMILES: Cc1cc(C(F)(F)F)nc(-c2ccc(CN3CCCC3=O)cc2)c1C#N]

A mixture of 1-[[4-(4,4,5,5-tetramethyl-1,3,2-dioxaborolan-2-yl)phenyl]methyl]pyrrolidin-2-one (8) (165 mg, 0.55 mmol), bis(triphenylphosphine)palladium(II) dichloride (19.2 mg, 0.03 mmol), 2-chloro-4-methyl-6-(trifluoromethyl)pyridine-3-carbonitrile (29) (120 mg, 0.55 mmol) and sodium carbonate (174 mg, 1.64 mmol) in acetonitrile (8 mL) and water (2 mL) was degassed under a flow of nitrogen and heated in a microwave reactor at 140° C. for 15 min. The reaction was diluted with water (15 mL) and extracted into EtOAc (2×20 mL). The organics were dried (MgSO₄), filtered and evaporated under reduced pressure to give a crude mixture which was purified by column chromatography (10 g, silica) eluting with 10% EtOAc in petrol to 100% EtOAc. The desired fractions were combined and concentrated to dryness under reduced pressure to afford the title compound as a white solid (125 mg, 62%); $^1$H NMR (500 MHz, Chloroform-d) δ 7.93 (d, J=8.2 Hz, 2H), 7.62 (s, 1H), 7.42 (d, J=8.2 Hz, 2H), 4.55 (s, 2H), 3.32 (t, J=7.0 Hz, 2H), 2.75 (s, 3H), 2.48 (t, J=8.1 Hz, 2H), 2.10-1.96 (m, 2H); LCMS (4 minute method) product at $R_t$=2.33 min and ES⁺ m/z 360.10 [M+H]⁺

Example 6: 1-[[4-[5,6-Dimethyl-2-(trifluoromethyl)pyrimidin-4-yl]phenyl]methyl]pyrrolidin-2-one (38)

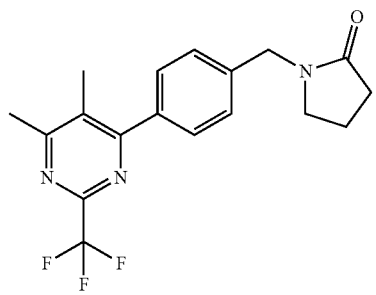 [SMILES: Cc1nc(C(F)(F)F)nc(-c2ccc(CN3CCCC3=O)cc2)c1C]

A mixture of 1-[[4-(4,4,5,5-tetramethyl-1,3,2-dioxaborolan-2-yl)phenyl]methyl]pyrrolidin-2-one (8) (100 mg, 0.33 mmol), bis(triphenylphosphine)palladium(II) dichloride (11.6 mg, 0.020 mmol), 4-chloro-5,6-dimethyl-2-(trifluoromethyl)pyrimidine (30) (70 mg, 0.33 mmol) and sodium carbonate (105 mg, 1.00 mmol) in acetonitrile (2 mL) and water (0.5 mL) was degassed under a flow of nitrogen and heated in a microwave reactor at 140° C. for 15 min. The reaction was diluted with water (30 mL), then extracted into EtOAc (2×30 mL). The combined organic layers were dried (MgSO$_4$), filtered and evaporated under reduced pressure to give a crude mixture which was purified twice by column chromatography (10 g, silica) eluting with EtOAc:petrol 1:1 to 100% EtOAc. The desired fractions were concentrated under reduced pressure to afford a colourless oil (56 mg). This oil was recrystallised from Et$_2$O/petrol to afford the title compound as a white solid (36 mg, 31%); $^1$H NMR (500 MHz, Chloroform-d) δ 7.55 (d, J=8.0 Hz, 2H), 7.38 (d, J=7.9 Hz, 2H), 4.53 (s, 2H), 3.32 (t, J=7.1 Hz, 2H), 2.67 (s, 3H), 2.47 (t, J=8.1 Hz, 2H), 2.38 (s, 3H), 2.04 (p, J=7.8 Hz, 2H); LCMS (4 minute method) product at R$_t$=2.29 min and ES$^+$ m/z 350.14 [M+H]$^+$ Example 7: 2-[4-[(2-Oxopyrrolidin-1-yl)methyl]phenyl]-6-(trifluoromethyl)pyridine-3-carbonitrile (39)

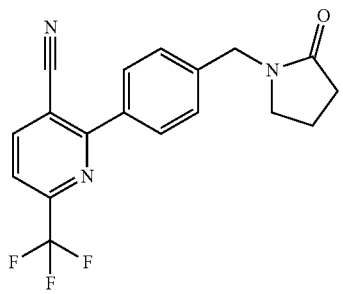 [SMILES: N#Cc1ccc(C(F)(F)F)nc1-c1ccc(CN2CCCC2=O)cc1]

A mixture of 1-[[4-(4,4,5,5-tetramethyl-1,3,2-dioxaborolan-2-yl)phenyl]methyl]pyrrolidin-2-one (8) (110 mg, 0.37 mmol), bis(triphenylphosphine)palladium(II) dichloride (13 mg, 0.020 mmol), 2-chloro-6-trifluoromethylnicotinonitrile (31) (75 mg, 0.37 mmol) and sodium carbonate (116 mg, 1.10 mmol) in acetonitrile (2 mL) and water (0.5 mL) was degassed under a flow of nitrogen and heated in a microwave reactor at 145° C. for 30 min. The reaction was diluted with water (10 mL) and extracted into EtOAc (2×20 mL). The combined organic layers were dried (MgSO$_4$), filtered and evaporated under reduced pressure to give a crude mixture which was purified by column chromatography (4 g, silica) eluting with 50% EtOAc in petrol to 100% EtOAc. The desired fractions were combined and concentrated to dryness under reduced pressure to afford the title compound as a clear oil (75 mg, 59%); $^1$H NMR (500 MHz, Chloroform-d) δ 8.27 (d, J=8.1 Hz, 1H), 7.99 (d, J=8.3 Hz, 2H), 7.74 (d, J=8.1 Hz, 1H), 7.43 (d, J=8.5 Hz, 2H), 4.55 (s, 2H), 3.32 (t, J=7.0 Hz, 2H), 2.47 (t, J=8.1 Hz, 2H), 2.10-2.00 (m, 2H); LCMS (4 minute method) product at R$_t$=2.17 min and ES$^+$ m/z 346.09 [M+H]$^+$ Example 8: 4-[[4-[5-(Hydroxymethyl)-6-(trifluoromethyl)-2-pyridyl]phenyl]methyl]morpholin-3-one (40)

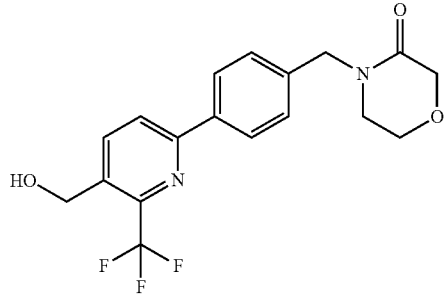 [SMILES: O=C1COCCN1Cc1ccc(-c2ccc(CO)c(C(F)(F)F)n2)cc1]

A mixture of 4-[[4-(4,4,5,5-tetramethyl-1,3,2-dioxaborolan-2-yl)phenyl]methyl]morpholin-3-one (9) (80 mg, 0.25 mmol), [6-chloro-2-(trifluoromethyl)-3-pyridyl]methanol (17) (59 mg, 0.28 mmol), sodium carbonate (80 mg, 0.76 mmol) and bis(triphenylphosphine)palladium(II) dichloride (8.9 mg, 0.010 mmol) in acetonitrile (4 mL) and water (1 mL) was heated in a microwave reactor at 140° C. for 15 min. The reaction was diluted with water (10 mL), the organic solvent was evaporated and the product was extracted into EtOAc (2×25 mL). The combined organic layers were washed with brine, (20 mL), dried (MgSO$_4$), filtered and evaporated under reduced pressure to give a crude residue which was purified twice by column chromatography (ISCO Combiflash, 4 g silica) eluting with EtOAc:petrol (50:50 to 100:0). The desired fractions were combined and concentrated to dryness under reduced pressure to afford the title compound as a white solid (27 mg, 29%); $^1$H NMR (500 MHz, Chloroform-d) δ 8.18 (d, J=8.1 Hz, 1H), 8.04 (d, J=7.8 Hz, 2H), 7.92 (d, J=8.3 Hz, 1H), 7.39 (d, J=7.8 Hz, 2H), 4.97 (s, 2H), 4.69 (s, 2H), 4.28 (s, 2H), 3.89-3.83 (m, 2H), 3.31 (t, J=5.0 Hz, 2H); LCMS (4 minute method) product at R$_t$=1.49 min and ES$^+$ m/z 367.22 [M+H]$^+$ Example 9: 4-[[4-[3-(Hydroxymethyl)-4-methyl-6-(trifluoromethyl)-2-pyridyl]phenyl]methyl]morpholin-3-one (41)

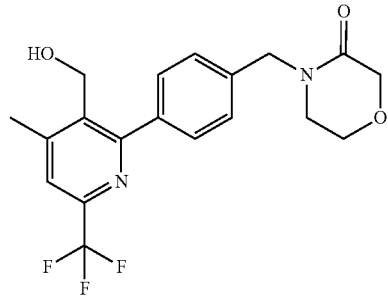 [SMILES: Cc1cc(C(F)(F)F)nc(-c2ccc(CN3CCOCC3=O)cc2)c1CO]

A mixture of 4-[[4-(4,4,5,5-tetramethyl-1,3,2-dioxaborolan-2-yl)phenyl]methyl]morpholin-3-one (9) (150 mg, 0.47 mmol), bis(triphenylphosphine)palladium(II) dichloride (16 mg, 0.02 mmol), [2-chloro-4-methyl-6-(trifluoromethyl)-3-pyridyl]methanol (21) (106 mg, 0.47 mmol) and sodium carbonate (150 mg, 1.42 mmol) in acetonitrile (2 mL) and water (0.50 mL) was degassed under a flow of nitrogen and heated in a microwave reactor at 140° C. for 15 min. The reaction was diluted with water (10 mL) and extracted into EtOAc (2×20 mL). The combined organic phases were dried (MgSO$_4$), filtered and evaporated under reduced pressure to give a crude mixture which was purified by column chromatography (SiO$_2$, 4 g; gradient elution 50% EtOAc in petrol to 100% EtOAc). The desired fractions were concentrated to dryness under reduced pressure to afford the title compound as a white solid (75 mg, 42%); $^1$H NMR (500 MHz, Chloroform-d) δ 7.61 (d, J=8.2 Hz, 2H), 7.52 (s, 1H), 7.37 (d, J=8.1 Hz, 2H), 4.70 (s, 2H), 4.68 (s, 2H), 4.25 (s, 2H), 3.90-3.82 (m, 2H), 3.36-3.27 (m, 2H), 2.63 (s, 3H); LCMS (4 minute method) product at R$_t$=0.40 min and ES$^+$ m/z 381.09 [M+H]$^+$ Example 10: 4-[[4-[3-(Hydroxymethyl)-6-(trifluoromethyl)-2-pyridyl]phenyl]methyl]morpholin-3-one (42)

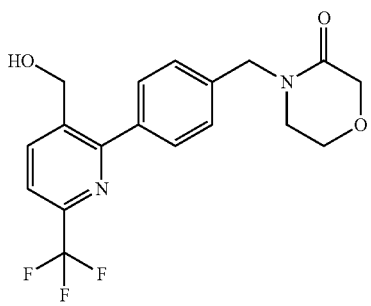 [SMILES: O=C1COCCN1Cc1ccc(-c2nc(C(F)(F)F)ccc2CO)cc1]

A mixture of 4-[[4-(4,4,5,5-tetramethyl-1,3,2-dioxaborolan-2-yl)phenyl]methyl]morpholin-3-one (9) (180 mg, 0.57 mmol), bis(triphenylphosphine)palladium(II) dichloride (20 mg, 0.030 mmol), [2-chloro-6-(trifluoromethyl)-3-pyridyl]methanol (27) (120 mg, 0.57 mmol) and sodium carbonate (180 mg, 1.70 mmol) in acetonitrile (2 mL) and water (0.5 mL) was degassed under a flow of nitrogen and heated in a microwave reactor at 140° C. for 15 min. The reaction was diluted with water (30 mL) and extracted into EtOAc (2×30 mL). The combined organic layers were dried (MgSO$_4$), filtered and evaporated under reduced pressure to give a crude mixture which was purified by column chromatography (10 g, silica) eluting with 100% EtOAc. The desired fractions were combined and concentrated to dryness under reduced pressure to afford the title compound as a colourless oil (119 mg, 57%); $^1$H NMR (500 MHz, Chloroform-d) δ 8.16 (d, J=8.0 Hz, 1H), 7.71 (d, J=8.0 Hz, 1H), 7.55 (d, J=8.1 Hz, 2H), 7.38 (d, J=7.9 Hz, 2H), 4.77 (s, 2H), 4.68 (s, 2H), 4.26 (s, 2H), 3.86 (t, J=5.1 Hz, 2H), 3.32 (t, J=5.2 Hz, 2H); LCMS (7 minute method) product at R$_t$=1.14 min and ES$^+$ m/z 367.10 [M+H]$^+$ Example 11: 2-[4-[(3-Oxomorpholin-4-yl)methyl]phenyl]-6-(trifluoromethyl)pyridine-3-carbonitrile (43)

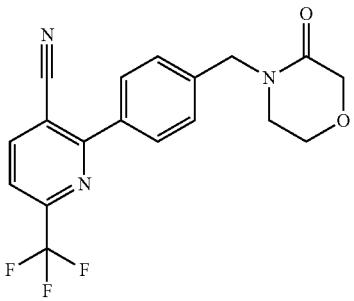 [SMILES: N#Cc1ccc(C(F)(F)F)nc1-c1ccc(CN2CCOCC2=O)cc1]

A mixture of 4-[[4-(4,4,5,5-tetramethyl-1,3,2-dioxaborolan-2-yl)phenyl]methyl]morpholin-3-one (9) (100 mg, 0.32 mmol), bis(triphenylphosphine)palladium(II) dichloride (11 mg, 0.020 mmol), 2-chloro-6-trifluoromethylnicotinonitrile (31) (65 mg, 0.32 mmol) and sodium carbonate (100 mg, 0.95 mmol) in acetonitrile (2 mL) and water (0.5 mL) was degassed under a flow of nitrogen and heated in a microwave reactor at 135° C. for 15 min. The reaction was diluted with water (10 mL) and extracted into EtOAc (2×20 mL). The combined organic layers were dried (MgSO$_4$), filtered and evaporated under reduced pressure to give a crude mixture which was purified by column chromatography (SiO$_2$, 10 g; gradient elution 100% petrol to 50% EtOAc in petrol). The desired fractions were combined and concentrated to dryness under reduced pressure to afford the title compound as a colourless oil which solidified upon standing (63 mg, 53%); R$_f$ 0.52 (1:1 ethyl acetate:petrol); $^1$H NMR (500 MHz, Chloroform-d) δ 8.28 (d, J=8.1 Hz, 1H), 7.99 (d, J=8.2 Hz, 2H), 7.75 (d, J=8.1 Hz, 1H), 7.46 (d, J=8.0 Hz, 2H), 4.71 (s, 2H), 4.28 (s, 2H), 3.87 (t, J=5.2 Hz, 2H), 3.33 (t, J=5.1 Hz, 2H); LCMS (7 minute method) product at R$_t$=3.11 min and ES$^+$ m/z 362.07 [M+H]$^+$ Example 12: 4-[[4-[3-(Hydroxymethyl)-4-methyl-6-(trifluoromethyl)-2-pyridyl]phenyl]methyl]-1,4-oxazepan-3-one (44)

A mixture of bis(triphenylphosphine)palladium(II) dichloride (11 mg, 0.020 mmol), sodium carbonate (99 mg, 0.93 mmol), 4-[[4-(4,4,5,5-tetramethyl-1,3,2-dioxaborolan-2-yl)phenyl]methyl]-1,4-oxazepan-3-one (10) (123 mg, 0.37 mmol) and [2-chloro-4-methyl-6-(trifluoromethyl)-3-pyridyl]methanol (21) (70 mg, 0.31 mmol) in acetonitrile (2 mL) and water (0.5 mL) was degassed under a flow of nitrogen and irradiated in a microwave reactor at 140° C. for 15 min. The reaction was diluted with water (30 mL), then extracted into EtOAc (2×30 mL). The combined organic layers were dried (MgSO$_4$), filtered and evaporated under reduced pressure to give a crude mixture which was purified by column chromatography (25 g, silica) eluting with EtOAc:petrol 1:1 to 100% EtOAc. The desired fractions were combined and concentrated to dryness under reduced pressure to afford the title compound as a colourless oil which solidified upon standing (110 mg, 87%); $^1$H NMR (500 MHz, Chloroform-d) δ 7.60 (d, J=8.1 Hz, 2H), 7.52 (s, 1H), 7.38 (d, J=8.1 Hz, 2H), 4.72 (s, 2H), 4.68 (s, 2H), 4.34 (s, 2H), 3.84 (t, J=5.9 Hz, 2H), 3.49-3.43 (m, 2H), 2.63 (s, 3H), 1.95-1.87 (m, 2H); LCMS (4 minute method) product at R$_t$=1.72 min and ES$^+$ m/z 395.12 [M+H]$^+$ Example 13: 4-[[4-[3-(Hydroxymethyl)-4-methyl-6-(trifluoromethyl)-2-pyridyl]phenyl]methyl]-1,4-oxazepan-5-one (45)

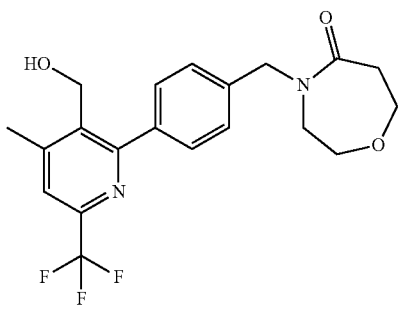 [SMILES: Cc1cc(C(F)(F)F)nc(-c2ccc(CN3CCOCCC3=O)cc2)c1CO]

A mixture of bis(triphenylphosphine)palladium(II) dichloride (11 mg, 0.02 mmol), sodium carbonate (99 mg, 0.93 mmol), 4-[[4-(4,4,5,5-tetramethyl-1,3,2-dioxaborolan-2-yl)phenyl]methyl]-1,4-oxazepan-5-one (11) (123 mg, 0.37 mmol) and [2-chloro-4-methyl-6-(trifluoromethyl)-3-pyridyl]methanol (21) (70 mg, 0.31 mmol) in acetonitrile (2 mL) and water (0.5 mL) was degassed under a flow of nitrogen and irradiated in a microwave reactor at 140° C. for 15 min. The reaction was diluted with water (30 mL), then extracted into EtOAc (2×30 mL). The combined organic layers were dried (MgSO$_4$), filtered and evaporated under reduced pressure to give a crude mixture which was purified by column chromatography (25 g, silica) eluting with EtOAc:petrol 1:1 to 100% EtOAc. The desired fractions were concentrated under reduced pressure to afford the title compound as a colourless oil which solidified on standing to a gummy white solid (104 mg, 85%);

$^1$H NMR (500 MHz, Chloroform-d) δ 7.60 (d, J=8.1 Hz, 2H), 7.52 (s, 1H), 7.35 (d, J=7.8 Hz, 2H), 4.71 (s, 2H), 4.67 (s, 2H), 3.88-3.78 (m, 2H), 3.69-3.62 (m, 2H), 3.50-3.40 (m, 2H), 2.91-2.79 (m, 2H), 2.63 (s, 3H); LCMS (4 minute method) product at R$_t$=1.66 min and ES$^+$ m/z 395.13 [M+H]$^+$ Example 14: 1-[[5-[3-(Hydroxymethyl)-4-methyl-6-(trifluoromethyl)-2-pyridyl]-2-pyridyl]methyl]pyrrolidin-2-one (46)

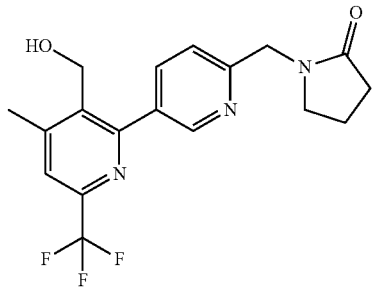 [SMILES: Cc1cc(C(F)(F)F)nc(-c2ccc(CN3CCCC3=O)nc2)c1CO]

A mixture of 1-[[5-(4,4,5,5-tetramethyl-1,3,2-dioxaborolan-2-yl)-2-pyridyl]methyl]pyrrolidin-2-one (12) (138 mg, 0.46 mmol), bis(triphenylphosphine)palladium(II) dichloride (16.0 mg, 0.02 mmol), [2-chloro-4-methyl-6-(trifluoromethyl)-3-pyridyl]methanol (21) (103 mg, 0.46 mmol) and sodium carbonate (145 mg, 1.37 mmol) in acetonitrile (2 mL) and water (0.5 mL) was degassed under a flow of nitrogen and heated in a microwave reactor at 140° C. for 15 min. The reaction was diluted with water (10 mL) and extracted into EtOAc (2×20 mL). The combined organic layers were dried (MgSO$_4$), filtered and evaporated under reduced pressure to give a crude mixture. The crude material was purified by column chromatography (4 g, silica) eluting with 50% EtOAc in PE to 100% EtOAc then 5% MeOH in EtOAc. The desired fractions were concentrated to dryness under reduced pressure to afford the title compound as a white solid (84 mg, 50%); $^1$H NMR (500 MHz, Chloroform-d) δ 8.90 (s, 1H), 8.11 (d, J=8.0 Hz, 1H), 7.57 (s, 1H), 7.45 (d, J=8.1 Hz, 1H), 4.71 (s, 4H), 3.48 (t, J=7.2, Hz, 2H), 2.65 (s, 3H), 2.47 (t, J=8.4 Hz, 2H), 2.14-2.04 (m, 2H); LCMS (4 minute method) product at R$_t$=1.07 min and ES$^+$ m/z 366.22 [M+H]$^+$ Example 15: 2-[6-[(2-Oxopyrrolidin-1-yl)methyl]-3-pyridyl]-6-(trifluoromethyl)pyridine-3-carbonitrile (48)

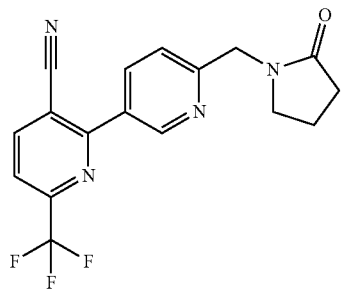

A flask containing 1-[(5-bromo-2-pyridyl)methyl]pyrrolidin-2-one (7) (1.0 g, 3.92 mmol), bis(pinacolato)diboron (1.19 g, 4.7 mmol) and potassium acetate (1.15 g, 11.8 mmol) in 1,4-dioxane (50 mL) was evacuated and charged with nitrogen 3 times. Pd(dppf)Cl$_2$ (143 mg, 0.20 mmol) was added and the reaction mixture was heated at 95° C. for 26 hours. The reaction mixture was allowed to cool to room temperature 2-chloro-6-trifluoromethylnicotinonitrile (31) (810 mg, 3.92 mmol), sodium carbonate (1.25 g, 11.8 mmol), Pd(dppf)Cl₂ (143 mg, 0.20 mmol) and water (10 mL) were added and reaction flask was evacuated and charged with nitrogen 3 times. The reaction mixture was heated at 95° C. for 3 hours. The reaction mixture was allowed to cool to room temperature where it was diluted with brine (50 mL) and extracted with ethyl acetate (3×100 mL). The combined organic extracts were dried over magnesium sulfate, filtered and concentrated under reduced pressure. The residue was purified by flash column chromatography (40 g silica, petrol:EtOAc, 100:0 to 0:100). The desired fractions were concentrated under reduced pressure to afford the title compound as a pale yellow oil that solidified upon standing to give a beige solid (1.2 g, 84%); R_f 0.17 (100% ethyl acetate); ¹H NMR (500 MHz, Chloroform-d) δ 9.18 (d, J=2.3 Hz, 1H), 8.36-8.27 (m, 2H), 7.82 (d, J=8.2 Hz, 1H), 7.47 (d, J=8.1 Hz, 1H), 4.71 (s, 2H), 3.49 (t, J=7.1 Hz, 2H), 2.50 (t, J=8.1 Hz, 2H), 2.09 (p, J=7.6 Hz, 2H); LCMS (4 minute method) product at R_t=1.78 min and ES⁺ m/z 347.23 [M+H]⁺

Example 16: 1-[[4-[5-(Fluoromethyl)-6-(trifluoromethyl)-2-pyridyl]phenyl]methyl]pyrrolidin-2-one (49)

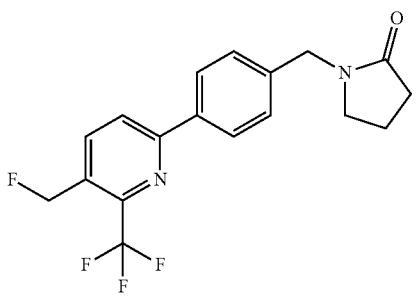 [SMILES: O=C1CCCN1Cc1ccc(-c2ccc(CF)c(C(F)(F)F)n2)cc1]

To 1-[[4-[5-(hydroxymethyl)-6-(trifluoromethyl)-2-pyridyl]phenyl]methyl]pyrrolidin-2-one (32) (80 mg, 0.23 mmol) in dichloromethane (4 mL), cooled in an ice bath, was added [bis(2-methoxyethyl)amino]sulphur trifluoride (50 wt % solution in toluene) (84 μL, 0.46 mmol) dropwise. The reaction was slowly warmed to room temperature and stirred for 2 hours. More [bis(2-methoxyethyl)amino]sulphur trifluoride (50 wt % solution in toluene) (84 μL, 0.46 mmol) was added and the reaction mixture stirred for another 2 hours. The reaction mixture was cooled in an ice bath and quenched by addition of sat. aq. NaHCO₃ (5 mL), the layers were separated and the aqueous layer extracted with DCM (2×10 mL). The combined organic layers were washed with brine (30 mL), dried over MgSO₄ and concentrated under reduced pressure. The crude product was purified by column chromatography on silica (10% EtOAc in petrol to 100% EtOAc). The desired fractions were concentrated under reduced pressure to afford the title compound as a white solid (43 mg, 49%); ¹H NMR (500 MHz, Chloroform-d) δ 8.08 (d, J=8.4 Hz, 1H), 8.04 (d, J=7.9 Hz, 2H), 7.96 (d, J=8.3 Hz, 1H), 7.38 (d, J=7.9 Hz, 2H), 5.67 (d, J=46.7 Hz, 2H), 4.52 (s, 2H), 3.29 (t, J=7.0 Hz, 2H), 2.47 (t, J=8.1 Hz, 2H), 2.07-1.96 (m, 2H); LCMS (4 minute method) product at R_t=2.58 min and ES⁺ m/z 353.11 [M+H]⁺

Example 17: 1-[[4-[3-(Fluoromethyl)-4-methyl-6-(trifluoromethyl)-2-pyridyl]phenyl]methyl]pyrrolidin-2-one (50)

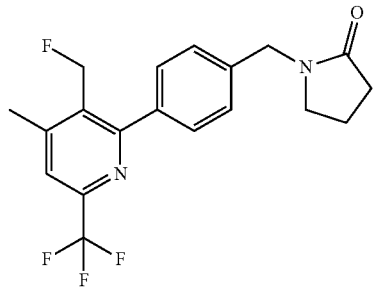 [SMILES: Cc1cc(C(F)(F)F)nc(-c2ccc(CN3CCCC3=O)cc2)c1CF]

To a solution of 1-[[4-[3-(hydroxymethyl)-4-methyl-6-(trifluoromethyl)-2-pyridyl]phenyl]methyl]pyrrolidin-2-one (33) (66 mg, 0.18 mmol) in DCM (4 mL) at 0° C. was added [bis(2-methoxyethyl)amino]sulphur trifluoride (50 wt % solution in toluene) (100 μL, 0.54 mmol). The reaction was slowly warmed to room temperature and stirred overnight. [Bis(2-methoxyethyl)amino]sulphur trifluoride (50 wt % solution in toluene) (52 μL, 0.28 mmol) was added and the mixture stirred for 2 hours. The reaction mixture was quenched by addition of sat. aq. NaHCO₃ (5 mL) and the layers were separated using a phase separator. The organic layer was concentrated under reduced pressure and the crude product was purified by column chromatography (SiO₂, 4 g, gradient elution: 10% EtOAc in petrol to 100% EtOAc). The desired fractions were concentrated to dryness under reduced pressure to afford the title compound as a white solid (47 mg, 71%); ¹H NMR (500 MHz, Chloroform-d) δ 7.57 (d, J=8.3 Hz, 2H), 7.55 (s, 1H), 7.36 (d, J=8.3 Hz, 2H), 5.43 (d, J=48.0 Hz, 2H), 4.53 (s, 2H), 3.31 (t, J=7.1 Hz, 2H), 2.63 (s, 3H), 2.47 (t, J=8.2 Hz, 2H), 2.13-1.88 (m, 2H); LCMS (4 minute method) product at R_t=2.58 min and ES⁺ m/z 367.08 [M+H]⁺

Example 18: 1-[[4-[5-(Fluoromethyl)-2-(trifluoromethyl)pyrimidin-4-yl]phenyl]methyl]pyrrolidin-2-one (51)

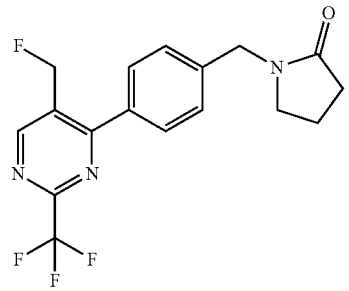 [SMILES: O=C1CCCN1Cc1ccc(-c2nc(C(F)(F)F)ncc2CF)cc1]

To 1-[[4-[5-(hydroxymethyl)-2-(trifluoromethyl)pyrimidin-4-yl]phenyl]methyl]pyrrolidin-2-one (35) (62 mg, 0.18 mmol) in DCM (4 mL), cooled in an ice bath, was added [bis(2-methoxyethyl)amino]sulphur trifluoride (50 wt % solution in toluene) (65 μL, 0.35 mmol) dropwise. The reaction was slowly warmed to room temperature and stirred for 3 days. The reaction mixture was cooled in an ice bath and quenched by addition of sat. aq. NaHCO₃ (5 mL), the layers were separated and the aqueous layer was extracted with DCM (2×10 mL). The combined organic layers were washed with brine (30 mL), dried over MgSO₄ and concentrated under reduced pressure. The crude product was purified by column chromatography on silica (petrol:EtOAc, gradient 10:90 to 0:100). The desired fractions were concentrated under reduced pressure to afford the title compound as a white solid (61 mg, 98%); $^1$H NMR (500 MHz, Chloroform-d) δ 9.06 (s, 1H), 7.69 (d, J=8.1 Hz, 2H), 7.44 (d, J=8.2 Hz, 2H), 5.53 (d, J=47.2 Hz, 2H), 4.55 (s, 2H), 3.33 (t, J=7.1 Hz, 2H), 2.48 (t, J=8.1 Hz, 2H), 2.05 (p, J=7.6 Hz, 2H); LCMS (4 minute method) product at R$_t$=2.11 min and ES⁺ m/z 354.12 [M+H]⁺

The starting material, 1-[[4-[5-(hydroxymethyl)-2-(trifluoromethyl)pyrimidin-4-yl]phenyl]methyl]pyrrolidin-2-one (35) was prepared as follows:

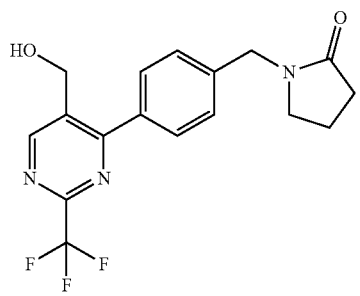 [SMILES: O=C1CCCN1Cc1ccc(-c2nc(C(F)(F)F)ncc2CO)cc1]

(35)

A mixture of 1-[[4-(4,4,5,5-tetramethyl-1,3,2-dioxaborolan-2-yl)phenyl]methyl]pyrrolidin-2-one (8) (130 mg, 0.43 mmol), bis(triphenylphosphine)palladium(II) dichloride (15 mg, 0.02 mmol), [4-chloro-2-(trifluoromethyl)pyrimidin-5-yl]methanol (25) (92 mg, 0.43 mmol) and sodium carbonate (137 mg, 1.29 mmol) in acetonitrile (2 mL) and water (0.5 mL) was degassed under a flow of nitrogen and heated in a microwave reactor in at 140° C. for 15 min. The reaction was diluted with water (30 mL) and extracted into EtOAc (2×30 mL). The combined organic layers were dried (MgSO₄), filtered and evaporated under reduced pressure to give a crude mixture which was purified by column chromatography (10 g, silica) eluting with 100% EtOAc. The desired fractions were concentrated under reduced pressure to afford the title compound as a white solid (85 mg, 56%); $^1$H NMR (500 MHz, Chloroform-d) δ 9.11 (s, 1H), 7.70 (d, J=8.2 Hz, 2H), 7.40 (d, J=8.0 Hz, 2H), 4.88 (s, 2H), 4.53 (s, 2H), 3.32 (t, J=7.1 Hz, 2H), 2.47 (t, J=8.2 Hz, 2H), 2.04 (p, J=7.7 Hz, 2H); LCMS (7 minute method) product at R$_t$=2.32 min and ES⁺ m/z 352.04 [M+H]⁺

Example 19: 1-[[4-[3-(Fluoromethyl)-6-(trifluoromethyl)-2-pyridyl]phenyl]methyl]pyrrolidin-2-one (52)

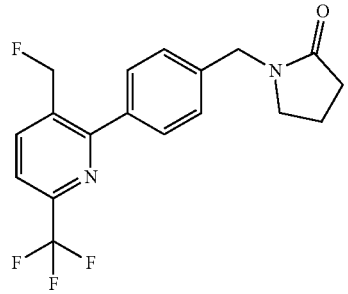 [SMILES: O=C1CCCN1Cc1ccc(-c2nc(C(F)(F)F)ccc2CF)cc1]

To 1-[[4-[3-(hydroxymethyl)-6-(trifluoromethyl)-2-pyridyl]phenyl]methyl]pyrrolidin-2-one (36) (102 mg, 0.29 mmol) in DCM (4 mL), cooled in an ice bath, was added [bis(2-methoxyethyl)amino]sulphur trifluoride (50 wt % solution in toluene) (107 µL, 0.58 mmol) dropwise. The reaction was slowly warmed to room temperature and stirred for 3 days. The reaction mixture was cooled in an ice bath and quenched by addition of sat. aq. NaHCO₃ (5 mL), the layers were separated and the aqueous layer extracted with DCM (2×10 mL). The combined organic layers were washed with brine (30 mL), dried over MgSO₄ and concentrated under reduced pressure. The crude product was purified by column chromatography on silica (petrol:EtOAc, 1:1 to 100% EtOAc). The desired fractions were concentrated to dryness under reduced pressure to afford the title compound as a colourless oil (74 mg, 72%); $^1$H NMR (500 MHz, Chloroform-d) δ 8.10 (d, J=8.1 Hz, 1H), 7.73 (d, J=8.0 Hz, 1H), 7.54 (d, J=7.4 Hz, 2H), 7.38 (d, J=7.8 Hz, 2H), 5.45 (d, J=47.3 Hz, 2H), 4.53 (s, 2H), 3.31 (t, J=6.7 Hz, 2H), 2.47 (t, J=8.1 Hz, 2H), 2.03 (p, J=7.5 Hz, 2H); LCMS (7 minute method) product at R$_t$=3.26 min and ES⁺ m/z 353.07 [M+H]⁺

Example 20: 4-[[4-[3-(Fluoromethyl)-4-methyl-6-(trifluoromethyl)-2-pyridyl]phenyl]methyl]morpholin-3-one (53)

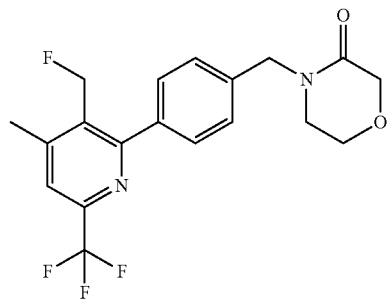 [SMILES: Cc1cc(C(F)(F)F)nc(-c2ccc(CN3CCOCC3=O)cc2)c1CF]

To a solution of 4-[[4-[3-(hydroxymethyl)-4-methyl-6-(trifluoromethyl)-2-pyridyl]phenyl]methyl]morpholin-3-one (41) (40 mg, 0.11 mmol) in DCM (4 mL) at 0° C. was added [bis(2-methoxyethyl)amino]sulphur trifluoride (50 wt % solution in toluene) (58 µL, 0.32 mmol). The reaction was slowly warmed to room temperature and stirred overnight. More [bis(2-methoxyethyl)amino]sulphur trifluoride (50 wt % solution in toluene) (30 µL, 0.16 mmol) was added and the reaction was stirred for another 2 hours. The reaction mixture was quenched by addition of sat. aq. NaHCO₃ (5 mL), the layers were separated using a phase separator and the organic layer was concentrated under reduced pressure. The crude product was purified by column chromatography (SiO₂, 4 g, gradient elution: 10% EtOAc in petrol to 100% EtOAc). The desired fractions were concentrated to dryness under reduced pressure to afford the title compound as a white solid (25 mg, 62%); ¹H NMR (500 MHz, Chloroform-d) δ 7.62-7.57 (d, J=7.7 Hz, 2H), 7.56 (s, 1H), 7.40 (d, J=7.7 Hz, 2H), 5.43 (d, J=47.6 Hz, 2H), 4.70 (s, 2H), 4.27 (s, 2H), 3.87 (t, J=5.4 Hz, 2H), 3.33 (t, J=5.2 Hz, 2H), 2.63 (s, 3H); LCMS (4 minute method) product at $R_t$=2.44 min and ES⁺ m/z 383.10 [M+H]⁺

Example 21: 4-[[4-[3-(Fluoromethyl)-6-(trifluoromethyl)-2-pyridyl]phenyl]methyl]morpholin-3-one (54)

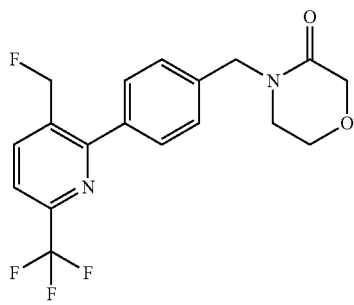 [SMILES: O=C1COCCN1Cc1ccc(-c2nc(C(F)(F)F)ccc2CF)cc1]

To 4-[[4-[3-(hydroxymethyl)-6-(trifluoromethyl)-2-pyridyl]phenyl]methyl]morpholin-3-one (42) (80 mg, 0.22 mmol) in DCM (4 mL), cooled in an ice bath, was added [bis(2-methoxyethyl)amino]sulphur trifluoride (50 wt % solution in toluene) (243 µL, 0.66 mmol) dropwise. The reaction was slowly warmed to room temperature and stirred for 3 days. The reaction mixture was cooled in an ice bath and quenched by addition of sat. aq. NaHCO₃ (5 mL), the layers were separated and the aqueous layer extracted with DCM (2×10 mL). The combined organic layers were washed with brine (30 mL), dried over MgSO₄ and concentrated under reduced pressure. The crude product was purified by column chromatography on silica (50% EtOAc in petrol to 100% EtOAc). The desired fractions were combined and concentrated to dryness under reduced pressure to afford the title compound as a colourless oil (74 mg, 92%); $R_f$ 0.28 (1:1 ethyl acetate:petrol); ¹H NMR (500 MHz, Chloroform-d) δ 8.10 (d, J=8.0 Hz, 1H), 7.73 (d, J=8.1 Hz, 1H), 7.55 (d, J=8.2 Hz, 2H), 7.41 (d, J=7.9 Hz, 2H), 5.45 (d, J=47.2 Hz, 2H), 4.70 (s, 2H), 4.27 (s, 2H), 3.87 (t, J=5.2 Hz, 2H), 3.32 (t, J=5.1 Hz, 2H); LCMS (4 minute method) product at $R_t$=0.56 min and ES⁺ m/z 369.07 [M+H]⁺

Example 22: 1-[[5-[3-(Fluoromethyl)-4-methyl-6-(trifluoromethyl)-2-pyridyl]-2-pyridyl]methyl]pyrrolidin-2-one (55)

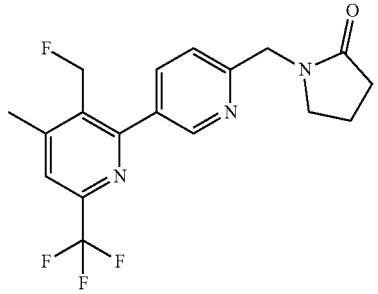 [SMILES: Cc1cc(C(F)(F)F)nc(-c2ccc(CN3CCCC3=O)nc2)c1CF]

To a solution of 1-[[5-[3-(hydroxymethyl)-4-methyl-6-(trifluoromethyl)-2-pyridyl]-2-pyridyl]methyl]pyrrolidin-2-one (46) (70 mg, 0.19 mmol) in DCM (4 mL) at 0° C. was added [bis(2-methoxyethyl)amino]sulphur trifluoride (50 wt % solution in toluene) (70 µL, 0.38 mmol). The reaction was slowly warmed to room temperature and stirred overnight. The reaction mixture was cooled in an ice bath and quenched by addition of sat. aq. NaHCO₃ (5 mL), the layers were separated and the aqueous layer extracted with DCM (2×10 mL). The combined organic layers were washed with brine (30 mL), dried over MgSO₄ and concentrated under reduced pressure. The crude product was purified by column chromatography (SiO₂, 4 g, gradient elution: 50% EtOAc in petrol to 100% EtOAc). The desired fractions were concentrated to dryness under reduced pressure to afford the title compound as a white solid (30 mg, 43%); ¹H NMR (500 MHz, Chloroform-d) δ 8.79 (d, J=2.3 Hz, 1H), 7.98 (dd, J=8.0, 2.2 Hz, 1H), 7.61 (s, 1H), 7.44 (d, J=8.0 Hz, 1H), 5.42 (d, J=47.6 Hz, 2H), 4.70 (s, 2H), 3.48 (t, J=7.1 Hz, 2H), 2.65 (s, 3H), 2.48 (t, J=8.1 Hz, 2H), 2.08 (p, J=7.2 Hz, 2H); LCMS (4 minute method) product at $R_t$=1.71 min and ES⁺ m/z 368.22 [M+H]⁺

Example 23: 1-[[5-[3-(Fluoromethyl)-6-(trifluoromethyl)-2-pyridyl]-2-pyridyl]methyl]pyrrolidin-2-one (56)

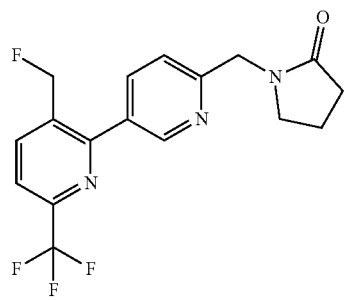 [SMILES: O=C1CCCN1Cc1ccc(-c2nc(C(F)(F)F)ccc2CF)cn1]

To 1-[[5-[3-(hydroxymethyl)-6-(trifluoromethyl)-2-pyridyl]-2-pyridyl]methyl]pyrrolidin-2-one (47) (44 mg, 0.13 mmol) in DCM (4 mL), cooled in an ice bath, was added [bis(2-methoxyethyl)amino]sulphur trifluoride (50 wt % solution in toluene) (46 µL, 0.25 mmol) dropwise. The reaction was slowly warmed to room temperature and stirred for 3 days. The reaction mixture was cooled in an ice bath and quenched by addition of sat. aq. NaHCO₃ (5 mL), the layers were separated and the aqueous layer extracted with DCM (2×10 mL). The combined organic layers were washed with brine (30 mL), dried over MgSO₄ and concentrated under reduced pressure. The crude product was purified by column chromatography on silica (petrol:EtOAc, gradient 10:90 to 0:100). The desired fractions were combined and concentrated to dryness under reduced pressure to afford the title compound as a colourless oil (28 mg, 63%); ¹H NMR (500 MHz, Chloroform-d) δ 8.79 (d, J=8.1 Hz, 1H), 8.14 (d, J=8.1 Hz, 1H), 7.99 (dd, J=7.9, 2.3 Hz, 1H), 7.79 (d, J=8.0 Hz, 1H), 7.46 (d, J=7.8 Hz, 1H), 5.46 (d, J=47.2 Hz, 2H), 4.71 (s, 2H), 3.49 (t, J=7.1 Hz, 2H), 2.48 (t, J=8.1 Hz, 2H), 2.13-2.03 (m, 2H); LCMS (4 minute method) product at $R_t$=1.63 min and ES⁺ m/z 354.22 [M+H]⁺

The starting material 1-[[5-[3-(Hydroxymethyl)-6-(trifluoromethyl)-2-pyridyl]-2-pyridyl]methyl]pyrrolidin-2-one (47) was prepared as follows:

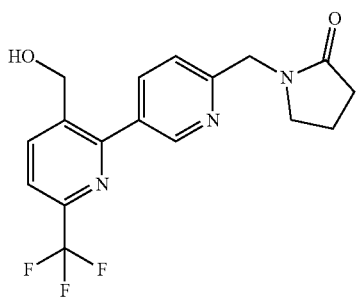 [SMILES: O=C1CCCN1Cc1ccc(-c2nc(C(F)(F)F)ccc2CO)cn1]

(47)

A mixture of 1-[[5-(4,4,5,5-tetramethyl-1,3,2-dioxaborolan-2-yl)-2-pyridyl]methyl]pyrrolidin-2-one (12) (95 mg, 0.31 mmol), bis(triphenylphosphine)palladium(II) dichloride (11 mg, 0.020 mmol), [2-chloro-6-(trifluoromethyl)-3-pyridyl]methanol (27) (66 mg, 0.31 mmol) and sodium carbonate (100 mg, 0.94 mmol) in acetonitrile (2 mL) and water (0.5 mL) was degassed under a flow of nitrogen and heated in a microwave reactor at 140° C. for 15 min. The reaction was diluted with water (30 mL) and extracted into EtOAc (2×30 mL). The combined organic layers were dried (MgSO₄), filtered and evaporated under reduced pressure to give a crude mixture which was purified by column chromatography (10 g, silica) eluting with MeOH:EtOAc (0:100 to 5:95). The desired fractions were combined and concentrated to dryness under reduced pressure to afford the title compound as a colourless oil which solidified on standing to an off-white solid (59 mg, 53%); ¹H NMR (500 MHz, Chloroform-d) δ 8.79 (s, 1H), 8.20 (d, J=8.0 Hz, 1H), 8.00 (dd, J=8.3, 2.2 Hz, 1H), 7.75 (d, J=8.1 Hz, 1H), 7.42 (d, J=8.1 Hz, 1H), 4.78 (s, 2H), 4.68 (s, 2H), 3.47 (t, J=7.1 Hz, 2H), 2.48 (t, J=8.1 Hz, 2H), 2.13-2.04 (m, 2H); LCMS (4 minute method) product at $R_t$=0.58 min and ES⁺ m/z 352.23 [M+H]⁺

Example 24: 4-Methyl-2-[4-[(3-oxomorpholin-4-yl)methyl]phenyl]-6-(trifluoromethyl)pyridine-3-carbonitrile (57)

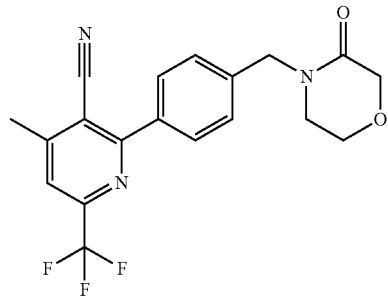 [SMILES: Cc1cc(C(F)(F)F)nc(-c2ccc(CN3CCOCC3=O)cc2)c1C#N]

To a solution of 4-[[4-[3-(hydroxymethyl)-4-methyl-6-(trifluoromethyl)-2-pyridyl]phenyl]methyl]morpholin-3-one (41) (30 mg, 0.079 mmol) in acetonitrile (0.45 mL) and water (0.050 mL) was added (diacetoxyiodo)benzene (55 mg, 0.17 mmol), TEMPO (0.62 mg, 0.0039 mmol) and ammonium acetate (24 mg, 0.32 mmol). The reaction mixture was stirred at room temperature for 18 hours before being concentrated under reduced pressure. The reaction mixture was diluted with deionised water (10 mL) and extracted with ethyl acetate (3×10 mL). The combined organic extracts were dried over MgSO₄, filtered and concentrated under reduced pressure. The residue was purified by flash column chromatography (5 g silica, petrol:EtOAc, 100:0 to 0:100). The desired fractions were concentrated under reduced pressure to afford the title compound as a yellow oil (15 mg, 48%); $R_f$ 0.24 (1:1 ethyl acetate:petrol); ¹H NMR (500 MHz, Chloroform-d) δ 7.95 (d, J=8.2 Hz, 2H), 7.63 (s, 1H), 7.46 (d, J=8.2 Hz, 2H), 4.72 (s, 2H), 4.29 (s, 2H), 3.94-3.81 (m, 2H), 3.38-3.26 (m, 2H), 2.75 (s, 3H); LCMS (4 minute method) product at $R_t$=0.57 min and ES⁺ m/z 376.06 [M+H]⁺

Example 25: 1-[[4-[4-(Hydroxymethyl)-6-(trifluoromethyl)-2-pyridyl]phenyl]methyl]pyrrolidin-2-one (61)

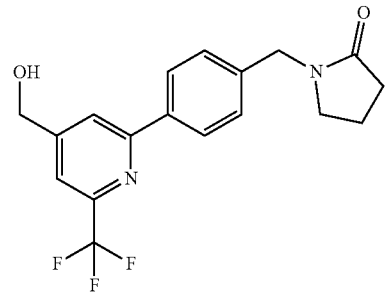 [SMILES: O=C1CCCN1Cc1ccc(-c2cc(CO)cc(C(F)(F)F)n2)cc1]

To a solution of 2-[4-[(2-oxopyrrolidin-1-yl)methyl]phenyl]-6-(trifluoromethyl)pyridine-4-carbaldehyde (60) (38 mg, 0.11 mmol) in methyl alcohol (2 mL) at room temperature was added sodium borohydride (10 mg, 0.26 mmol). The reaction mixture was stirred at room temperature for 3 hours before being concentrated under reduced pressure. The residue was dissolved in deionised water (3 mL) and DCM (3 mL). The phases were separated and the aqueous phase was extracted with DCM (3×5 mL). The combined organic extracts were dried over magnesium sulfate, filtered and concentrated under reduced pressure. The residue was purified by flash column chromatography (5 g silica, EtOAc:MeOH, 100:0 to 95:5). The desired fractions were concentrated under reduced pressure to afford the title compound as a white solid (10 mg, 25%); $R_f$ 0.14 (100% ethyl acetate); $^1$H NMR (500 MHz, Chloroform-d) δ 8.01 (d, J=8.2 Hz, 2H), 7.89 (s, 1H), 7.61 (s, 1H), 7.33 (d, J=8.1 Hz, 2H), 4.88 (d, J=1.9 Hz, 2H), 4.49 (s, 2H), 3.28 (t, J=7.1 Hz, 2H), 2.71 (s, 1H), 2.46 (t, J=8.1 Hz, 2H), 2.11-1.91 (m, 2H); LCMS (4 minute method) product at $R_t$=1.40 min and ES$^+$ m/z 351.09 [M+H]$^+$.

The starting material (60) was prepared as follows:

2-Chloro-6-(trifluoromethyl)pyridine-4-carbaldehyde (59)

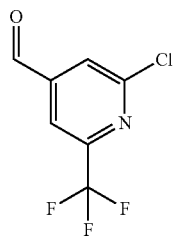 [SMILES: O=Cc1cc(Cl)nc(C(F)(F)F)c1]

To a solution of 2-chloro-6-trifluoromethylpyridine (58) (2.0 g, 11.0 mmol) in tetrahydrofuran (40 mL) at room temperature was added 2,2,6,6-tetramethylpiperidinylmagnesium chloride lithium chloride complex solution (1 M in THF/toluene) (13.2 mL, 13.2 mmol) dropwise. After stirring for 1 hour at room temperature the dark reaction mixture was cooled to −78° C. and a solution of N,N-dimethylformamide (1.71 mL, 22.0 mmol) in tetrahydrofuran (10 mL) was added dropwise. The reaction mixture was stirred for 1 hour at −78° C. and then allowed to warm to room temperature where it was stirred for a further 16 hours. The reaction mixture was quenched with saturated aqueous NH$_4$Cl (75 mL) and extracted with ethyl acetate (3×75 mL). The combined organic extracts were dried over magnesium sulfate, filtered and concentrated under reduced pressure. The residue was purified by flash column chromatography (25 g silica, petrol:EtOAc, 100:0 to 90:10). The desired fractions were concentrated under reduced pressure to afford the title compound as an orange oil (830 mg, 34%); $R_f$ 0.21 (5:95 MeOH:ethyl acetate); $^1$H NMR (500 MHz, Chloroform-d) δ 10.12 (s, 1H), 8.03 (s, 1H), 7.95 (s, 1H); LCMS (4 minute method) product at $R_t$=2.27 min and ES$^+$ m/z 242.02, 244.01 [M+MeOH+H]$^+$ (Cl isotope)

2-[4-[(2-Oxopyrrolidin-1-yl)methyl]phenyl]-6-(trifluoromethyl)pyridine-4-carbaldehyde (60)

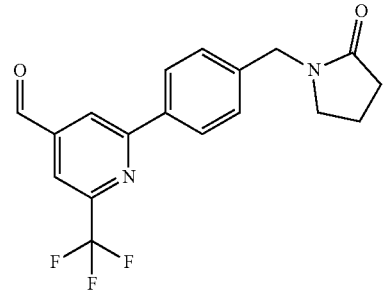 [SMILES: O=Cc1cc(-c2ccc(CN3CCCC3=O)cc2)nc(C(F)(F)F)c1]

A mixture of 1-[[4-(4,4,5,5-tetramethyl-1,3,2-dioxaborolan-2-yl)phenyl]methyl]pyrrolidin-2-one (8) (100 mg, 0.33 mmol), bis(triphenylphosphine)palladium(II) dichloride (12 mg, 0.020 mmol), 2-chloro-6-(trifluoromethyl)pyridine-4-carbaldehyde (59) (70 mg, 0.33 mmol) and sodium carbonate (106 mg, 1.00 mmol) in acetonitrile (4 mL) and water (1 mL) was degassed under a flow of nitrogen and heated in a microwave reactor at 145° C. for 20 min. The reaction was diluted with water (15 mL) and extracted into EtOAc (3×20 mL). The combined organic extracts were dried over magnesium sulfate, filtered and concentrated under reduced pressure. The residue was purified by flash column chromatography (10 g silica, EtOAc:MeOH, 100:0 to 95:5). The desired fractions were concentrated under reduced pressure to afford the title compound as a pale yellow oil (65 mg, 48%); $R_f$ 0.44 (5:95 MeOH:ethyl acetate); $^1$H NMR (500 MHz, Chloroform-d) δ 10.20 (s, 1H), 8.31 (s, 1H), 8.10 (d, J=8.2 Hz, 2H), 8.00 (s, 1H), 7.41 (d, J=8.2 Hz, 2H), 4.54 (s, 2H), 3.31 (t, J=7.0 Hz, 2H), 2.47 (t, J=8.1 Hz, 2H), 2.10-1.96 (m, 2H); LCMS (4 minute method) product at $R_t$=2.33 min and ES$^+$ m/z 349.06 [M+H]$^+$ Example 26: 1-[[4-[4-(Methoxymethyl)-6-(trifluoromethyl)-2-pyridyl]phenyl]methyl]pyrrolidin-2-one (62)

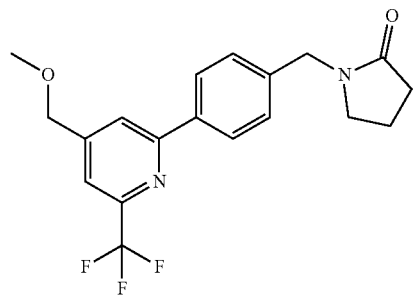 [SMILES: COCc1cc(-c2ccc(CN3CCCC3=O)cc2)nc(C(F)(F)F)c1]

To a solution of 1-[[4-[4-(hydroxymethyl)-6-(trifluoromethyl)-2-pyridyl]phenyl]methyl]pyrrolidin-2-one (61) (17 mg, 0.05 mmol) in tetrahydrofuran (1 mL) and was added sodium hydride (60% in oil) (5.6 mg, 0.15 mmol). The yellow reaction mixture was stirred for 30 minutes before the addition of iodomethane (9.0 µL, 0.15 mmol). The reaction mixture was stirred at room temperature for 18 hours before being quenched with MeOH (100 µL) and then concentrated under reduced pressure. The residue was purified by flash column chromatography (5 g silica, petrol: EtOAc, 100:0 to 0:100). The desired fractions were concentrated under reduced pressure to afford the title compound as a yellow gum (11 mg, 56%); R$_f$ 0.16 (100% ethyl acetate); $^1$H NMR (500 MHz, Chloroform-d) δ 8.04 (d, J=8.2 Hz, 2H), 7.86 (s, 1H), 7.57 (s, 1H), 7.37 (d, J=8.1 Hz, 2H), 4.60 (s, 2H), 4.52 (s, 2H), 3.51 (s, 3H), 3.29 (t, J=7.1 Hz, 2H), 2.47 (t, J=8.1 Hz, 2H), 2.02 (p, J=7.5 Hz, 2H); LCMS (4 minute method) product at R$_t$=3.01 min and ES$^+$ m/z 365.09 [M+H]$^+$ Example 27: 1-[[4-[4-Methyl-6-(trifluoromethyl) pyrimidin-2-yl]phenyl]methyl]pyrrolidin-2-one (67)

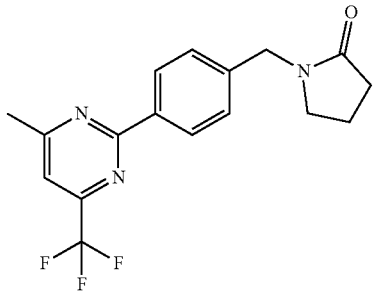 [SMILES: Cc1cc(C(F)(F)F)nc(-c2ccc(CN3CCCC3=O)cc2)n1]

A mixture of acetic acid; 4-[(2-oxopyrrolidin-1-yl) methyl]benzamidine (66) (99 mg, 0.36 mmol), (E)-1,1,1-trifluoro-4-methoxy-3-penten-2-one (50 mg, 0.30 mmol) and sodium ethoxide (24 mg, 0.36 mmol) in ethanol (500 µL) were heated at 70° C. for 18 hours. The reaction mixture was concentrated under reduced pressure and the residue was purified by flash column chromatography (10 g silica, petrol:EtOAc, 100:0 to 0:100). The desired fractions were concentrated under reduced pressure to afford the title compound as a colourless oil that solidified upon standing (75 mg, 74%); R$_f$ 0.25 (8:2 ethyl acetate:petrol); $^1$H NMR (500 MHz, Chloroform-d) δ 8.46 (d, J=8.2 Hz, 2H), 7.38-7.34 (m, 3H), 4.53 (s, 2H), 3.28 (t, J=7.1 Hz, 2H), 2.69 (s, 3H), 2.46 (t, J=8.1 Hz, 2H), 2.01 (p, J=7.5 Hz, 2H); LCMS (4 minute method) product at R$_t$=0.66 min and ES$^+$ m/z 336.11 [M+H]$^+$ The starting material (66) was prepared as follows:

4-[(2-Oxopyrrolidin-1-yl)methyl]benzonitrile (64)

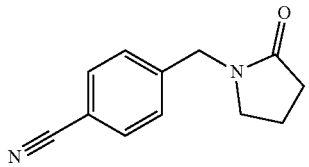 [SMILES: N#Cc1ccc(CN2CCCC2=O)cc1]

To a solution of pyrrolidin-2-one (0.79 mL, 10.2 mmol) in N,N-dimethylformamide (10 mL) at 0° C. was added sodium hydride (60% in oil) (489 mg, 12.2 mmol) portionwise and the mixture was left stirring at 0° C. for about 30 min. Then 4-(bromomethyl)benzonitrile (63) (2.0 g, 10.2 mmol) was added portionwise over 5 min. and the reaction mixture allowed to warm to room temperature and stirred for 16 hours. The reaction mixture was quenched with water and diluted with EtOAc (100 mL). The organic layer was washed with brine (3×100 mL), dried (MgSO$_4$) and solvent evaporated under reduced pressure, the crude was purified by flash chromatography (Biotage, 25 g) eluting with EtOAc:petrol (50:50 to 100:0). Fractions containing product were combined and evaporated under reduced pressure to afford the title compound as a white solid (1.72 g, 82%); $^1$H NMR (500 MHz, Chloroform-d)) δ 7.63 (d, J=8.2 Hz, 2H), 7.36 (d, J=8.3 Hz, 2H), 4.51 (s, 2H), 3.29 (t, J=7.1 Hz, 2H), 2.47 (t, J=8.1 Hz, 2H), 2.05 (p, J=7.5 Hz, 2H); LCMS (7 minute method) product at R$_t$=1.27 min and ES$^+$ m/z 201.11 [M+H]$^+$ N'-Hydroxy-4-[(2-oxopyrrolidin-1-yl)methyl]benzamidine (65)

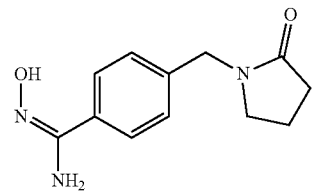 [SMILES: N/C(=N/O)c1ccc(CN2CCCC2=O)cc1]

To 4-[(2-oxopyrrolidin-1-yl)methyl]benzonitrile (64) (660 mg, 3.30 mmol) in ethanol (10 mL) was added hydroxylamine hydrochloride (687 mg, 9.89 mmol) followed by potassium carbonate (1.37 g, 9.89 mmol) and the reaction mixture was heated at refluxed for 16 hours. Volatiles were removed under reduced pressure, the residue was diluted with brine (50 mL) and extracted extensively into DCM (5×50 mL). The combined organic layers were dried (MgSO$_4$), filtered and evaporated under reduced pressure to afford the title compound as a white foam (745 mg, 76%); $^1$H NMR (500 MHz, DMSO-d$_6$) δ 9.58 (s, 1H), 7.63 (d, J=8.2 Hz, 2H), 7.20 (d, J=8.1 Hz, 2H), 5.75 (s, 2H), 4.36 (s, 2H), 3.22 (t, J=7.1 Hz, 2H), 2.29 (t, J=8.0 Hz, 2H), 1.98-1.86 (m, 2H); LCMS (4 minute method) product at R$_t$=0.31 min and ES$^+$ m/z 234.12 [M+H]$^+$ Acetic Acid; 4-[(2-oxopyrrolidin-1-yl)methyl]benzamidine (66)

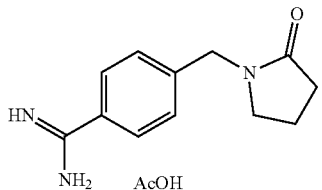 [SMILES: "AcOH" ; N=C(N)c1ccc(CN2CCCC2=O)cc1]

To N'-hydroxy-4-[(2-oxopyrrolidin-1-yl)methyl]benzamidine (65) (740 mg, 3.17 mmol) in acetic acid (20 mL) was added acetic anhydride (0.45 mL, 4.76 mmol). The mixture was stirred at for 10 min, then 10% palladium on carbon (101 mg) was added and the mixture was hydrogenated (1 bar hydrogen) at 25° C. for 24 hours. The catalyst was filtered off and washed with acetic acid/methanol. The filtrate was evaporated under reduced pressure to afford the title compound as a beige solid (945 mg, 84%); $^1$H NMR (500 MHz, DMSO-d$_6$) δ 7.76 (d, J=8.2 Hz, 2H), 7.41 (d, J=8.0 Hz, 2H), 4.45 (s, 2H), 3.30-3.19 (m, 2H), 2.34-2.24

(m, 2H), 2.01-1.89 (m, 2H), 1.81 (s, 3H); LCMS (7 minute method) product at R$_t$=0.45 min and ES$^+$ m/z 218.23 [M+H]$^+$ Example 28: 1-[[4-[6-(Difluoromethyl)-3-(hydroxymethyl)-2-pyridyl]phenyl]methyl]pyrrolidin-2-one (74)

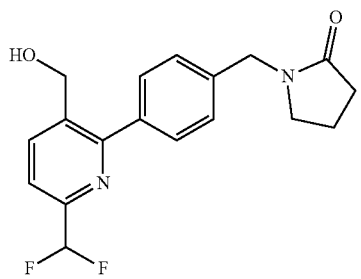 [SMILES: O=C1CCCN1Cc1ccc(-c2nc(C(F)F)ccc2CO)cc1]

A mixture of 1-[[4-(4,4,5,5-tetramethyl-1,3,2-dioxaborolan-2-yl)phenyl]methyl]pyrrolidin-2-one (8) (185 mg, 0.61 mmol), bis(triphenylphosphine)palladium(II) dichloride (21 mg, 0.03 mmol), [2-chloro-6-(difluoromethyl)-3-pyridyl]methanol (73) (119 mg, 0.61 mmol) and sodium carbonate (195 mg, 1.84 mmol) in acetonitrile (3 mL) and water (1 mL) was degassed under a flow of nitrogen and heated in a microwave reactor at 135° C. for 15 min. The reaction was diluted with water (10 mL) and extracted into EtOAc (2×20 mL). The organics were dried (MgSO$_4$), filtered and concentrated under reduced pressure to give a crude mixture which was purified by column chromatography (SiO$_2$, 10 g; gradient elution 10% EtOAc in petrol to 100% EtOAc). The desired fractions were combined and concentrated under reduced pressure to afford the title compound as a light yellow solid (105 mg, 49%); $^1$H NMR (500 MHz, Chloroform-d) δ 8.13 (d, J=8.0 Hz, 1H), 7.67 (d, J=8.0 Hz, 1H), 7.52 (d, J=8.1 Hz, 2H), 7.33 (d, J=8.0 Hz, 2H), 6.68 (t, J=55.4 Hz, 1H), 4.73 (s, 2H), 4.49 (s, 2H), 3.30 (t, J=7.1 Hz, 2H), 2.45 (t, J=8.1 Hz, 2H), 2.03-1.97 (m, 2H); LCMS (4 minute method) product at R$_t$=1.01 min and ES$^+$ m/z 333.09 [M+H]$^+$ The starting material (73) was prepared as follows:

Methyl 2-chloro-6-methyl-pyridine-3-carboxylate (69)

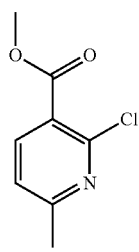

To a solution of 2-chloro-6-methylpyridine-3-carboxylic acid (68) (5.0 g, 29.1 mmol) in N,N-dimethylformamide (50 mL) was added potassium carbonate (12.1 g, 87.4 mmol) followed by iodomethane (5.4 mL, 87.4 mmol) and the reaction mixture was stirred at room temperature overnight. The reaction mixture was diluted with EtOAc (50 mL) and the suspension was filtered. The filtrate was then concentrated down and the remaining residue was taken up in EtOAc (150 mL). The solution was washed with water (75 mL) and brine (75 mL). The organic layer was dried over MgSO$_4$, filtered and concentrated under reduced pressure to afford the title compound leave a yellow oil (5.0 g, 91%); $^1$H NMR (500 MHz, Chloroform-d) δ 8.08 (d, J=7.8 Hz, 1H), 7.16 (d, J=7.8 Hz, 1H), 3.94 (s, 3H), 2.59 (s, 3H); LCMS (4 minute method) product at R$_t$=1.14 min and ES$^+$ m/z 186.19 [M+H]$^+$ Methyl 2-chloro-6-[(E)-2-(dimethylamino)vinyl] pyridine-3-carboxylate (70)

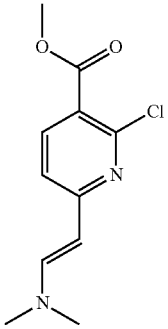 [SMILES: COC(=O)c1ccc(/C=C/N(C)C)nc1Cl]

To a mixture of methyl 2-chloro-6-methyl-pyridine-3-carboxylate (69) (5.0 g, 26.9 mmol) in N,N-dimethylformamide (25 mL) was added N,N-dimethylformamide dimethyl acetal (8.9 mL, 67.4 mmol) and the reaction mixture was heated to 120° C. overnight. N,N-dimethylformamide dimethyl acetal (4.3 mL, 32.3 mmol) was added and heating continued at 120° C. for another 3 hours. The mixture was cooled to room temperature and concentrated under reduced pressure. The orange residue was taken up in EtOAc (100 mL) and the solution was washed with water (80 mL) and brine (80 mL). The organic layer was dried (MgSO$_4$), filtered and concentrated under reduced pressure to afford the title compound as an orange oil (6.2 g, 86%); $^1$H NMR (500 MHz, Chloroform-d) δ 7.92 (d, J=8.2 Hz, 1H), 7.68 (d, J=12.8 Hz, 1H), 6.71 (d, J=8.2 Hz, 1H), 5.10 (d, J=12.8 Hz, 1H), 3.88 (s, 3H), 2.96 (s, 6H); LCMS (4 minute method) product at R$_t$=0.92 min and ES$^+$ m/z the desired mas ion was not observed.

Methyl 2-chloro-6-formyl-pyridine-3-carboxylate (71)

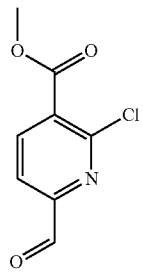

A solution of sodium periodate (9.95 g, 46.5 mmol) in water (25 mL) was added to a solution of methyl 2-chloro- 6-[(E)-2-(dimethylamino)vinyl]pyridine-3-carboxylate (70) (5.6 g, 23.2 mmol) in tetrahydrofuran (80 mL) at room temperature. The mixture was stirred for about 2 hours and then quenched with an aqueous solution of sodium thiosulfate. The mixture was filtered and the filtrate was diluted with more water (100 mL) and extracted with EtOAc (2×100 mL). The combined organic layers were washed with brine (50 mL), dried (MgSO$_4$), filtered and concentrated under reduced pressure to afford an orange solid. (3.9 g). The crude material was purified twice by column chromatography (SiO$_2$, 25 g; gradient elution 100% petrol to 50% EtOAc in petrol). The desired fractions were combined and concentrated under reduced pressure to afford the title compound as an orange solid (838 mg, 14%); $^1$H NMR (500 MHz, Chloroform-d) δ 10.04 (s, 1H), 8.31 (d, J=7.8 Hz, 1H), 7.95 (d, J=7.8 Hz, 1H), 4.01 (s, 3H); LCMS (4 minute method) product at R$_t$=0.97 min and ES$^+$ m/z 200.17 [M+H]$^+$ Methyl 2-chloro-6-(difluoromethyl)pyridine-3-carboxylate (72)

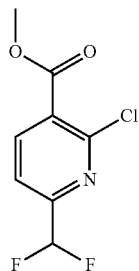

To a solution of methyl 2-chloro-6-formyl-pyridine-3-carboxylate (71) (200 mg, 1.0 mmol) in DCM (5 mL) at 0° C. was added [bis(2-methoxyethyl)amino]sulphur trifluoride (50 wt % solution in toluene) (0.46 mL, 2.51 mmol). The reaction mixture was allowed to warm up to room temperature and was stirred overnight. The reaction mixture was quenched with sat. aq. NaHCO$_3$, the layers were separated and the aqueous layer was extracted with DCM (2×15 mL). The combined organic layers were washed with brine (25 mL), dried (MgSO$_4$), filtered and concentrated under reduced pressure to leave a light yellow oil. This oil was purified by column chromatography (10 g, SiO$_2$; gradient elution 100% petrol to 80% EtOAc in petrol). The desired fractions were combined and concentrated under reduced pressure to afford the title compound as a white solid (113 mg, 48%); $^1$H NMR (500 MHz, Chloroform-d) δ 8.31 (d, J=7.9 Hz, 1H), 7.67 (d, J=7.9 Hz, 1H), 6.61 (t, J=54.9 Hz, 1H), 4.00 (s, 3H); LCMS (4 minute method) product at R$_t$=2.30 min and ES$^+$ m/z 222.09 [M+H]$^+$ 2-Chloro-6-(difluoromethyl)-3-pyridyl]methanol (73)

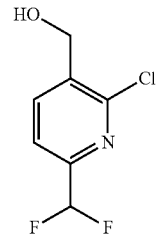 [SMILES: OCc1ccc(C(F)F)nc1Cl]

To a solution of methyl 2-chloro-6-(difluoromethyl)pyridine-3-carboxylate (72) (170 mg, 0.77 mmol) in DCM (15 mL) at 0° C. was added diisobutylaluminum hydride (1 M solution in toluene) (2.3 mL, 2.3 mmol) and the mixture was slowly allowed to warm to room temperature. After 2 hours the reaction mixture was quenched with sat. aq. Rochelle's salt and stirred for 30 min before being concentrated under reduced pressure. The product was then extracted into DCM (3×20 mL). The combined organic layers were washed with brine (30 mL), dried over (MgSO$_4$), filtered and then concentrated under reduced pressure to afford the title compound as a clear oil which solidified upon standing (130 mg, 83%); $^1$H NMR (500 MHz, Chloroform-d) δ 8.07 (d, J=7.8 Hz, 1H), 7.64 (d, J=7.8 Hz, 1H), 6.60 (t, J=55.2 Hz, 1H), 4.84 (s, 2H); LCMS (4 minute method) product at R$_t$=0.70 min and ES$^+$ m/z 194.13 [M+H]$^+$ Biological Data AMPA Calcium Ion Influx Assay The ability of the compounds of the invention to potentiate glutamate receptor-mediated response was determined using fluorescent calcium-indicator dye.

96 well plates were prepared containing confluent monolayer of HEK 293 cells stably expressing human GluR2 flip (unedited) AMPA receptor subunit (obtained from GlaxoSmithKline). These cells form functional homotetrameric AMPA receptors. The tissue culture medium in the wells was discarded and the wells were each washed three times with standard buffer for the cell line (145 µM NaCl, 5 mM KCl, 1 mM MgCl$_2$, 2 mM CaCl$_2$, 20 mM N-[2-hydroxyethyl]-piperazine-N-[2-ethanesulfonic acid (HEPES), 5.5 mM glucose, pH7.3). The plates were then incubated for 60 minutes in the dark with 2 µM Calcium 6 dye (Molecular Devices). After incubation, each well was washed three times with buffer (80 µl).

Compounds of the invention were dissolved in dimethylsulfoxide (DMSO) at a stock concentration of 10 mM. These solutions were further diluted with DMSO. Each dilution (4 µl) to another compound plate and buffer (200 µl) was added. An agonist stimulus plate (glutamate) was prepared by dissolving sodium glutamate in water to give a concentration of 100 mM. This solution was diluted with buffer to give a final concentration of 500 µM and dispensed into another 96 well plate (200 µl/well).

The cell plate was then transferred to a fluorescence imaging plate reader such as the Flexstation 3 (Molecular Devices). A baseline fluorescence was taken over a 10 to 240 second period and then 40 µl from each plate containing a compound of the invention made up in standard buffer solution was added. Volumes were chosen to give a final concentration range of 40 µM to 4 µM. The fluorescence was then read over a 4 minute period. The activities of the compounds were determined by measuring peak fluorescence after the last addition. The activity can also be expressed relative to the fluorescence increase induced by cyclothiazide at their maximum response (i.e. greater than 40 µM).

Intrinsic Clearance (CLi)

The in-vitro intrinsic clearance of certain compounds was measured in rat and human hepatocytes using the following assay.

5 µL microsomes (20 mg/ml, Corning BV) diluted into 95 µL PBS (pH 7) containing 0.2% DMSO and 4 µM test article were incubated at 37° C. shaking at 1000 rpm prior the addition of 100 µL of pre-warmed 4 mM NADPH in PBS (final concentrations: 0.5 mg/mL microsomes, 2 µM test article, 0.1% DMSO and 2 mM NADPH). After mixing thoroughly the T=0 sample (40 µL) was immediately quenched into ice cold methanol containing 2 µM internal standard (Carbemazapine). Three further samples were quenched in the same way at 3, 9 and 30 min. Samples were incubated on ice for 30 min before centrifugation at 4000 rpm+ for 200 min. The supernatant was analysed via LCMS and the test article:carbemazapine peak area ratios calculated to determine the rate of substrate depletion.

Biological Data

The table below shows the mean % response in the AMPA calcium ion influx assay described above at a test compound concentration of 10 µM

| Example # (Compound #) | Structure | Mean % response at 10 µM |
|---|---|---|
| Example 1 (32) | 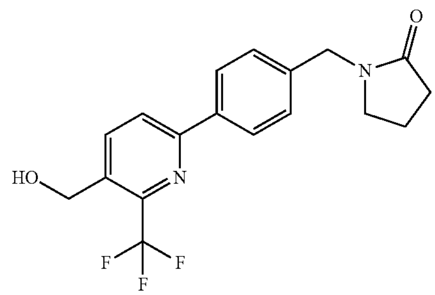 [SMILES: O=C1CCCN1Cc1ccc(-c2ccc(CO)c(C(F)(F)F)n2)cc1] | 33 |
| Example 2 (33) | 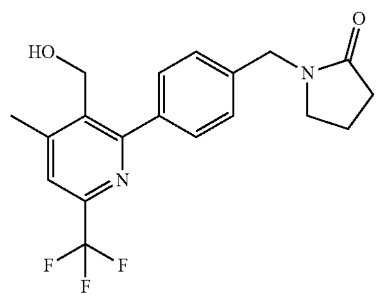 [SMILES: Cc1cc(C(F)(F)F)nc(-c2ccc(CN3CCCC3=O)cc2)c1CO] | 41 |
| Example 3 (34) | 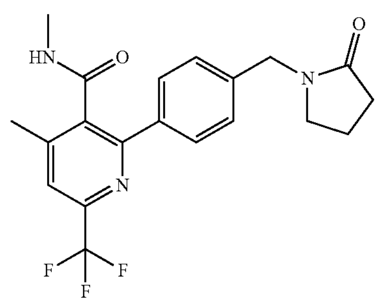 [SMILES: CNC(=O)c1c(C)cc(C(F)(F)F)nc1-c1ccc(CN2CCCC2=O)cc1] | 4 |
| Example 4 (36) | 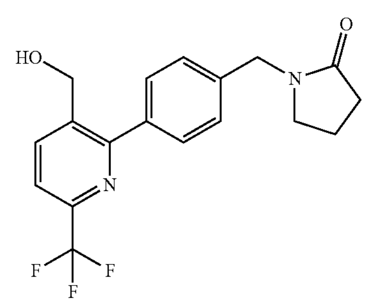 [SMILES: O=C1CCCN1Cc1ccc(-c2nc(C(F)(F)F)ccc2CO)cc1] | 9 |

-continued
| Example # (Compound #) | Structure | Mean % response at 10 μM |
|---|---|---|
| Example 5 (37) | 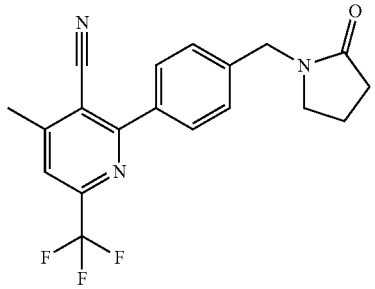 [SMILES: Cc1cc(C(F)(F)F)nc(-c2ccc(CN3CCCC3=O)cc2)c1C#N] | 99 |
| Example 6 (38) | 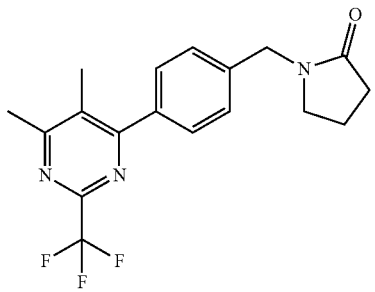 [SMILES: Cc1nc(C(F)(F)F)nc(-c2ccc(CN3CCCC3=O)cc2)c1C] | 29 |
| Example 7 (39) | 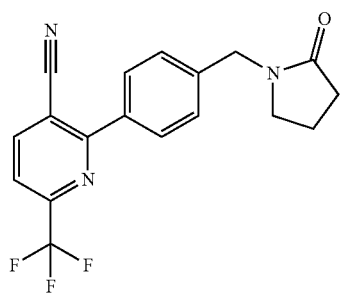 | 21 |
| Example 8 (40) | 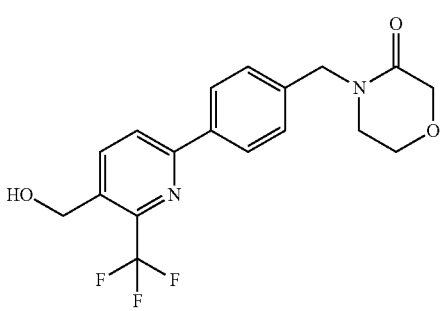 | 14 |
| Example 9 (41) | 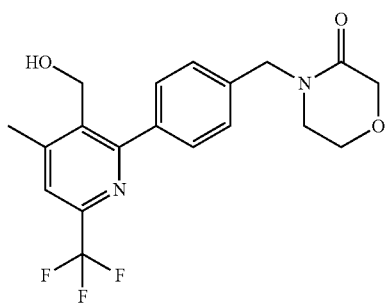 [SMILES: Cc1cc(C(F)(F)F)nc(-c2ccc(CN3CCOCC3=O)cc2)c1CO] | 14 |

-continued
| Example # (Compound #) | Structure | Mean % response at 10 μM |
|---|---|---|
| Example 10 (42) | 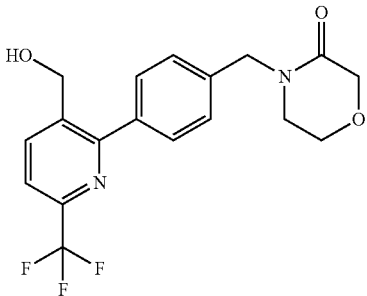 [SMILES: O=C1COCCN1Cc1ccc(-c2nc(C(F)(F)F)ccc2CO)cc1] | 3 |
| Example 11 (43) | 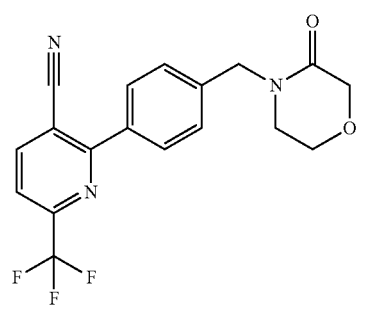 [SMILES: N#Cc1ccc(C(F)(F)F)nc1-c1ccc(CN2CCOCC2=O)cc1] | 11 |
| Example 12 (44) | 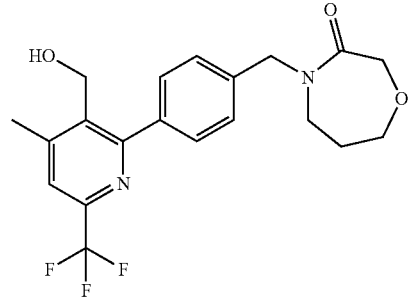 [SMILES: Cc1cc(C(F)(F)F)nc(-c2ccc(CN3CCCOCC3=O)cc2)c1CO] | 9 |
| Example 13 (45) | 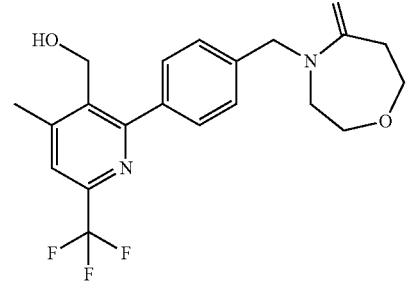 | 5 |
| Example 14 (46) | 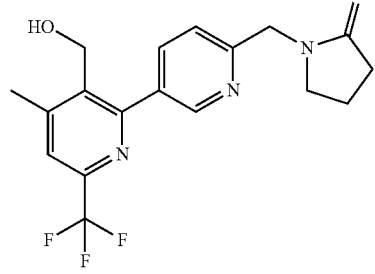 | 5 |

-continued

| Example # (Compound #) | Structure | Mean % response at 10 μM |
|---|---|---|
| Example 15 (48) | 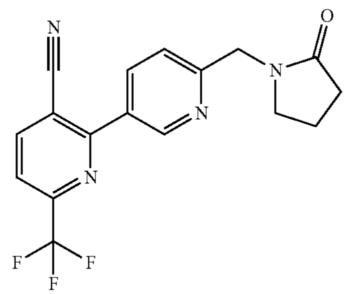 | 6 |
| Example 16 (49) | 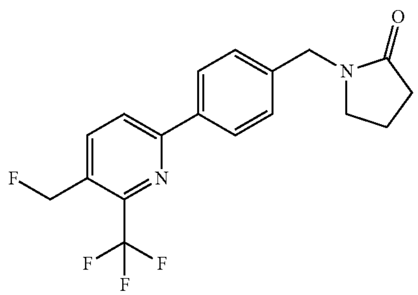 [SMILES: O=C1CCCN1Cc1ccc(-c2ccc(CF)c(C(F)(F)F)n2)cc1] | 28 |
| Example 17 (50) | 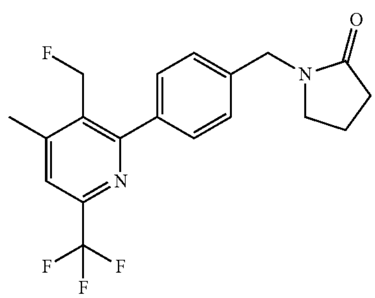 [SMILES: Cc1cc(C(F)(F)F)nc(-c2ccc(CN3CCCC3=O)cc2)c1CF] | 111 |
| Example 18 (51) | 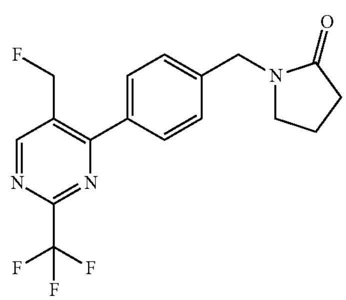 [SMILES: O=C1CCCN1Cc1ccc(-c2nc(C(F)(F)F)ncc2CF)cc1] | 5 |
| Example 19 (52) | 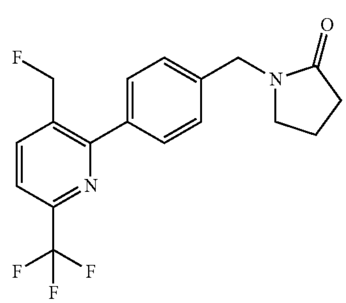 | 70 |

-continued

| Example # (Compound #) | Structure | Mean % response at 10 μM |
|---|---|---|
| Example 20 (53) | 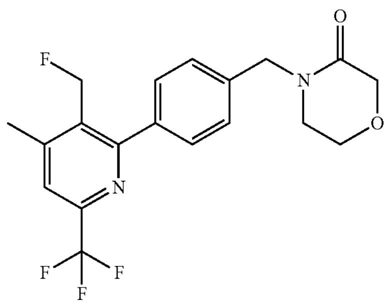 [SMILES: Cc1cc(C(F)(F)F)nc(-c2ccc(CN3CCOCC3=O)cc2)c1CF] | 112 |
| Example 21 (54) | 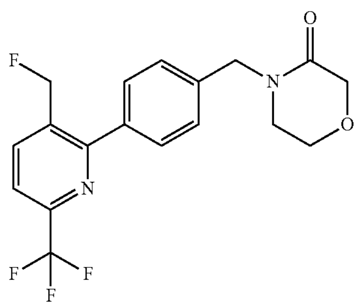 [SMILES: O=C1COCCN1Cc1ccc(-c2nc(C(F)(F)F)ccc2CF)cc1] | 16 |
| Example 22 (55) | 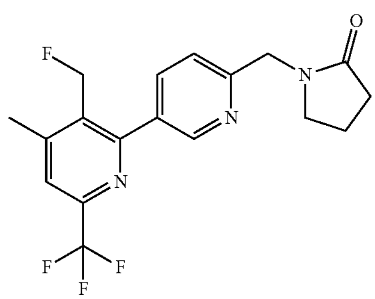 [SMILES: Cc1cc(C(F)(F)F)nc(-c2ccc(CN3CCCC3=O)nc2)c1CF] | 93 |
| Example 23 (56) | 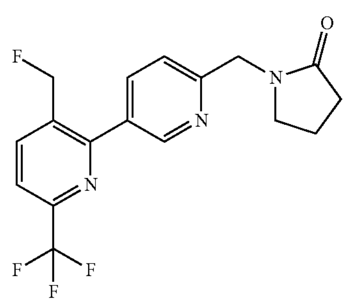 | 9 |
| Example 24 (57) | 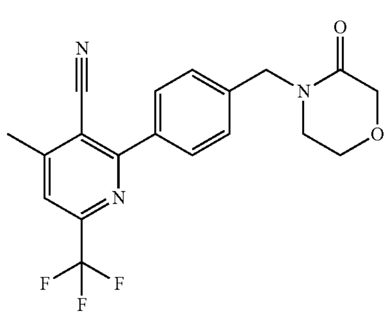 [SMILES: Cc1cc(C(F)(F)F)nc(-c2ccc(CN3CCOCC3=O)cc2)c1C#N] | 39 |

| Example # (Compound #) | Structure | Mean % response at 10 μM |
|---|---|---|
| Example 25 (61) | 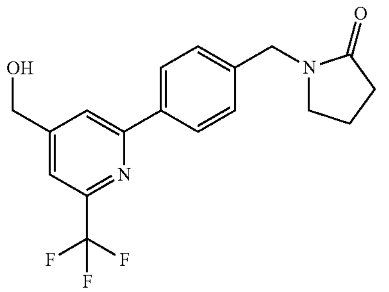 [SMILES: O=C1CCCN1Cc1ccc(-c2cc(CO)cc(C(F)(F)F)n2)cc1] | 8 |
| Example 26 (62) | 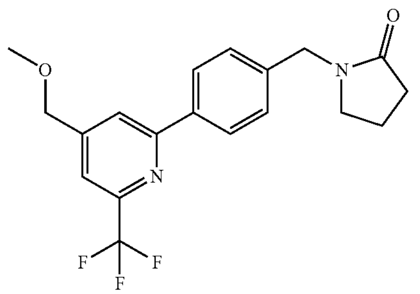 [SMILES: COCc1cc(-c2ccc(CN3CCCC3=O)cc2)nc(C(F)(F)F)c1] | 4 |
| Example 27 (67) | 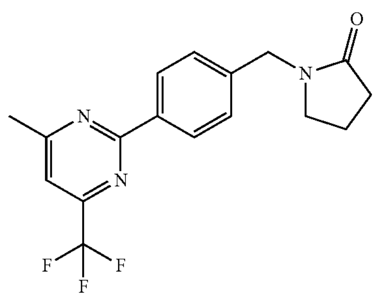 [SMILES: Cc1cc(C(F)(F)F)nc(-c2ccc(CN3CCCC3=O)cc2)n1] | 27 |
| Example 28 (74) | 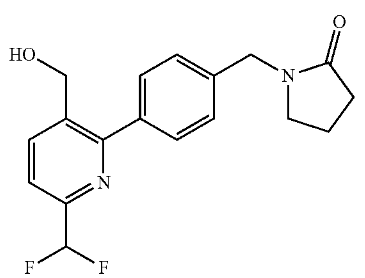 [SMILES: O=C1CCCN1Cc1ccc(-c2nc(C(F)F)ccc2CO)cc1] | 2 |

Electrophysiology Assay

The ability of the compounds of the invention to increase AMPA mediated currents was demonstrated using in-vitro whole cell voltage clamp electrophysiology.

Primary hippocampal neuronal cultures were prepared using an in-house procedure similar to Nunez (JoVE. 2008, DOI: 10.3791/895) from rat pups (P0-P1) and electrophysiology recordings were made 2-4 weeks post harvesting.

Dissociated neurons were plated in culture dishes containing coverslips coated with poly-D-lysine and laminin, and maintained at 37° C. with 5% $CO_2$ in a humidified atmosphere. Cells were cultured in neurobasal media supplemented with foetal bovine serum (2%), glucose 45% (0.4%), Na-pyruvate (1 mM), HEPES (10 mM), serum free B-27 supplement 50× (1%), penicillin-streptomycin (1%) and glutamax (1%). Cells were fed on day 3, day 5 and then every three days by replacing half of the volume with freshly prepared media. From day 5 the media was supplemented with cytosine arabinoside (Ara-C, 4 μg/ml) to prevent glial cell proliferation.

Test compounds were dissolved in dimethylsulfoxide (DMSO) to produce 10 mM stock solutions. On the day of recordings they were diluted into the extracellular recording solution to the desired final concentration while maintaining a final DMSO concentration of 0.3% (v/v). The extracellular solution (145 mM NaCl, 2.5 mM KCl, 1.2 mM $MgCl_2$, 1.5 mM $CaCl_2$, 10 mM HEPES, 10 mM D-Glucose, 310 mOsm, pH adjusted to 7.35 with NaOH) was supplemented with the following ion channel blockers at the time of recordings: TTX (1 μM), (−)-bicuculline methobromide (10 μM), (+)-MK801 maleate (0.5 μM), strychnine (1 μM).

For recordings, coverslips were transferred to a 200 μl volume recording RSC200 system (RSC200, Biologics) chamber that was continuously perfused with extracellular buffer at a regulated flow rate (1.5 ml/min). Whole cell patch-clamp configuration was obtained using borosilicate glass electrodes pipettes of 3-8 MO resistance when filled with an intracellular solution containing 80 mM CsCl, 80 mM CsF, 10 mM HEPES (300 mOsm, pH adjusted to 7.3 using CsOH). Currents were recorded at room temperature using a patch-clamp amplifier (Axopatch 200B) with 2 kHz low-pass filter and subsequently digitized at 50 kHz with a Digidata 1322A/D and pClamp 10 data acquisition software (Axon Instruments, USA).

Clamped cells were kept at a holding potential of −70 mV and currents recorded in 15 s sweeps. Current responses were evoked by 3 s application of 30 μM s-AMPA every 57 s before and during co-application of the test compound. Only cells with stable currents to four applications of s-AMPA alone (<20% variation between first and fourth applications) were used for compound testing. Compounds were tested at variable concentrations between 10 and 10000 nM, with only one concentration applied per cell.

Data were analysed by evaluating the changes of three parameters (area under the curve, peak and stable AMPA activated current) in the presence of the test compound expressed as percentage of the same parameters before compound additions. The minimum effective concentration was the concentration of test compound that resulted in a statistically significant change in the parameter being monitored (area under the curve, peak and stable AMPA activated current).

Compounds UoS26495, UoS21365, UoS26417, UoS21372, UoS21424, UoS21472, UoS26366 and UoS26478 exemplified herein were tested in this assay had a minimum effective concentration (MEC) of less than 10 μM.

In-Vivo Assays

NOR Assay

Certain of the exemplified compounds (UoS21365 and UoS26478) have been tested in the Novel Object Recognition (NOR) assay analogous to that described in Ennaceur et al., (Behav. Brain Res. 1988, 31, 47-59) and exhibit a minimal effective dose of less than 10 mg/kg.

Sub-Chronic PCP-Induced Reversal Learning

The reversal learning task is an in-vivo assay for cognitive function that may be of particular relevance to schizophrenia (Abdul-Monim et al., Behav. Brain Res. 2006, 169, 263-273). Rats are trained over several weeks to press a lever contingent with a light cue for a food reward (either lever under a light, or lever not under a light). For the reversal task, rats are first given a 30 min operant training session with a constant contingency relative to the light cue. This is followed by a 5 min session called the "initial task", in which the contingency is the same as for the prior operant session. After the initial task there is a 5 min "reversal task" in which the contingency is reversed. Responses on correct and incorrect levers in the initial and reversal task are recorded. Once performance is stable the training is stopped and a cognitive deficit is induced in the rats via sub-chronic administration of phencyclidine (PCP) followed by at least 7-days washout (as a control some rats receive saline instead of PCP). The cognitive effects of drugs can be tested with acute administration of the test drug before the reversal task, with initial and reversal sessions as above. Risperidone, an atypical antipsychotic, is used as a positive control that is known to attenuate the cognitive deficit.

One of the compounds exemplified herein, "UoS26478" was tested acutely at doses of 3.0, 10 and 30 mg/kg (per oral, 30 min ptt) compared to risperidone (0.1 mg/kg, i.p, 60 min ptt) in sub-chronic phencyclidine (scPCP) treated rats (2 mg/kg, i.p. twice daily for seven days, followed by at least a 7-day washout period) to restore performance in the reversal learning task.

Results are shown in FIG. 1. The data in FIG. 1 shows mean±s.e.m. % correct lever responses (n=9-10) and were analysed by ANOVA and post-hoc LSD test. The compound of the invention, UoS26478, showed a significant increase at 10 and 30 mg/kg in correct responses compared to scPCP plus vehicle in the reversal phase; #P<0.05-##P<0.01. The compound at 3 mg/kg, and vehicle, showed a significant reduction in percentage of correct responses in the reversal phase compared with the rats which had not had scPCP induced cognitive deficit (scSaline+veh)*P<0.05, **P<0.01.

The invention claimed is:

1. A compound of the formula (I), or a pharmaceutically acceptable salt thereof:

$A^1$ is N or $CR^1$;
$A^2$ is N or $CR^3$;
and wherein only a single one of $A^1$ and $A^2$ may be N;
$R^1$ is selected from the group consisting of: H, CN, $C_{1-4}$ alkyl, $C_{1-4}$ haloalkyl, $C_{3-4}$ cycloalkyl, $—C_{1-4}$ alkyl-$OR^{41}$ and $—C(O)NR^{41}R^{B1}$;
$R^2$ is selected from the group consisting of: H, CN, $C_{1-4}$ alkyl, $C_{1-4}$ haloalkyl, $C_{3-4}$ cycloalkyl, $—C_{1-4}$ alkyl-$OR^{42}$ and $—C(O)NR^{42}R^{B2}$;
$R^3$ is selected from H, $C_{1-4}$ alkyl, $C_{1-4}$ haloalkyl, $C_{3-4}$ cycloalkyl, $—C_{1-4}$ alkyl-OH and $—C(O)NR^{43}R^{B3}$;
each X is independently H or F, provided at least one X is F;
$B^1$ and $B^2$ are independently CH or N;
$R^4$ is halo;
$X^1$ is O or $CH_2$;
$R^{41}$, $R^{B1}$, $R^{42}$, $R^{B2}$, $R^{43}$ and $R^{B3}$ are each independently selected from: H and $C_{1-4}$ alkyl;
a is an integer selected from 0, 1 or 2;
b is an integer selected from 0, 1 or 2;
a+b is 0, 1, 2 or 3; and
n is 0, 1 or 2;
with the following provisos:
$R^1$, $R^2$ and $R^3$ are not all H;
when $A^1$ is N, at least one of $R^2$ and $R^3$ is $C_{1-4}$ alkyl or $C_{1-4}$ haloalkyl;
when $A^2$ is N, at least one of $R^1$ and $R^2$ is $C_{1-4}$ alkyl or $C_{1-4}$ haloalkyl;
when $A^1$ is $CR^1$, $R^1$ is $—CH_2OH$ and $B^1$ is N, then $R^2$ is not H; and
when $A^1$ is $CR^1$, $R^1$ is $—CN$ and $B^2$ is N, then $R^2$ is not H.

2. The compound of claim 1, wherein the group —CX$_3$ is —CF$_3$.

3. The compound of claim 1, wherein B$^2$ is CH.

4. The compound of claim 1, wherein the group of the formula:

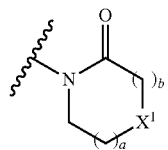

is selected from:

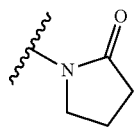 and 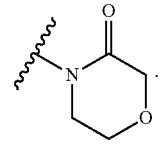.

5. The compound of claim 1, wherein the compound is of the formula (III), or a pharmaceutically acceptable salt thereof:

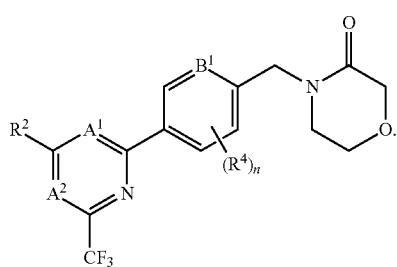

(III)

6. The compound of claim 1, wherein n is 0.

7. The compound of claim 1, wherein B$^1$ is N.

8. The compound of claim 1, wherein B$^1$ is CH.

9. The compound of claim 1, wherein A$^1$ is N or CR$^1$ and R$^1$ is selected from the group consisting of: H, CN, C$_{1-3}$ alkyl, C$_{1-3}$ fluoroalkyl, —C$_{1-3}$ alkyl-OH, —C$_{1-3}$ alkyl-OMe, —C(O)NH$_2$; —C(O)NHMe and —C(O)N(Me)$_2$.

10. The compound of claim 1, wherein A$^1$ is CR$^1$ and R$^1$ is CN.

11. The compound of claim 1, wherein R$^2$ is selected from the group consisting of: H, C$_{1-3}$ alkyl, C$_{1-3}$ fluoroalkyl, —C$_{1-3}$ alkyl-OH and —C$_{1-3}$ alkyl-OMe.

12. The compound of claim 1, wherein A$^2$ is N or CR$^3$ and R$^3$ is selected from the group consisting of: H, C$_{1-3}$ fluoroalkyl and —C$_{1-3}$ alkyl-OH.

13. The compound of claim 1, wherein A$^2$ is CH.

14. The compound of claim 1, wherein the group of the formula:

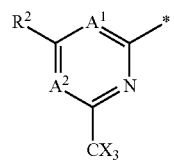

is selected from the group consisting of:

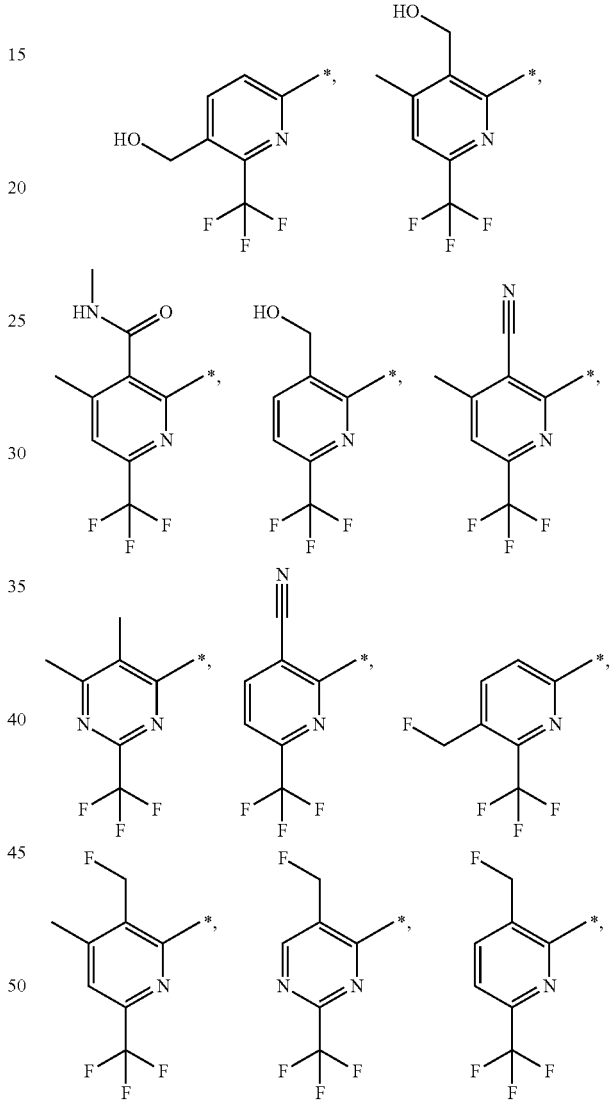

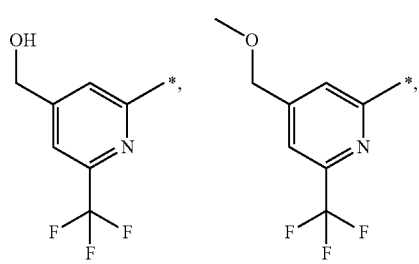

-continued
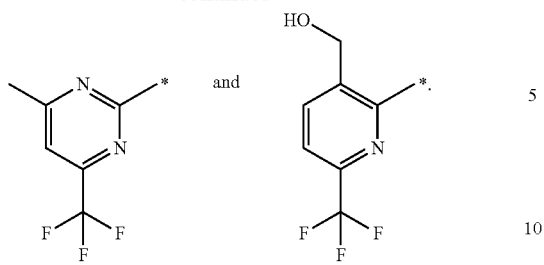
and
15. The compound of claim 1, wherein the group of the formula:
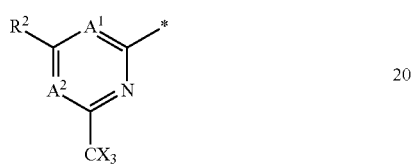
is selected from the group consisting of:
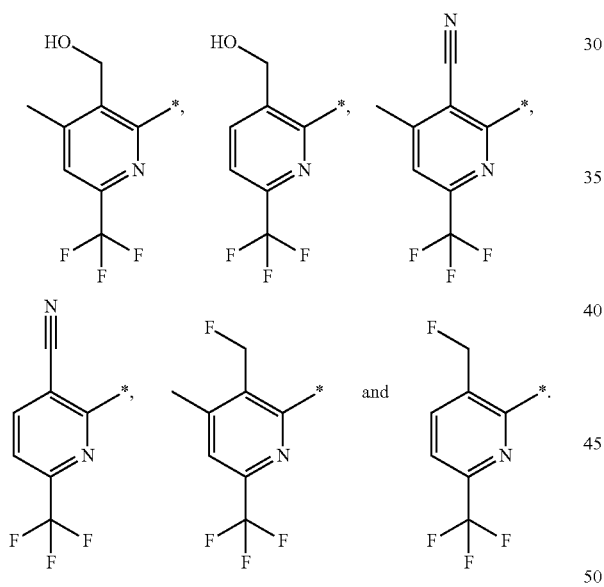
and
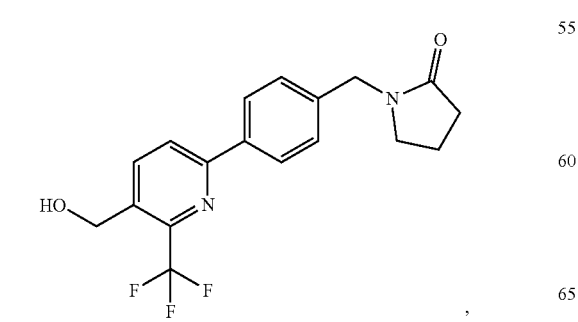
16. The compound of claim 1, selected from:
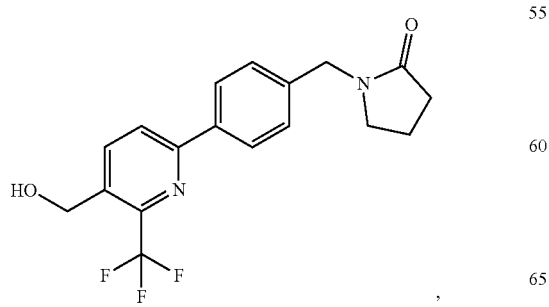
-continued
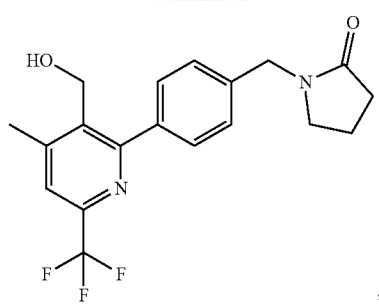
,
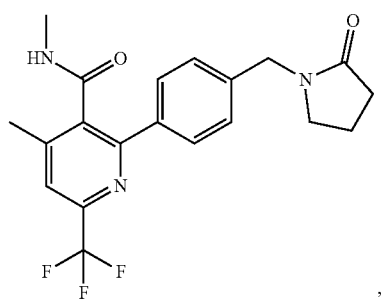
,
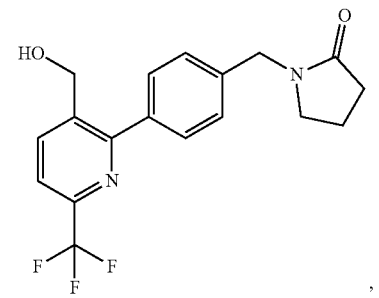
,
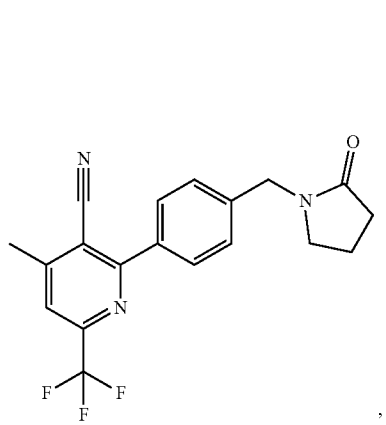
,
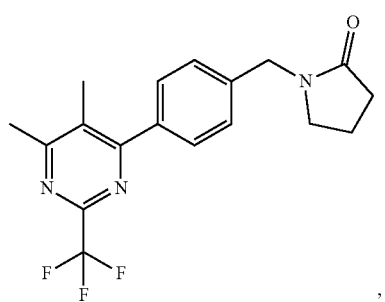
, 119
-continued
120
-continued
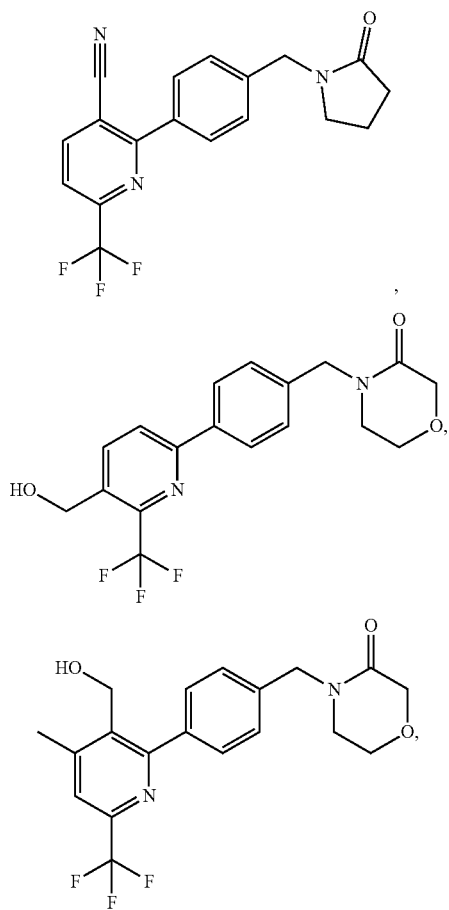
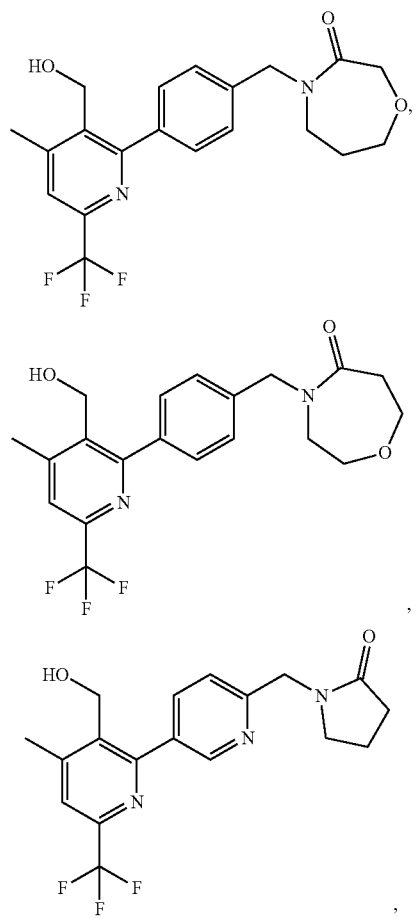
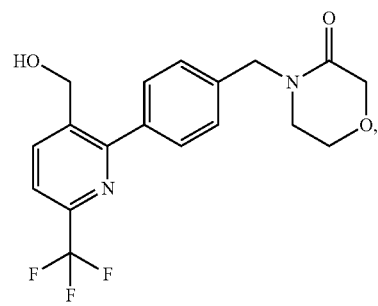
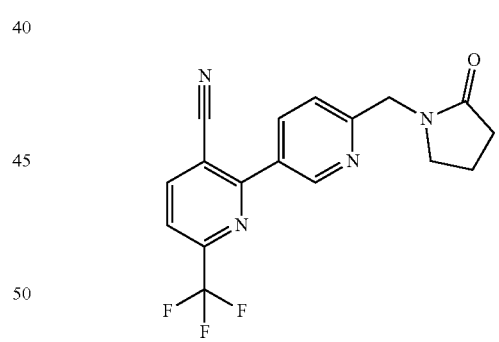
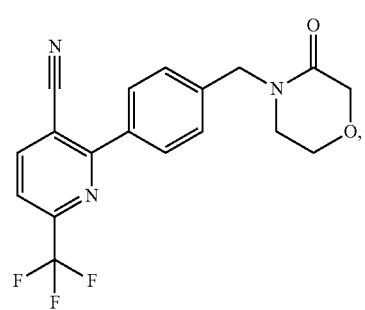
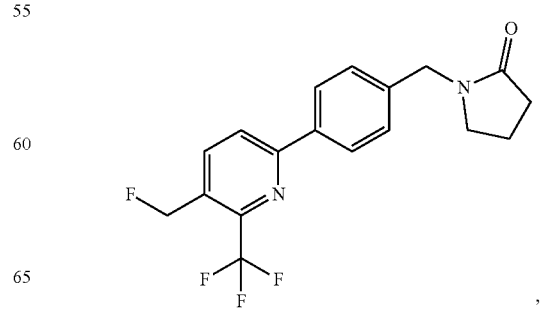

121
-continued

122
-continued

-continued

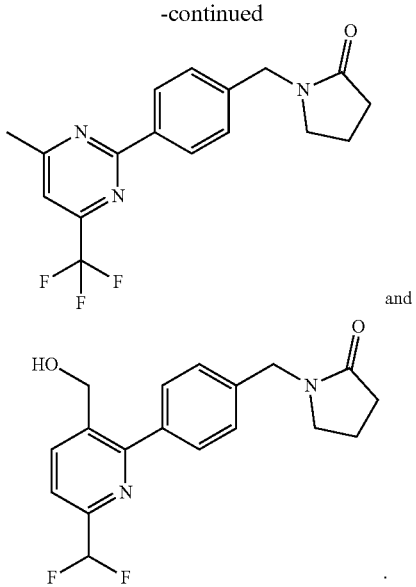
and

17. A pharmaceutical formulation comprising a compound of claim 1, and a pharmaceutically acceptable excipient.

18. A compound selected from a compound of the formula (XII) or (XIII), or a pharmaceutically acceptable salt thereof:

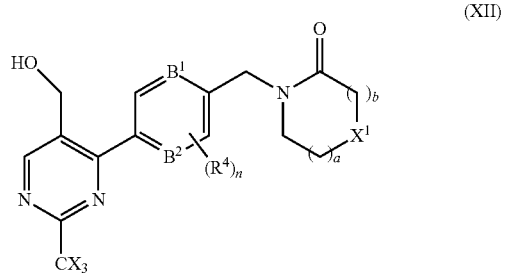
(XII)

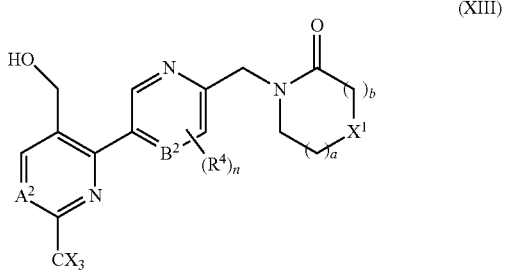
(XIII)

wherein $A^2$ is N or $CR^3$;

$B^1$ and $B^2$ are independently CH or N;

$R^4$ is halo;

each is independently H or F, provided at least one X is F;

$X^1$ is O or $CH_2$;

a is an integer selected from 0, 1 or 2;

b is an integer selected from 0, 1 or 2;

a+b is 0, 1, 2, or 3, and n is 0, 1 or 2.

19. A method for treating a condition which is modulated by an AMPA receptor in a subject in need thereof, the method comprising administering an effective amount of a compound according to claim 1, or a pharmaceutically acceptable salt thereof, to said subject.

20. A method for treating a condition selected from a depressive disorder, a mood disorder, cognitive dysfunction, a psychotic disorder, a bipolar disorder, attention-deficit hyperactivity disorder, a neurodegenerative disorder, a neurodevelopmental disorder, a motor neuron disease, ataxia, respiratory depression and a hearing disorder in a subject in need thereof, the method comprising administering an effective amount of a compound according to claim 1, or a pharmaceutically acceptable salt thereof, to said subject.

21. The method according to claim 20, wherein the condition is cognitive dysfunction associated with a neurological or neuropsychiatric disorder.

22. The method according to claim 20, wherein the condition is cognitive dysfunction associated with schizophrenia.

23. The method according to claim 20, wherein the compound is co-administered to a subject with an additional therapeutic agent.

* * * * *